United States Patent
Koh et al.

(10) Patent No.: US 6,723,724 B2
(45) Date of Patent: Apr. 20, 2004

(54) ISOXAZOLYLALKYLPIPERAZINE DERIVATIVES HAVING SELECTIVE BIOLOGICAL ACTIVITY AT DOPAMINE $D_3$ OR $D_4$ RECEPTOR, AND PREPARATION THEREOF

(75) Inventors: Hun Yeong Koh, Kyungki-do (KR); Kyung Il Choi, Seoul (KR); Yong Seo Cho, Seoul (KR); Ae Nim Pae, Seoul (KR); Kyung Ho Kang, Jeola-bookdo (KR); Mi Young Cha, Kyungki-do (KR); Jae Yang Kong, Daejeon (KR); Dae Young Jeong, Daejeon (KR); Hee-Yoon Lee, Daejeon (KR)

(73) Assignees: Korea Institute of Science and Technology, Seoul (KR); Korea Research Institute of Chemical Technology, Daejeon (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 09/839,206

(22) Filed: Apr. 23, 2001

(65) Prior Publication Data

US 2002/0119983 A1 Aug. 29, 2002

(30) Foreign Application Priority Data

Dec. 4, 2000 (KR) .......................... 2000-73121

(51) Int. Cl.⁷ .................... A61K 31/496; A61K 31/454; C07D 413/06
(52) U.S. Cl. .................. 514/254.04; 514/326; 544/367; 546/209
(58) Field of Search .................. 544/367; 546/209; 514/254.04, 326

(56) References Cited

U.S. PATENT DOCUMENTS 6,166,033 A * 12/2000 Nakazato et al. ........... 514/316

FOREIGN PATENT DOCUMENTS

| DE | 2234393 | * | 1/1974 |
| GB | 1023383 | * | 3/1966 |
| WO | 98/15541 | * | 4/1998 |
| WO | WO 99/43670 | | 9/1999 |

OTHER PUBLICATIONS

Hery et al. Medline Abstract for Encephale, vol. 19,pp. 525–532 (1993).*
Mason et al. Medline Abstract for Eur. J. Pharmacol.,vol. 221, pp. 397–398 (1992).*
Poetsch et al, Chemical Abstracts, vol. 80, No. 108516 (1974).*
"Advanced Organic Chemistry" by Jerry March (2nd ed.,), pp. 819–820.*
Christoph Thomas, et al, Enantio–and Diasterecontrolled Dopamine D1, D2, D3, and D4 Receptor Binding of N–(3–Pyrrolidinylmethyl)Benzamides Synthesized From Aspartic Acid, Bioorganic & Medicinal Chemistry Letters, 9 (1999) 841–846, Feb. 1999.
Michael Rowley, et al., 4–Heterocyclylpiperidines as Selective High–Affinity Ligands at the Human Dopamine D4 Receptor, Journal of Medicinal Chemistry, vol. 40., No. 15 pp2374–2385, 1997.
Shelly A. Glase, et al., Substituted [4–Phenylpiperazinyl-)–Methyl]Benzamides: Selective Dopamine D4 Agonists, Journal of Medicinal Chemistry, vol. 40, No. 12, pp. 1771–1772, 1997.

* cited by examiner

*Primary Examiner*—Emily Bernhardt
(74) *Attorney, Agent, or Firm*—Lowe Hauptman Gilman & Berner, LLP

(57) ABSTRACT

The present invention relates to isoxazolylalkylpiperazine derivatives having selective biological activity at dopamine $D_3$ or $D_4$ receptors represented by the following formula (1), and its preparation method through reductive amination reaction in the presence of reducing agent,

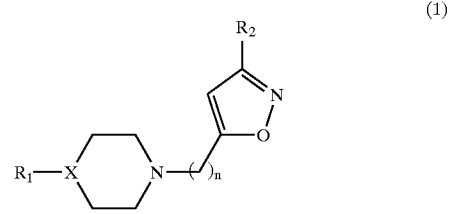

(1)

wherein $R_1$, $R_2$, X and n are the same as defined in the specification.

8 Claims, No Drawings

ISOXAZOLYLALKYLPIPERAZINE DERIVATIVES HAVING SELECTIVE BIOLOGICAL ACTIVITY AT DOPAMINE $D_3$ OR $D_4$ RECEPTOR, AND PREPARATION THEREOF

BACKGROUND OF THE INVENTION

Field of the Invention

The present invention relates to isoxazolylalkylpiperazine derivatives having selective biological activity at dopamine $D_3$ or $D_4$ receptors represented by the following formula (1), and their preparation method through reductive amination reaction in the presence of a reducing agent,

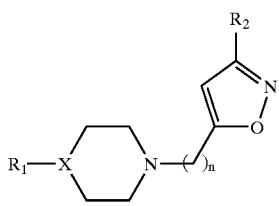

(1)

wherein $R_1$ represents aryl, arylalkyl, diarylalkyl, and heteroaryl, where the aryl groups may have one or more substituents selected from $C_1$–$C_6$ alkyl, $C_1$–$C_6$ alkoxy and a halogen atom, for example, phenylmethyl, diphenylmethyl, (2-trifluoromethylphenyl)methyl, phenyl, 2-methylphenyl, 2-methoxyphenyl, 3-methoxyphenyl, 2-ethoxyphenyl, 2-fluorophenyl, 4-fluorophenyl, 2-chlorophenyl, 4-chlorophenyl, 2-pyrimidyl, 4-chlorobenzhydryl, or 4,4'-difluorobenzhydryl group;

$R_2$ represents aryl, arylalkenyl and heteroaryl group, where the aryl groups may have one or more substituents selected from a halogen atom, nitro, $C_1$–$C_6$ alkyl and $C_1$–$C_6$ alkoxy group, for example, phenyl, 4-fluorophenyl, 4-chlorophenyl, 3-nitrophenyl, 2,4-dimethoxyphenyl, 3,4-dimethoxyphenyl, 3-phenoxyphenyl, styryl, 2-thienyl or 2-thiazol group;

X represents CH or a nitrogen atom; and n represents 3 or 4.

Dopamine is a neurotransmitter found in the brain of animals including human, which is indispensable in the transmission of nerve signals. The dopamine antagonist inhibits the binding of dopamine to dopamine receptor as an antipsychotic, and it is used for the treatment of mental disorder like schizophrenia.

According to recent publications, there are more than one type of dopamine receptors that function through G-protein, and some dopamine antagonists inhibit one type of dopamine receptor preferentially to the others. As the representative dopamine receptors early found, there are $D_1$ receptor that induces the activation of adenylyl cyclase and $D_2$ receptor that inhibits it. Afterwards totally 5 dopamine receptors were found, and they have been classified into two groups: $D_1$ group ($D_1$ and $D_5$) and $D_2$ group ($D_2$, $D_3$ and $D_4$).

Mental disease is related with central dopaminergic nerve system, and central postsynaptic receptor antagonists and presynaptic receptor (autoreceptor) agonists can be used as antipsychotics. Especially the $D_2$ group receptor antagonist haloperidol, a typical antipsychotic, gives extrapyramidal side effect (EPS) in case of long-term treatment. Such side effects occur from hypersensitive reaction due to the long-term inhibition of central dopamine receptor, and include involuntary movement (tardive dyskinesia) and hyperprolactinaemia caused by the inhibition of dopamine receptor at the pituitary gland. On the other hand, the antagonists that selectively act on dopamine $D_3$ or $D_4$ receptors are known to have no side effects like extrapyramidal side effect and tardive dyskinesia.

Accordingly, in the treatment of mental disease like schizophrenia, development of drugs having few side effects, i.e. new compounds that selectively acts on dopamine $D_3$ or $D_4$ receptor is of great importance.

SUMMARY OF THE INVENTION

As a result of the efforts to develop novel chemical compounds that selectively act on dopamine $D_3$ or $D_4$ receptors, the inventors found that novel compounds obtained by introducing various substituents to isoxazolylalkylpiperzaine skeleton have superior and selective antagonistic activity against dopamine $D_3$ or $D_4$ receptors.

Accordingly, the present invention aims at providing novel compounds useful for the treatment of mental disease, their preparation methods thereof and pharmaceutical compositions containing them respectively as effective components.

BRIEF DESCRIPTION OF THE FIGURE

FIG. 1 is the HPLC chromatogram of the compound represented by formula (1) (Compound No. 29).

DETAILED DESCRIPTION OF THE INVENTION

The present invention is characterized by isoxazolylalkylpiperazine derivatives represented by the following formula (1) and their pharmaceutically acceptable addition salts, which have physiological activity on dopamine $D_3$ and $D_4$ receptors,

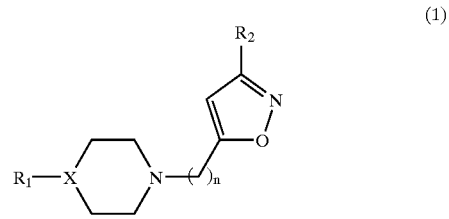

(1)

wherein $R_1$, $R_2$, X and n are the same as defined above.

Isoxazolylalkylpiperazine derivatives according to the present invention represented by formula (1) may have a chiral center, and they can exist as racemates or as mixtures of all possible isomers. Accordingly, the present invention includes racemates, respective isomers and mixture of isomers.

The present invention also includes radioactive isoxazolylalkylpiperazine derivatives represented by formula (1), which are useful for the biological research.

Isoxazolylalkylpiperazine derivatives according to the present invention represented by formula (1) can be used to form pharmaceutically acceptable addition salts through common methods in the art. For example, nontoxic inorganic acids such as hydrochloric acid, hydrobromic acid, sulfuric acid, amidosulfuric acid, phosphoric acid or nitric acid; nontoxic organic acids such as propionic acid, succinic acid, glycolic acid, stearic acid, lactic acid, tartaric acid, citric acid, p-toulenesulfonic acid or methanesulfonic acid; pharmaceutically acceptable addition salts of these acids; or quaternary ammonium salts can be formed.

Hereunder is given a more detailed description about the substituents of isoxazolylalkylpiperazine derivatives of the present invention represented by formula (1). 'Alkyl group' includes linear or branched carbon chains, and its specific examples are methyl, ethyl, propyl, isopropyl, butyl and t-butyl. 'Aryl group' includes a ring having at least 6 atoms, two rings having 10 atoms, or an aromatic ring stabilized by the resonance of the double bond of neighboring carbon atoms, and its specific examples are phenyl and naphthyl. This aryl group may have alkyl, alkoxy or phenoxy group as a substituent. 'Heteroaryl group' includes a single-ring aromatic group containing 5–6 atoms, which has more than one heteroatoms selected from the group consisting of N, O and S. Its specific examples are pyrrole, pyridine, oxazole, thiazole, imidazole, furan and thiophenie. It may have substituent like halogen atom, alkyl, amine and alkylamino group.

In formula (1), it is preferable that $R_1$ is pheylmethyl, diphenylmethyl, phenyl, pyrimidyl or benzimidaoylidinone group, wherein the aromatic ring may have one or more substituents selected from a halogen atom, $C_1$–$C_6$ alkyl, $C_1$–$C_6$ alkoxy; $R_2$ represents phenyl, styryl, phenoxyphenyl, thiazol or thienyl group, wherein the aromatic ring may have one or more substituents selected from a halogen atom, nitro, $C_1$–$C_6$ alkyl and $C_1$–$C_6$ alkoxy; X represents CH or a nitrogen atom; and n represents 3 or 4.

In formula (1), it is more preferable that $R_1$ is hydroxyl, phenylmethyl, diphenylmethyl, (2-trifluoromethylphenyl)methyl, phenyl, 2-methylphenyl, 2-methoxyphenyl, 3-methoxyphenyl, 2-ethoxyphenyl, 2-fluorophenyl, 4-fluorophenyl, 2-chlorophenyl, 4-chlorophenyl, 2-pyrimidyl, 4-chlorobenzhydryl, 4,4'-difluorobenzhydryl, or benzimidazolidinone; $R_2$ represents phenyl, 4-fluorophenyl, 4-chlorophenyl, 3-nitrophenyl, 2,4-dimethoxyphenyl, 3,4-dimethoxyphenyl, 3-phenoxyphenyl, styryl, 2-thienyl or 2-thiazol; X represents CH or a nitrogen atom; and n represents 3 or 4.

Particularly preferable examples of isoxazolylalkylpiperazine derivative represented by formula (1) are as follows:

3-(3-nitrophenyl)-5-[3-(4-phenylpiperazinyl)propyl]isoxazole;

2-{5-[3-(4-phenylpiperazinyl)propyl]isoxazol-3-yl}thiophene;

5-[3-(4-phenylpiperazinyl)propyl]-3-(2-phenylvinyl)isoxazole;

3-(4-chlorophenyl)-5-[3-(4-phenylpiperazinyl)propyl]isoxazole;

3-(4-fluorophenyl)-5-[3-(4-phenylpiperazinyl)propyl]isoxazole;

1-phenoxy-3-{5-[3-(4-phenylpiperazinyl)propyl]isoxazol-3-yl}benzene;

3-phenyl-5-[3-(4-phenylpiperazinyl)propyl]isoxazole;

5-{3-[4-(diphenylmethyl)piperazinyl]propyl}-3-phenylisoxazole;

5-{3-[4-(diphenylmethyl)piperazinyl]propyl}-3-(4-chlorophenyl)isoxazole;

5-{3-[4-(diphenylmethyl)piperazinyl]propyl}-3-(3-nitrophenyl)isoxazole;

4-(5-{3-[4-(diphenylmethyl)piperazinyl]propyl}isozazol-3-yl)-1,2-dimethoxybenzene;

2-(5-{3-[4-diphenylmethyl]piperazinyl}propyl)isoxazol-3-yl}thiophene;

5-{3-[4-(diphenylmethyl)piperazinyl]propyl}-3-(4-fluorophenyl) isoxazole;

1-(5-{3-[4-(diphenylmethyl)piperazinyl]propyl}isoxazol-3-yl)-3-phenoxybenzene;

5-{3-[4-(diphenylmethyl)piperazinyl]propyl}-3-(2-phenylvinyl)isoxazole;

2-methoxy-1-{4-[3-(3-phenylisoxazol-5-yl)propyl]piperazinyl}benzene;

1-(4-{3-[3-(4-chlorophenyl)isoxazol-5-yl]propyl}piperazinyl)2-methoxybenzene;

3-phenyl-5-[3-(4-{[2-(trifluoromethyl)phenyl]methyl}piperazinyl)propyl]isoxazole;

3-(4-chlorophenyl)-5-[3-(4-{[2-(trifluoromethyl)phenyl]methyl}piperazinyl)propyl]isoxazole;

2-methoxy-1-(4-{3-[3-(3-phenoxyphenyl)isoxazol-5-yl]propyl}piperazinyl)benzene;

2-methoxy-1-(4-{3-[3-(2-phenylvinyl)isoxazol-5-yl]propyl}piperazinyl)benzene;

1,2-dimethoxy-(4-{5-[3-(4-phenylpiperazinyl)propyl]isoxazol-3-yl}benzene;

1,2-dimethoxy-4-{5-[3-(4-{[2-(trifluoromethyl)phenyl]methyl}piperazinyl)propyl]isoxazol-3yl}benzene;

1,2-dimethoxy-4-(5-{3-[4-(2-methoxyphenyl)piperazinyl]propyl}isoxazol-3-yl)benzene;

2-methoxy-1-(4-{3-[3-(3-nitrophenyl)isoxazol-5-yl]propyl}piperazinyl)benzene;

3-(3-nitrophenyl)-5-[3-(4-{[2-(trifluoromethyl)phenyl]methyl}piperazinyl)propyl]isoxazole;

2-{5-[3-(4-{[2-(trifluoromethyl)phenyl]methyl}piperazinyl)propyl]isoxazol-3-yl}thiophene;

2-methoxy-1-{4-[3-(3-(2-thienyl)isoxazol-5-yl)propyl]piperazinyl}benzene;

1-(4-{3-[3-(4-fluorophenyl)isoxazol-5-yl]propyl}piperazinyl)-2-methoxybenzene;

5-{3-[4-benzylpiperazinyl]propyl}-3-(2-phenylvinyl)isoxazole;

3-(2-phenylvinyl)-5-[3-(4-{[2-(trifluoromethyl)phenyl]methyl}piperazinyl)propyl]isoxazole;

1-(1-{3-[3-(2-phenylvinyl)isoxazol-5-yl]propyl}-4-piperidyl)-3-hydrobenzimidazol-2-on;

1-(1-{3-[3-(4-chlorophenyl)isoxazol-5-yl]propyl}-4-piperidyl)-3-hydrobenzimidazol-2-on;

1-(1-{3-[3-(3-nitrophenyl)isoxazol-5-yl]propyl}-4-piperidyl)-3-hydrobenzimidazol-2-on;

1-phenoxy-3-{5-[3-(4-{[2-(trifluoromethyl)phenyl]methyl}piperazinyl) propyl]isoxazol-3-yl}benzene;

1-(1-{3-[3-(3,4-dimethoxyphenyl)isoxazol-5-yl]propyl}-4-piperidyl)-3-hydrobenzimidazol-2-on;

1-(1-{3-[3-(4-fluorophenyl)isoxazol-5-yl]propyl}-4-piperidyl)-3-hydrobenzimidazol-2-on;

1-{1-[3-(3-phenylisoxazol-5-yl)propyl]-4-piperidyl}-3-hydrobenzimidazol-2-on;

1-(1-{3-[3-(3-phenoxyphenyl)isoxazol-5-yl]propyl}-4-piperidyl)-3-hydrobenzimidazol-2-on;

2-methoxy-1-{4-[3-(3-(1,3-thiazol-2-yl)isoxazol-5-yl)propyl]piperazinyl}benzene;

2-(5-{3-[4-(diphenylmethyl)piperazinyl]propyl}isoxazol-3-yl)-1,3-thiazole;

3-(4-chlorophenyl)-5-(3-[4-benzylpiperazinyl]propyl) isoxazole;

3-(3-nitrophenyl)-5-{3-[4-benzylpiperazinyl]propyl}isoxazole;

1,2-dimethoxy-4-(5-{3-[4-benzylpiperazinyl]propyl}isoxazol-3-yl)benzene;

2,4-dimethoxy-1-(5-{3-[4-benzylpiperazinyl]propyl}isoxazol-3-yl)benzene;

2-(5-{3-[4-benzylpiperazinyl]propyl}isoxazol-3-yl)thiophene;

2-(5-{3-[4-benzylpiperazinyl]propyl}isoxazol-3-yl)-1,3-thiazole;

3-(4-fluorophenyl)-5-{3-[4-benzylpiperazinyl]propyl}isoxazole;

3-phenyl-5-{3-[4-benzylpiperazinyl]propyl}isoxazole;

1-(5-{3-[4-benzylpiperazinyl]propyl}isoxazol-3-yl)-3-phenoxybenzene;

1-(5-{3-[4-(diphenylmethyl)piperazinyl]propyl}isoxazol-3-yl)-2,4-dimethoxybenzene;

2,4-dimethoxy-1-{5-[3-(4-{[2-(trifluoromethyl)phenyl]methyl}piperazinyl)propyl]isoxazol-3-yl}benzene;

1-(1-{3-[3-(2,4-dimethoxyphenyl)isoxazol-5-yl]propyl}-4-piperidyl)-3-hydrobenzimidazol-2-on;

1-(1-{3-[3-(2-thienyl)isoxazol-5-yl]propyl}-4-piperidyl)-3-hydrobenzimidazol-2-on;

3-(4-fluorophenyl)-5-[3-(4-{[2-(trifluoromethyl)phenyl]methyl}piperazinyl)propyl]isoxazole;

5-{3-[4-(4-fluorophenyl)piperazinyl]propyl}-3-phenylisoxazole;

3-methoxy-1-(4-{3-[3-(3-nitrophenyl)isoxazol-5-yl]propyl}piperazinyl)benzene;

1-(4-{3-[3-(3,4-dimethoxyphenyl)isoxazol-5-yl]propyl}piperazinyl)-3-methoxybenzene;

3-(4-chlorophenyl)-5-{3-[4-(2-chlorophenyl)piperazinyl]propyl}isoxazole;

4-(5-{3-[4-(2-chlorophenyl)piperazinyl]propyl}isoxazol-3-yl)-1,2-dimethybenzene;

2-(5-{3-[4-(2-chlorophenyl)piperazinyl]propyl}isoxazol-3-yl)thiophene;

5-{3-[4-(2-chlorophenyl)piperazinyl]propyl}-3-phenylisoxazole;

1-(5-{3-[4-(2-chlorophenyl)piperazinyl]propyl}isoxazol-3-yl)-3-phenoxybenzene;

1-(4-{3-[3-(3,4-dimethylphenyl)isoxazol-5-yl]propyl}piperazinyl)-2-ethoxybenzene;

2-ethoxy-1-{4-[3-(3-(2-thienyl)isoxazol-5-yl)propyl]piperazinyl}benzene;

2-ethoxy-1-(4-{3-[3-(2-phenylvinyl)isoxazol-5-yl]propyl}piperazinyl)benzene;

5-{4-[4-(diphenylmethyl)piperazinyl]butyl}-3-(4-florophenyl)isoxazole;

5-{4-[4-(diphenylmethyl)piperazinyl]butyl}-3-(3-nitrophenyl)isoxazole;

4-(5-{4-[4-(diphenylmethyl)piperazinyl]butyl}isoxazol-3-yl)-1,2-dimethoxybenzene;

1-(5-{4-[4-(diphenylmethyl)piperazinyl]butyl}isoxazol-3-yl)-2,4-dimethoxybenzene;

5-{4-[4-(diphenylmethyl)piperazinyl]butyl}-3-phenylisoxazole;

2-{5-[4-(4-{[2-(trifluoromethyl)phenyl]methyl}piperazinyl)butyl]isoxazol-3-yl}thiophene;

3-phenyl-5-[4-(4-{[2-(trifluoromethyl)phenyl]methyl}piperazinyl)butyl]isoxazole;

1-(5-{4-[4-(diphenylmethyl)piperazinyl]butyl}isoxazol-3-yl)-3-phenoxybenzene;

5-{4-[4-(diphenylmethyl)piperazinyl]butyl}-3-(2-phenylvinyl)isoxazole;

3-phenoxy-1-{5-[4-(4-{[2-(trifluoromethyl)phenyl]methyl}piperazinyl)butyl]isoxazol-3-yl}benzene;

3-(2-phenylvinyl)-5-[4-(4-{[2-(trifluoromethyl)phenyl]methyl}piperazinyl)butyl]isoxazole;

1,2-dimethoxy-4-{5-[4-(4-{[2-(trifluoromethyl)phenyl]methyl}piperazinyl)butyl]isoxazol-3-yl}benzene;

2,4-dimethoxy-1-{5-[4-(4-{[2-(trifluoromethyl)phenyl]methyl}piperazinyl)butyl]isoxazol-3-yl}benzene;

3-(4-fluorophenyl)-5-[4-(4-{[2-(trifluoromethyl)phenyl]methyl}piperazinyl)butyl]isoxazole;

3-(3-nitrophenyl)-5-[4-(4-{[2-(trifluoromethyl)phenyl]methyl}piperazinyl)butyl]isoxazole;

1-(1-{4-[3-(4-fluorophenyl)isoxazol-5-yl]butyl}-4-piperidyl)-3-hydrobenzimidazol-2-on;

1-(1-{4-[3-(3-nitrophenyl)isoxazol-5-yl]butyl}-4-piperidyl)-3-hydrobenzimidazol-2-on;

1-{1-[4-(3-(2-thienyl)isoxazol-5-yl)butyl]-4-piperidyl}-3-hydrobenzimidazol-2-on;

1-{1-[4-(3-phenylisoxazol-5-yl)butyl]-4-piperidyl-3-hydrobenzimidazol-2-on;

1-(1-{4-[3-(3,4-dimethoxyphenyl)isoxazol-5-yl]butyl}-4-piperidyl)-3-hydrobenzimidazol-2-on;

1,2-dimethoxy-4-(5-{4-[4-benzylpiperazinyl]butyl}isoxazol-3-yl)benzene;

2-(5-{4-[4-(diphenylmethyl)piperazinyl]butyl}isoxazol-3-yl)thiophene;

2-(5-{4-[4-benzylpiperazinyl]butyl}isoxazol-3-yl)thiophene;

1-(5-{4-[4-benzylpiperazinyl]butyl}isoxazol-3-yl)-3-phenoxybenzene;

5-{4-[4-benzylpiperazinyl]butyl}-3-(2-phenylvinyl)isoxazole;

1-(1-{4-[3-(3-phenoxyphenyl)isoxazol-5-yl]butyl}-4-piperidyl)-3-hydrobenzimidazol-2-on;

1-(1-{4-[3-(2-phenylvinyl)isoxazol-5-yl]butyl}-4-piperidyl)-3- hydrobenzimidazol-2-on;

3-(4-fluorophenyl)-5-{4-[4-benzylpiperazinyl]butyl}isoxazole;

3-(3-nitrophenyl)-5-{4-[4-benzylpiperazinyl]butyl}isoxazole;

2,4-dimethoxy-1-(5-{4-[4-benzylpiperazinyl]butyl}isoxazol-3-yl)benzene;

1-(1-{4-[3-(2,4-dimethoxyphenyl)isoxazol-5-yl]butyl}-4-piperidyl)-3-hydrobenzimidazol-2-on;

3-phenyl-5-{4-[4-benzylpiperazinyl]butyl}isoxazole;

3-(4-fluorophenyl)-5-[4-(4-phenylpiperazinyl)butyl]isoxazole;

3-(3-nitrophenyl)-5-[4-(4-phenylpiperazinyl)butyl]isoxazole;

1,2-dimethoxy-4-{5-[4-(4-phenylpiperazinyl)butyl]isoxazol-3-yl}benzene;

2,4-dimethoxy-1-{5-[4-(4-phenylpiperazinyl)butyl]isoxazol-3-yl}benzene;

2-{5-[4-(4-phenylpiperazinyl)butyl]isoxazol-3-yl}thiophene;

3-Phenyl-5-[4-(4-phenylpiperazinyl)butyl]isoxazole;

1-(4-{4-[3-(4-fluorophenyl)isoxazol-5-yl]butyl}piperazinyl)-2-methoxybenzene;

2-methoxy-1-(4-{4-[3-(3-nitrophenyl)isoxazol-5-yl]butyl}piperazinyl)benzene;

1-(4-{4-[3-(3,4-dimethoxyphenyl)isoxazol-5-yl]butyl}piperazinyl)-2-methoxybenzene;

1-(4-{4-[3-(2,4-dimethoxyphenyl)isoxazol-5-yl]butyl}piperazinyl)-2-methoxybenzene;

2-methoxy-1-{4-(3-(2-thienyl)isoxazol-5-yl)butyl}piperazinyl}benzene;
2-methoxy-1-{4-[4-(3-phenylisoxazol-5-yl)butyl]piperazinyl}benzene;
3-phenoxy-1-{5-[4-(4-phenylpiperazinyl)butyl]isoxazol-3-yl}benzene;
5-[4-(4-phenylpiperazinyl)butyl]-3-(2-phenylvinyl)isoxazole;
1-(5-{4-[4-(2-methoxyphenyl)piperazinyl]butyl}isoxazol-3-yl)-3-phenoxybenzene;
2-methoxy-1-(4-{4-[3-(2-phenylvinyl)isoxazol-5-yl]butyl}piperazinly)benzene;
3-(4-fluorophenyl)-5-{4-[4-(4-fluorophenyl)piperazinyl]butyl}isoxazole;
3-methoxy-1-(4-{4-[3-(3-nitrophenyl)isoxazol-5-yl]butyl}piperazinly)benzene;
5-{4-[4-(2-fluorophenyl)piperazinyl]butyl}-3-(2-phenylvinyl)isoxazole;
1,2-dimethoxy-4-(5-{4-[4-(2-methylphenyl)piperazinyl]butyl}isoxazol-3-yl)benzene; and
pharmaceutically acceptable addition salts thereof.

The present invention also includes a preparation method of isoxazolylalkylpiperazine derivative represented by formula (1), which can be illustrated by the following Scheme 1, Scheme 1

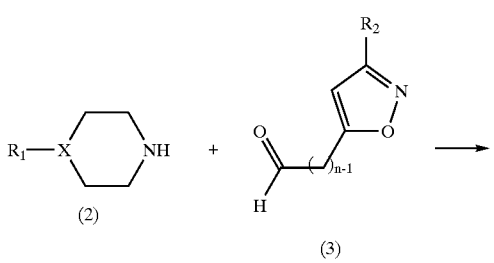

(1)

wherein $R_1$, $R_2$, X and n are the same as defined in formula (1).

As shown in Scheme 1, amine compound represented by formula (2) is reacted with aldehyde compound in the presence of a reducing agent via amination reaction to obtain the compound represented by formula (1). The reductive amination reaction of the present invention is performed under a nitrogen atmosphere and at room temperature. Molecular sieve (4A, beads, 4–8 mesh) was used in the reaction, and 1–3 equivalents of glacial acetic acid may be added when the reactivity of the starting material is unsatisfactory. As the reducing agent for the imine formed by the condensation reaction of amine and aldehyde, NaBH(OAc)$_3$, NaBH$_3$CN or NaBH$_4$ may be used, and its dosage is 2–10 equivalents depending on the reactivity and 2–3 equivalents are desirable. Common organic solvents can be used for the reaction solvent, and its specific examples are tetrahydrofuran, 1,2-dichloroethane, acetonitrile and methylene chloride. In the Examples of the present invention, mainly methylene chloride was used. The reaction time is 3–24 hr, and 12–14 hr is desirable. The reaction progress is traced using thin-layer chromatography (TLC). When the reaction is completed, saturated aqueous NaHCO$_3$ solution is added and the reactant is extracted with suitable organic solvent. As the extraction solvent, ether, methylene chloride and ethyl acetate can be used, and methylene chloride is best recommended.

The pharmaceutically acceptable addition salt of the compound represented by formula (1) can be easily prepared using common preparation methods reported in the literature, and can be purified without a special purification process. Hereunder is given a preparation method of a pharmaceutically acceptable addition salt of the compound represented by formula (1), attaching importance on the preparation process of a hydrochloric acid salt. After drying and evaporating the said extraction solvent, the residue is dissolved in small amount of ether followed by the addition of 1–10 equivalents of HCl ether solution to obtain a hydrochloric acid salt of the target compound in white solid form. As the solvent used in the preparation of HCl solution, chloroform, methylene chloride, ether, methanol, ethyl acetate or their mixture can be used, and ether is desirable. The product formed in white solid form can be separated by a centrifuge or a simple solvent removing device using cotton. After washing the solid 2–3 times with 1–2 mL of ether, it is dried to yield a hydrochloric acid salt as white solid with high purity.

Amine compound represented by formula (2), which is used as a starting material of the preparation method of the present invention, can be easily prepared by the methods reported in the literature. Aldehyde compound represented by formula (3), which is used as another starting material of the preparation method of the present invention, also can be easily prepared by the methods reported in the literature. The synthetic process can be illustrated by the following Scheme 2, Scheme 2

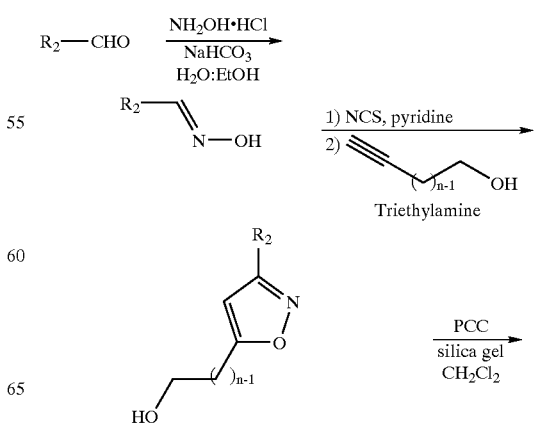

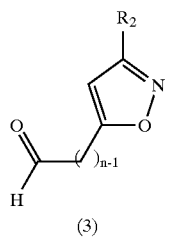

(3)

wherein $R_2$ and n are the same as defined in formula (1).

Since the isoxazolylalkylpiperazine derivative according to the present invention, which is represented by formula (1), is very effective in the treatment of mental disease, the present invention includes the pharmaceutical compositions and the dopaminergic antagonists containing the novel compound represented by formula (1) as the effective component. The pharmaceutical compositions and the dopaminergic antagonists can be prepared in common oral or non-oral preparation form like tablets, capsules, troches, liquids and emulsions by adding common nontoxic pharmaceutically acceptable carrier, reinforcing agent and filler. The administration dosage of the compound represented by formula (1) depends on the age, weight, sex, administration type, health condition and disease progress of the patient, and for an adult patient with 70 kg of weight, the general dosage is 0.01–400 mg/day. It can be administered once a day or separately according to the direction of the doctor or pharmacist.

Hereunder is given a more detailed description of the present invention. However it should not be construed as limiting the scope of the present invention.

The following Comparative Examples are exemplary preparation methods of the amine compound represented by formula (2) and the aldehyde compound represented by formula (3), which are used as starting materials of the present invention.

COMPARATIVE EXAMPLE 1

Preparation of Hydroxyiminomethyl-3-nitrobenzene

3-Nitrobenzaldehyde (3.00 g, 19.9 mmol) and hydroxyamine HCl (1.79 g, 25.8 mmol) were dissolved in 60 mL of ethyl alcohol/water (1/1, v/v) solution. While stirring the reaction mixture, $Na_2CO_3$ (2.74 g, 25.8 mmol) was added slowly at below 0. The reaction was continued for 1 hr in an oil bath preheated to 60–65. After the reaction was completed, 3.0 g (92%) of the target product was obtained by extracting with ethyl acetate, drying over anhydrous $MgSO_4$ and removing the solvent under reduced pressure.

$^1$H NMR (300 MHz, $CDCl_3$) 7.58 (t, 1H, J=7.95 Hz), 7.92 (d, 1H, J=7.68 Hz), 8.25 (overlap), 8.42 (s, 1H).

COMPARATIVE 2

Preparation of 3-[3-(3-Nitrophenyl)isoxazol-5-yl]propan-1-ol

Hydroxyiminomthyl-3-nitrobenzene (2.00 g, 12.0 mmol), N-chlorosuccinimide (1.93 g, 14.4 mmol) and pyridine (0.097 mL, 1.2 mmol) were dissolved in 30 mL of dry tetrahydrofuran under $N_2$. After stirring the reaction mixture for 30 min at room temperature, 4-pentene-1-ol (1.68 mL, 18.1 mmol) and triethylamine (2.01 mL, 14.4 mmol) dissolved in 2 mL of tetrahydrofuran were added. Then, the reaction was continued for 1 hr at 50. When the reaction was completed, it was extracted with ethyl acetate and washed with saturated sodium chloride solution. After drying the organic layer over anhydrous $MgSO_4$, the crude product was purified by column chromatography on silica gel to obtain 1.0 g (34%) of the target compound.

$^1$H NMR (300 MHz, $CDCl_3$) 2.05 (m, 2H), 2.98 (t, 2H, J=7.68 Hz), 3.78 (t, 2H, J=6.09 Hz), 6.43 (s, 1H), 7.65 (t, 1H, J=8.19 Hz), 8.18 (d, 1H), 8.31 (d, 1H), 8.62 (s, 1H).

COMPARATIVE EXAMPLE 3

Preparation of 3-[3-(3-Nitrophenyl)isoxazol-5-yl]propanaldehyde

3-[3-(3-nitrophenyl)isoxazol-5-yl]propan-1-ol (1.02 g, 4.1 mmol), sodium acetate (0.10 g, 1.3 mmol), and pyridinium chlorochromate (1.77 g, 8.2 mmol) were added in 30 mL of dry methylene chloride. After the reaction was continued for 4 hr at an ambient temperature, diethyl ether was added and the reaction mixture was filtered through a cellite bed. 0.6 g (64%) of the target compound was obtained by removing all the solvent and purifying by column chromatography on silica gel.

$^1$H NMR (300 MHz, $CDCl_3$) 3.01 (t, 2H), 3.20 (t, 2H), 6.43 (s, 1H), 7.65 (t, 1H), 8.17 (d, 1H), 8.32 (d, 1H), 8.60 (s, 1H), 9.88 (s, 1H).

The following Examples are preparation examples of the compound represented by Formula (1) or its pharmaceutically acceptable addition salt.

EXAMPLE 1

Preparation of 3-(3-Nitrophenyl)-5-[3-(4-phenylpiperazinyl)propyl]isoxazole

About 3 min after dissolving 3-[3-(3-nitrophenyl)isoxazol-5-yl]propanal (20 mg, 0.09 mmol) and 1-phenylpiperazine (13.4, 0.09 mmol) in 2 mL of dry methylene chloride, were added $NaBH(OAc)_3$ (56 mg, 0.26 mmol) and molecular sieves (5 beads). After the reaction was carried out for about 22 hr, the reaction mixture was diluted with ethyl acetate and washed with saturated $NaHCO_3$ solution saturated sodium chloride solution. After drying the organic layer over anhydrous $MgSO_4$, the solvent was removed under reduced pressure. After dissolving the residue with 1 mL of diethyl ether, HCl ether solution was slowly dropped to precipitate a white hydrochloric acid salt which was collected by filtration or centrifugation, and it was washed several times with diethyl ether. After drying the same under reduced pressure, was obtained 18.1 mg (56.8%) of the target compound.

$^1$H NMR (300 MHz, $CDCl_3$) 1.99 (m, 2H), 2.52 (m, 2H), 2.66 (t, 4H, J=5.16 Hz), 2.86 (t, 2H, J=7.41 Hz), 3.24 (t, 4H, J=4.89 Hz), 6.27(s, 1H), 6.91 (m, 3H), 7.12 (m, 2H), 7.31 (m, 5H), 7.52 (d, 2H, J=7.08 Hz).

EXAMPLE 2

Preparation of 2-{5-[3-(4-Phenylpiperazinyl)propyl]isoxazol-3-yl}thiophene

About 2 min after dissolving 3-[3-(2-thienyl)isoxazol-5-yl]propanal (20 mg, 0.1 mmol), 1-phenylpiperazine (14.7, 0.1 mmol) in 2 mL of dry methylene chloride, were added $NaBH(OAc)_3$ (61.4 mg, 0.3 mmol) and molecular sieves (5 beads). The reaction mixture was reacted for 3.5 hr and followed the same processes as in Example 1 to obtain 26.4 mg (77.4%) of the target compound.

¹H NMR (300 MHz, CDCl₃) 1.99 (m, 2H), 2.51 (m, 2H), 2.65 (t, 4H, J=5.16 Hz), 2.86 (m, 2H), 3.23 (t, 4H, J=4.95 Hz), 6.27 (s, 1H), 6.89 (m, 3H), 7.13 (m, 2H), 7.28 (m, 2H), 7.42 (m, 1H).

EXAMPLE 3

Preparation of 5-[3-(4-Phenylpiperazinyl)propyl]-3-(2-phenylvinyl)isoxazole

About 2 min after dissolving 3-[3-(2-phenylvinyl)isoxazol-5-yl]propanal (20 mg, 0.09 mmol) and 1-phenylpiperazine (13.4, 0.09 mmol) in 2 mL of dry methylene chloride, were added NaBH(OAc)₃ (56 mg, 0.26 mmol) and molecular sieves (5 beads). The reaction mixture was reacted for 22 hr and followed the same processes as in Example 1 to obtain 16.2 mg (49.3%) of the target compound.

¹H NMR (300 MHz, CDCl₃) 1.99 (m, 2H), 2.52 (m, 2H), 2.66 (t, 4H, J=5.16 Hz), 2.86 (t, 2H, J=7.41 Hz), 3.24 (t, 4H, J=4.89 Hz), 6.27 (s, 1H), 6.91 (m, 3H), 7.12 (m, 2H), 7.31 (m, 5H), 7.52 (d, 2H, J=7.08 Hz).

EXAMPLE 4

Preparation of 3-(4-Chlorophenyl)-5-[3-(4-phenylpiperazinyl)propyl]isoxazole

About 2 min after dissolving 3-[3-(2-chlorophenyl)isoxazol-5-yl]propanal (15.8 mg, 0.09 mmol) and 1-phenylpiperazine (13.4, 0.07 mmol) in 2 mL of dry methylene chloride, were added NaBH(OAc)₃ (42.6 mg, 0.2 mmol) and molecular sieves (5 beads). The reaction mixture was reacted for 36 hr and followed the same processes as in Example 1 to obtain 17.9 mg (70.0%) of the target compound.

¹H NMR (300 MHz, CDCl₃) 1.99 (m, 2H), 2.49 (m, 2H), 2.65 (t, 4H, J=5.22 Hz), 2.86 (m, 2H), 3.23 (t, 4H, J=4.98 Hz), 6.31 (s, 1H), 6.89 (m, 3H), 7.25 (m, 2H), 7.42 (m, 2H), 7.72 (m, 2H).

EXAMPLE 5

Preparation of 3-(4-Fluorophenyl)-5-[3-(4-phenylpiperazinyl)propyl]isoxazole

About 2 min after dissolving 3-[3-(2-fluorophenyl)isoxazol-5-yl]propanal (20 mg, 0.09 mmol) and 1-phenylpiperazine (13.9, 0.09 mmol) in 2 mL of dry methylene chloride, were added NaBH(OAc)₃ (58 mg, 0.27 mmol) and molecular sieves (5 beads). The reaction mixture was reacted for 16 hr and followed the same processes as in Example 1 to obtain 38.1 mg (95.4%) of the target compound.

¹H NMR (300 MHz, CDCl₃) 1.99 (m, 2H), 2.51 (t, 2H, J=6.96 Hz), 2.65 (t, 4H, J=5.22 Hz), 2.88 (t, 2H, J=7.65 Hz), 3.23 (t, 4H, J=4.92 Hz), 6.29 (s, 1H), 6.88 (m, 3H), 7.12 (m, 2H), 7.25 (m, 2H), 7.78 (m, 2H).

EXAMPLE 6

Preparation of 1-Phenoxy-3-{5-[3-(4-phenylpiperazinyl)propyl]isoxazol-3-yl}benzene About 2 min after dissolving 3-[3-(3-phenoxyphenyl)isoxazol-5-yl]propanal (20 mg, 0.07 mmol) and 1-phenylpiperazine (10.4, 0.07 mmol) in 2 mL of dry methylene chloride, were added NaBH(OAc)₃ (43.4 mg, 0.2 mmol) and molecular sieves (5 beads). The reaction mixture was reacted for 16 hr and followed the same processes as in Example 1 to obtain 39.2 mg (100%) of the target compound.

¹H NMR (300 MHz, CDCl₃) 1.99 (m, 2H), 2.51 (t, 2H, J=6.93 Hz), 2.65 (m, 4H), 2.87 (t, 2H, J=7.41 Hz), 3.23 (m, 4H), 6.29 (s, 1H), 6.89 (m, 3H), 7.11 (m, 4H), 7.34 (m, 6H), 7.54 (m, 1H); ¹³C NMR (150 MHz, CDCl₃) 25.29, 49.61, 53.76, 57.93, 99.88, 116.82, 117.68. 119.75, 120.53, 120.81, 122.24, 124.29, 129.80, 130.56, 130.92, 131.72, 151.83, 158.51, 162.61, 174.32.

EXAMPLE 7

Preparation of 3-Phenyl-5-[3-(4-phenylpiperazinyl)propyl]isoxazole

About 2 min after dissolving 3-(3-phenylisoxazol-5-yl)propanal (10 mg, 0.05 mmol) and 1-phenylpiperazine (7.6, 0.05 mmol) in 2 mL of dry methylene chloride, were added NaBH(OAc)₃ (32 mg, 0. 15 mmol) and molecular sieves (5 beads). The reaction mixture was reacted for 16 hr and followed the same processes as in Example 1 to obtain 11.7 mg (67.3%) of the target compound.

¹H NMR (300 MHz, CDCl₃) 2.02 (m, 2H), 2.53 (t, 2H, J=6.99 Hz), 2.15 (m, 4H), 2.89 (m, 2H), 3.25 (m, 2H), 6.34 (s, 1H), 6.92 (m, 3H), 7.28 (m, 2H), 7.45 (m, 3H), 7.79 (m, 2H).

EXAMPLE 8

Preparation of 5-{3-[4-(Diphenylmethyl)piperazinyl]propyl}-3-phenylisoxazole

About 2 min after dissolving 3-(3-phenylisoxazol-5-yl)propanal (10 mg, 0.05 mmol) and 1-(diphenylmethyl)piperazine (13 mg, 0.05 mmol) in 2 mL of dry methylene chloride, were added NaBH(OAc)₃ (32 mg, 0.15 mmol) and molecular sieves (5 beads). The reaction mixture was reacted for 2.75 hr and followed the same processes as in Example 1 to obtain 12.5 mg (57.1%) of the target compound.

¹H NMR (300 MHz, CDCl₃) 1.98 (m, 2H), 2.50 (m, 10H), 2.84 (m, 2H), 4.24 (s, 1H), 6.32 (s, 1H), 7.19 (m, 2H), 7.25 (m, 4H), 7.41 (m, 7H), 7.78 (m, 2H).

EXAMPLE 9

Preparation of 5-{3-[4-(Diphenylmethyl)piperazinyl]propyl}-3-(4-chlorophenyl)isoxazole About 2 min after dissolving 3-[3-(4-chlorophenyl)isoxazol-5-yl]propanal (10 mg, 0.05 mmol) and 1-(diphenylmethyl)piperazine (11 mg, 0.04 mmol) in 2 mL of dry methylene chloride, were added NaBH(OAc)₃ (27 mg, 0.13 mmol) and molecular sieves (5 beads). The reaction mixture was reacted for 2.75 hr and followed the same processes as in Example 1 to obtain 18 mg (90.8%) of the target compound.

¹H NMR (300 MHz, CDCl₃) 1.98 (m, 2H), 2.52 (m, 10H), 2.84 (t, 2H, J=7.47 Hz), 4.24 (s, 1H), 6.30 (s, 1H), 7.19 (m, 1H), 7.27 (m, 4H), 7.42 (m, 7H), 7.72 (m, 2H).

EXAMPLE 10

Preparation of 5-{3-[4-(Diphenylmethyl)piperazinyl]propyl}-3-(3-nitrophenyl)isoxazole About 2 min after dissolving 3-[3-(3-nitrophenyl)isoxazol-5-yl]propanal (10 mg, 0.04 mmol) and 1-(diphenylmethyl)piperazine (10 mg, 0.04 mmol) in 2 mL of dry methylene chloride, were added NaBH(OAc)$_3$ (26 mg, 0.12 mmol) and molecular sieves (5 beads). The reaction mixture was reacted for 18.2 hr and followed the same processes as in Example 1 to obtain 17.6 mg (89.8%) of the target compound.

$^1$H NMR (300 MHz, CDCl$_3$) 2.0 (m, 2H), 2.51 (m, 10H), 2.88 (t, 2H, J=7.41 Hz), 4.24 (s, 1H), 6.42 (s, 1H), 7.18 (m, 2H), 7.27 (t, 4H, J=7.68 Hz), 7.40 (t, 4H, J=1.47 Hz), 7.64 (t, 1H, J=7.95 Hz), 8.16 (d, 1H, J=7.68 Hz), 8.30 (d, 1H), 8.60 (t, 1H, J=1.77 Hz).

EXAMPLE 11

Preparation of 4-(5-{3-[4-(Diphenylmethyl)piperazinyl]propyl}isoxazol-3-yl)-1,2-dimethoxybenzene About 2 min after dissolving 3-[3-(3,4-dimethoxyphenyl)isoxazol-5-yl]propanal (10 mg, 0.04 mmol) and 1-(diphenylmethyl)piperazine (10 mg, 0.04 mmol) in 2 mL of dry methylene chloride, were added NaBH(OAc)$_3$ (24 mg, 0.12 mmol) and molecular sieves (5 beads). The reaction mixture was reacted for 18.2 hr and followed the same processes as in Example 1 to obtain 18.4 mg (96.5%) of the target compound.

$^1$H NMR (300 MHz, CDCl$_3$) 1.94 (m, 2H), 2.49 (m, 10H), 2.82 (t, 2H), 3.93 (m, 6H), 4.22 (s, 1H), 6.26 (s, 1H), 6.91 (m, 1H), 7.18 (m, 2H), 7.25 (m, 5H), 7.41 (m, 5H).

EXAMPLE 12

Preparation of 2-(5-{3-[4-(Diphenylmethyl)piperazinyl]propyl}isoxazol-3-yl)thiophene About 2 min after dissolving 3-(3-(2-thienyl)isoxazol-5-yl)propanal (10 mg, 0.05 mmol) and 1-(diphenylmethyl)piperazine (12 mg, 0.05 mmol) in 2 mL of dry methylene chloride, were added NaBH(OAc)$_3$ (31 mg, 0.14 mmol) and molecular sieves (5 beads). The reaction mixture was reacted for 4.2 hr and followed the same processes as in Example 1 to obtain 15.8 mg (74.2%) of the target compound.

$^1$H NMR (300 MHz, CDCl$_3$) 1.94 (m, 2H), 2.45 (m, 10H), 2.82 (t, 2H, J=7.29 Hz), 4.23 (s, 1H), 6.24 (s, 1H), 7.10 (t, 1H, J=1.62 Hz), 7.18 (m, 2H), 7.27 (m, 5H), 7.42 (m, 5H).

EXAMPLE 13

Preparation of 5-{3-[4-(Diphenylmethyl)piperazinyl]propyl}-3-(4-fluorophenyl)isoxazole About 2 min after dissolving 3-[3-(4-fluoromethyl)isoxazol-5-yl]propanal (10 mg, 0.05 mmol) and (1-dimethylphenyl)piperazine (11.5 mg, 0.05 mmol) in 2 mL of dry methylene chloride, were added NaBH(OAc)$_3$ (29 mg, 0.14 mmol) and molecular sieves (5 beads). The reaction mixture was reacted for 3.8 hr and followed the same processes as in Example 1 to obtain 17.1 mg (82.3%) of the target compound.

$^1$H NMR (300 MHz, CDCl$_3$) 1.98 (m, 2H), 2.52 (m, 10H), 2.84 (t, 2H, J=7.65 Hz), 4.24 (s, 1H), 6.29 (s, 1H), 7.13 (m, 2H), 7.29 (m, 5H), 7.41 (m, 5H), 7.77 (m, 2H).

EXAMPLE 14

Preparation of 1-(5-{3-[4-(Diphenylmethyl)piperazinyl]propyl}isoxazol-3-yl)-3-phenoxybenzene About 2 min after dissolving 3-[3-(3-phenoxyphenyl)isoxazol-5-yl]propanal (10 mg, 0.03 mmol) and (1-dimethylphenyl)piperazine (8.6 mg, 0.03 mmol) in 2 mL of dry methylene chloride, were added NaBH(OAc)$_3$ (21.7 mg, 0.10 mmol) and molecular sieves (5 beads). The reaction mixture was reacted for 5.15 hr and followed the same processes as in Example 1 to obtain 13 mg (72.0%) of the target compound.

$^1$H NMR (300 MHz, CDCl$_3$) 1.93 (m, 2H), 2.45 (m, 10H), 2.82 (t, 2H, J=7.44 Hz), 4.22 (s, 1H), 6.25 (s, 1H), 7.25 (m, H), 7.50 (d, 1H).

EXAMPLE 15

Preparation of 5-{3-[4-(Diphenylmethyl)piperazinyl]propyl}-3-(2-phenylvinyl)isoxazole About 2 min after dissolving 3-[3-(2-phenylvinyl)isoxazol-5-yl]propanal (10 mg, 0.04 mmol) and (1-dimethylphenyl)piperazine (11 mg, 0.04 mmol) in 2 mL of dry methylene chloride, were added NaBH(OAc)$_3$ (28 mg, 0.13 mmol) and molecular sieves (5 beads). The reaction mixture was reacted for 4.75 hr and followed the same processes as in Example 1 to obtain 14.3 mg (70.14%) of the target compound.

$^1$H NMR (300 MHz, CDCl$_3$) 1.94 (m, 2H), 2.48 (m, 10H), 2.80 (t, 2H, J=7.5 Hz), 4.24 (s, 1H), 6.25 (s, 1H), 7.18 (m, 3H), 7.30 (m, 12H), 7.52 (d, 2H, J=6.69 Hz).

EXAMPLE 16

Preparation of 2-Methoxy-1-{4-[3-(3-phenylisoxazol-5-yl)propyl]piperazinyl}benzene About 2 min after dissolving 3-(3-phenylisoxazol-5-yl)propanal (10 mg, 0.05 mmol) and 1-(2-methoxyphenyl)piperazine (19.2 mg, 0.10 mmol) in 2 mL of dry methylene chloride, were added NaBH(OAc)$_3$ (32 mg, 0.15 mmol) and molecular sieves (5 beads). The reaction mixture was reacted for 16.5 hr and followed the same processes as in Example 1 to obtain 10 mg (53.0%) of the target compound.

$^1$H NMR (300 MHz, CDCl3) 2.02 (m, 2H), 2.55 (t, 2H, J=6.93 Hz), 2.71 (br s, 4H), 2.89 (t, 2H, J=7.50 Hz), 3.13 (br s, 4H), 3.87 (s, 3H), 6.34 (s, 1H), 6.94 (m, 4H), 7.42 (m, 3H), 7.80 (m, 2H); $^{13}$C NMR (150 MHz, CDCl$_3$) 25.05, 25.34, 30.36, 50.86, 53.99, 56.07. 58.06. 99.83, 112.00, 119.03, 121.75, 123.79, 127.45, 129.55, 130.04, 130.53, 152.99, 163.12.

EXAMPLE 17

Preparation of 1-(4-{3-[3-(4-Chlorophenyl)isoxazol-5-yl]propyl}piperazinyl)-2-methoxybenzene About 2 min after dissolving 3-[3-(4-chlorophenyl)isoxazol-5-yl]propanal (10 mg, 0.04 mmol) and 1-(2-methoxyphenyl)piperazine (16.2 mg, 0.08 mmol) in 2 mL of dry methylene chloride, were added NaBH(OAc)$_3$ (26.7 mg, 0.13 mmol) and molecular sieves (5 beads). The reaction mixture was reacted for 16.5 hr and followed the same processes as in Example 1 to obtain 16.7 mg (96.5%) of the target compound.

$^1$H NMR (300 MHz, CDCl$_3$) 2.02 (m, 2H), 2.56 (t, 2H, J=6.93 Hz), 2.73 (br s, 4H), 2.89 (t, 2H, J=7.62 Hz), 3.14 (br s, 4H), 3.87 (s, 3H), 6.32 (s, 1H), 6.93 (m, 4H), 7.43 (d, 2H, J=8.46 Hz), 7.73 (d, 2H, J=8.31 Hz); $^{13}$C NMR (300 MHz, CDCl$_3$) 25.03, 25.31, 30.36, 50.86, 53.97, 56.07, 58.01, 99.72, 112.00, 119.03, 121.75, 123.82, 128.51, 128.72, 129.83, 136.54, 141.70, 152.97, 162.14.

EXAMPLE 18

Preparation of 3-Phenyl-5-[3-(4-{[2-(trifluoromethyl)phenyl]methyl}piperazinyl)propyl]isoxazole About 2 min after dissolving 3-(3-phenylisoxazol-5-yl)propanal (10 mg, 0.05 mmol) and 1-[2-(trifluoromethyl)

benyl]piperazine (10.4, 0.05 mmol) in 2 mL of dry methylene chloride, were added NaBH(OAc)$_3$ (32 mg, 0.15 mmol) and molecular sieves (5 beads). The reaction mixture was reacted for 2.1 hr and followed the same processes as in Example 1 to obtain 10 mg (46.6%) of the target compound.

$^1$H NMR (300 MHz, CDCl$_3$) 1.96 (m, 2H), 2.50 (t, 2H, J=7.08 Hz), 2.56 (br s, 8H), 2.86 (t, 2H, J=7.41 Hz), 3.68 (s, 2H), 6.33 (s, 1H), 7.33 (t, 1H), 7.47 (m, 4H), 7.62 (d, 1H), 7.78 (m, 3H).

EXAMPLE 19

Preparation of 3-(4-Chlorophenyl)-5-[3-(4-{[2-(trifluoromethyl)phenyl]methyl}piperazinyl)propyl]isoxazole About 2 min after dissolving 3-(3-phenylisoxazol-5-yl)propanal (10 mg, 0.05 mmol) and 1-[2-(trifluoromethyl)benyl]piperazine (10.4, 0.04 mmol) in 2 mL of dry methylene chloride, were added NaBH(OAc)$_3$ (26.7 mg, 0.13 mmol) and molecular sieves (5 beads). The reaction mixture was reacted for 18.5 hr and followed the same processes as in Example 1 to obtain 18.4 mg (94.4%) of the target compound.

$^1$H NMR (300 MHz, CDCl$_3$) 1.97 (m, 2H), 2.50 (m, 10H), 2.86 (t, 2H, J=7.44 Hz), 3.68 (s, 2H), 6.31 (s, 1H), 7.33 (t, 1H), 7.43 (d, 2H), 7.51 (t, 1H), 7.75 (m, 3H).

EXAMPLE 20

Preparation of 2-Methoxy-1-(4-{3-[3-(3-phenoxyphenyl)isoxazol-5-yl]propyl}piperazinyl)benzene About 2 min after dissolving 3-[3-(3-phenoxyphenyl)isoxazol-5-yl]propanal (10 mg, 0.03 mmol) and 1-(2-methoxyphenyl)piperazine (13.2 mg, 0.07 mmol) in 2 mL of dry methylene chloride, were added NaBH(OAc)$_3$ (22 mg, 0.10 mmol) and molecular sieves (5 beads). The reaction mixture was reacted for 18.5 hr and followed the same processes as in Example 1 to obtain 11.5 mg (71.8%) of the target compound.

$^1$H NMR (300 MHz, CDCl$_3$) 2.02 (m, 2H), 2.56 (t, 2H, J=7.44 Hz), 2.74 (br s, 4H), 2.88 (t, 2H, J=7.62 Hz), 3.16 (br s, 4H), 3.87 (s, 3H), 6.30 (s, 1H), 6.88 (d, 1H), 7.02 (m, 7H), 7.35 (m, 4H), 7.52 (d, 1H).

EXAMPLE 21

Preparation of 2-Methoxy-1-(4-{3-[3-(2-phenylvinyl)isoxazol-5-yl]propyl}piperazinyl)benzene About 2 min after dissolving 3-[3-(2-phenylvinyl)isoxazol-5-yl]propanal (10 mg, 0.04 mmol) and 1-(2-methoxyphenyl)piperazine (17 mg, 0.09 mmol) in 2 mL of dry methylene chloride, were added NaBH(OAc)$_3$ (28 mg, 0.13 mmol) and molecular sieves (5 beads). The reaction mixture was reacted for 18.5 hr and followed the same processes as in Example 1 to obtain 9.5 mg (53.5%) of the target compound.

$^1$H NMR (300 MHz, CDCl$_3$) 1.99 (m, 2H), 2.5 (m, 10H), 2.86 (t, 2H, J=7.41 Hz), 3.68 (s, 2H), 6.33 (d, 1H), 7.33 (t, 1H), 7.48 (m, 4H), 7.63 (d, 1H, J=7.41 Hz), 7.80 (m, 3H).

EXAMPLE 22

Preparation of 1,2-Dimethoxy-4-{5-[3-(4-phenylpiperazinyl)propyl]isoxazol-3-yl}benzene About 2 min after dissolving 3-[3-(3,4-dimethoxyphenyl)isoxazol-5-yl]propanal (10 mg, 0.04 mmol) and 1-phenylpiperazine (5.9, 0.04 mmol) in 2 mL of dry methylene chloride, were added NaBH(OAc)$_3$ (24 mg, 0.12 mmol) and molecular sieves (5 beads). The reaction mixture was reacted for 26.55 hr and followed the same processes as in Example 1 to obtain 14.7 mg (100%) of the target compound.

$^1$H NMR (300 MHz, CDCl$_3$) 2.01 (m, 2H), 2.53 (t, 2H, J=7.62 Hz), 2.67 (t, 4H, J=5.16 Hz), 2.88 (t, 2H, J=7.44 Hz), 3.24 (t, 4H, J=4.74 Hz), 3.93 (m, 6H), 6.30 (s, 1H), 6.89 (m, 4H), 7.27 (t, 3H), 7.41 (s, 1H).

EXAMPLE 23

Preparation of 1,2-Dimethoxy-4-{5-[3-(4-{[2-(trifluoromethyl)phenyl]methyl}piperazinyl)propyl]isoxazol-3-yl}benzene About 2 min after dissolving 3-[3-(3,4-dimethoxyphenyl)isoxazol-5-yl]propanal (10 mg, 0.04 mmol) and 1-[2-(trifluoromethyl)benzyl]piperazine (8.0, 0.04 mmol) in 2 mL of dry methylene chloride, were added NaBH(OAc)$_3$ (24 mg, 0.12 mmol) and molecular sieves (5 beads). The reaction mixture was reacted for 22.5 hr and followed the same processes as in Example 1 to obtain 12.3 mg (65.6%) of the target compound.

$^1$H NMR (300 MHz, CDCl$_3$) 1.97 (m, 2H), 2.53 (m, 10H), 2.84 (t, 2H, J=7.44 Hz), 3.67 (s, 2H), 3.93 (m, 6H), 6.28 (s, 1H), 6.91 (d, 1H, J=8.37 Hz), 7.27 (d, 1H), 7.33 (d, 1H), 7.40 (s, 1H), 7.51 (t, 1H), 7.62 (d, 1H), 7.78 (d, 1H).

EXAMPLE 24

Preparation of 1,2-Dimethoxy-4-(5-{3-[4-(2-methoxyphenyl)piperazinyl]propyl}isoxazol-3-yl)benzene About 2 min after dissolving 3-[3-(3,4-dimethoxyphenyl)isoxazol-5-yl]propanal (10 mg, 0.04 mmol) and 1-(2-methoxyphenyl)piperazine (7.4 mg, 0.04 mmol) in 2 mL of dry methylene chloride, were added NaBH(OAc)$_3$ (24 mg, 0.12 mmol) and molecular sieves (5 beads). The reaction mixture was reacted for 22.6 hr and followed the same processes as in Example 1 to obtain 18.9 mg (100%) of the target compound.

$^1$H NMR (300 MHz, CDCl$_3$) 1.99 (m, 2H), 2.53 (t, 2H, J=7.14 Hz), 2.69 (s, 4H), 2.86 (t, 2H, J=7.62 Hz), 3.11 (s, 4H), 3.89 (m, 9H), 6.29 (s, 1H), 6.91 (m, 5H), 7.26 (d, 1H), 7.41 (d, 1H).

EXAMPLE 25

Preparation of 2-Methoxy-1-(4-{3-[3-(3-nitrophenyl)isoxazol-5-yl]propyl}piperazinyl)benzene About 2 min after dissolving 3-[3-(3-nitrophenyl)isoxazol-5-yl]propanal (10 mg, 0.04 mmol) and 1-(2-methoxyphenyl)piperazine (8.0, 0.04 mmol) in 2 mL of dry methylene chloride, were added NaBH(OAc)$_3$ (24 mg, 0.12 mmol) and molecular sieves (5 beads). The reaction mixture was reacted for 5.10 hr and followed the same processes as in Example 1 to obtain 17.5 mg (100%) of the target compound.

$^1$H NMR (300 MHz, CDCl$_3$) 2.03 (m, 2H), 2.56 (t, 2H, J=6.99 Hz), 2.72 (s, 4H), 2.93 (t, 2H, J=7.62 Hz), 3.13 (s, 4H), 3.87 (s, 3H), 6.44 (s, 1H), 6.95 (m, 4H), 7.65 (t, 1H, J=7.98 Hz), 8.18 (d, 1H), 8.29 (d, 1H), 8.61 (d, 1H).

EXAMPLE 26

Preparation of 3-(3-Nitrophenyl)-5-[3-(4-{[2-(trifluoromethyl)phenyl]methyl}piperazinyl)propyl]isoxazole About 2 min after dissolving 3-[3-(3-nitrophenyl)isoxazol-5-yl]propanal (10 mg, 0.04 mmol) and 1-[2-

(trifluoromethyl)benyl]piperazine (8.4, 0.04 mmol) in 2 mL of dry methylene chloride, were added NaBH(OAc)$_3$ (26 mg, 0.12 mmol) and molecular sieves (5 beads). The reaction mixture was reacted for 4.8 hr and followed the same processes as in Example 1 to obtain 15.4 mg (79.9%) of the target compound.

$^1$H NMR (300 MHz, CDCl$_3$) 1.96 (m, 2H), 2.49 (m, 10H), 2.90 (t, 2H, J=7.41 Hz), 3.67 (s, 2H), 6.42 (s, 1H), 7.33 (t, 1H, J=7.68 Hz), 7.52 (t, 1H), 7.63 (m, 2H), 7.78 (d, 1H, J=7.47 Hz), 8.17 (d, 1H, J=7.8 Hz), 8.20 (d, 1H), 8.60 (d, 1H, J=1.68 Hz).

EXAMPLE 27

Preparation of 2-{5-[3-(4-{[2-(Trifluoromethyl) phenyl]methyl}piperazinyl)propyl]isoxazol-3-yl}thiophene About 2 min after dissolving 3-(3-(2-thienyl)isoxazol-5-yl)propanal (10 mg, 0.05 mmol) and 1-[2-(trifluoromethyl) benyl]piperazine (10.0, 0.05 mmol) in 2 mL of dry methylene chloride, were added NaBH(OAc)$_3$ (31 mg, 0.14 mmol) and molecular sieves (5 beads). The reaction mixture was reacted for 17 hr and followed the same processes as in Example 1 to obtain 13.1 mg (62.7%) of the target compound.

$^1$H NMR (300 MHz, CDCl$_3$) 1.95 (m, 2H), 2.49 (m, 10H), 2.84 (t, 2H, J=7.41 Hz), 3.67 (s, 2H), 6.25 (s, 1H), 7.10 (m, 1H), 7.31 (t, 1H), 7.41 (m, 2H), 7.50 (t, 1H), 7.61 (d, 1H), 7.78 (d, 1H).

EXAMPLE 28

Preparation of 2-Methoxy-1-{4-[3-(3-(2-thienyl) isoxazol-5-yl)propyl]piperazinyl}benzene About 2 min after dissolving 3-(3-(2-thienyl)isoxazol-5-yl)propanal (10 mg, 0.05 mmol) and 1-(2-methoxyphenyl) piperazine (9.2 mg, 0.05 mmol) in 2 mL of dry methylene chloride, were added NaBH(OAc)$_3$ (31 mg, 0.14 mmol) and molecular sieves (5 beads). The reaction mixture was reacted for 10 hr and followed the same processes as in Example 1 to obtain 15 mg (81.5%) of the target compound.

$^1$H NMR (300 MHz, CDCl$_3$) 1.93 (m, 2H), 2.53 (t, 2H, J=6.93 Hz), 2.69 (s, 4H), 2.87 (t, 2H, J=7.41 Hz), 3.12 (s, 4H), 3.87 (s, 3H), 6.27 (s, 1H), 6.91 (m, 4H), 7.10 (m, 1H), 7.41 (m, 2H).

EXAMPLE 29

Preparation of 1-(4-{3-[3-(4-Fluorophenyl)isoxizol-5-yl]propyl}piperazinyl)-2-methoxybenzene About 2 min after dissolving 3-[3-(4-fluorophenyl) isoxazol-5-yl]propanal (10 mg, 0.05 mmol) and 1-(2-methoxyphenyl)piperazine (8.8 mg, 0.05 mmol) in 2 mL of dry methylene chloride, were added NaBH(OAc)$_3$ (29 mg, 0.14 mmol) and molecular sieves (5 beads). The reaction mixture was reacted for 22.5 hr and followed the same processes as in Example 1 to obtain 14.1 mg (78.2%) of the target compound.

$^1$H NMR (300 MHz, CDCl$_3$) 2.02 (m, 2H), 2.55 (t, 2H, J=7.14 Hz), 2.71 (br s, 4H), 2.89 (t, 2H, J=7.47 Hz), 3.13 (br s, 4H), 3.87 (s, 3H), 6.30 (s, 1H), 6.95 (m, 4H), 7.15 (m, 2H), 7.78 (m, 2H); $^{13}$C NMR (150 MHz, CDCl$_3$) 24.97, 25.29, 30.36, 50.81, 53.97, 56.07, 58.01, 99.75, 112.00, 116.56, 116.72, 119.03, 121.75, 123.85, 126.23, 129.39, 152.97, 162.22, 165.27.

EXAMPLE 30

Preparation of 5-{3-[4-Benzylpiperazinyl]propyl}-3-(2-phenylvinyl)isoxazole

About 2 min after dissolving 3-[3-(2-phenylvinyl) isoxazol-5-yl]propanal (10 mg, 0.04 mmol) and 1-benylpiperazine (7.6, 0.04 mmol) in 2 mL of dry methylene chloride, were added NaBH(OAc)$_3$ (28 mg, 0.13 mmol) and molecular sieves (5 beads). The reaction mixture was reacted for 16.4 hr and followed the same processes as in Example 1 to obtain 10.6 mg (62.2%) of the target compound.

$^1$H NMR (300 MHz, CDCl$_3$) 1.94 (m, 2H), 2.49 (m, 10H), 2.81 (t, 2H, J=7.68 Hz), 3.54 (s, 2H), 6.24 (s, 1H), 7.12 (s, 2H), 7.32 (m, 8H), 7.52 (d, 2H); $^{13}$C NMR (150 MHz, CDCl$_3$) 25.21, 30.36, 31.01, 53.06, 53.42, 57.85, 63.40, 98.82, 109.80, 117.01, 127.63, 128.07, 129.03, 129.52, 130.04, 136.28, 136.62, 162.42.

EXAMPLE 31

Preparation of 3-(2-Phenylvinyl)-5-[3-(4-{[2-(trifluoromethyl)phenyl]methyl}piperazinyl)propyl] isoxazole About 2 min after dissolving 3-[3-(2-phenylvinyl) isoxazol-5-yl]propanal (10 mg, 0.05 mmol) and 1-[2-(trifluoromethyl)benyl]piperazine (9.2, 0.04 mmol) in 2 mL of dry methylene chloride, were added NaBH(OAc)$_3$ (28 mg, 0.13 mmol) and molecular sieves (5 beads). The reaction mixture was reacted for 16.4 hr and followed the same processes as in Example 1 to obtain 14 mg (69.8%) of the target compound.

$^1$H NMR (300 MHz, CDCl$_3$) 1.94 (m, 2H), 2.49 (m, 10H), 2.82 (t, 2H, J=7.68 Hz), 3.68 (s, 2H), 6.24 (s, 1 H), 7.12 (s, 2H), 7.34 (m, 4H), 7.51 (t, 2H, J=6.81 Hz), 7.62 (d, 1H, J=7.71 Hz), 7.78 (d, 1H, J=7.71 Hz).

EXAMPLE 32

Preparation of 1-(1-{3-[3-(2-Phenylvinyl)isoxazol-5-yl]propyl}-4-piperidyl)-3-hydrobenzimidazol-2-on About 2 min after dissolving 3-[3-(2-phenylvinyl) isoxazol-5-yl]propanal (10 mg, 0.04 mmol) and 4-[2-keto-1-benzimidazolinyl]piperidine (9.6 mg 0.04 mmol) in 2 mL of dry methylene chloride, were added NaBH(OAc)$_3$ (28 mg, 0.13 mmol) and molecular sieves (5 beads). The reaction mixture was reacted for 19.5 hr and followed the same processes as in Example 1 to obtain 3.4 mg (18.0%) of the target compound.

$^1$H NMR (300 MHz, CDCl$_3$) 1.86 (m, 2H), 2.12 (m, 2H), 2.32 (m, 2H), 2.67 (m, 4H), 2.91 (t, 2H), 3.29 (m, 2H), 4.45 (m, 1H), 6.32 (s, 1H), 7.09 (m, 5H), 7.38 (m, 4H), 7.52 (m, 2H), 8.69 (s, 1H).

EXAMPLE 33

Preparation of 1-(1-{3-[3-(4-Chlorophenyl)isoxazol-5-yl]propyl-4-piperidyl}-3-hydrobenzimidazol-2-on About 2 min after dissolving 3-[3-(4-chlorophenyl) isoxazol-5-yl]propanal (10 mg, 0.04 mmol) and 4-[2-keto-1-benzimidazolinyl]piperidine (9.1 mg 0.04 mmol) in 2 mL of dry methylene chloride, were added NaBH(OAc)$_3$ (27 mg, 0.13 mmol) and molecular sieves (5 beads). The reaction mixture was reacted for 22 hr and followed the same processes as in Example 1 to obtain 16 mg (87.2%) of the target compound.

¹H NMR (300 MHz, CDCl₃) 1.86 (m, 2H), 2.09 (m, 2H), 2.32 (m, 2H), 2.63 (m, 4H), 2.93 (t, 2H, J=7.47 Hz), 3.22 (m, 2H), 4.42 (m, 1H), 6.37 (s, 1H), 7.07 (m, 4H), 7.42 (m, 2H), 7.73 (m, 2H).

EXAMPLE 34

Preparation of 1-(1-{3-[3-(3-Nitrophenyl)isoxazol-5-yl]propyl}-4-piperidyl)-3- hydrobenzimidazol-2-on About 2 min after dissolving 3-[3-(3-nitrophenyl)isoxazol-5-yl]propanal (10 mg, 0.04 mmol) and 4-[2-keto-1-benzimidazolinyl]piperidine (8.8 mg, 0.04 mmol) in 2 mL of dry methylene chloride, were added NaBH(OAc)₃ (26 mg, 0.12 mmol) and molecular sieves (5 beads). The reaction mixture was reacted for 26.5 hr and followed the same processes as in Example 1 to obtain 14.7 mg (80.9%) of the target compound.

¹H NMR (300 MHz, CDCl₃) 1.84 (m, 2H), 2.04 (m, 2H), 2.25 (m, 2H), 2.58 (m, 4H), 2.95 (t, 2H, J=7.41 Hz), 3.18 (m, 2H), 4.42 (m, 1H), 6.47 (s, 1H), 7.08 (m, 3H), 7.31 (m, 1H), 7.65 (t, 1H), J=8.01 Hz), 8.18 (m, 1H), 8.29 (m, 1H), 8.62 (m, 1H), 9.74 (s, 1H).

EXAMPLE 35

Preparation of 1-Phenoxy-3-{5-[3-(4-{[2-(trifluoromethyl)phenyl]methyl}piperazinyl)propyl]isoxazol-3-yl}benzene About 2 min after dissolving 3-[3-(3-phenoxyphenyl)isoxazol-5-yl]propanal (10 mg, 0.03 mmol) and 1-[2-(trifluoromethyl)benzyl]piperazine (7.1, 0.03 mmol) in 2 mL of dry methylene chloride, were added NaBH(OAc)₃ (22 mg, 0.10 mmol) and molecular sieves (5 beads). The reaction mixture was reacted for 4 hr and followed the same processes as in Example 1 to obtain 14.7 mg (82.7%) of the target compound.

¹H NMR (300 MHz, CDCl₃) 1.95 (m, 2H), 2.46 (m, 10H), 2.84 (t, 2H, J=7.41 Hz), 3.67 (s, 2H), 6.27 (s, 1H), 7.09 (m, H), 7.37 (m, H), 7.53 (d, J=1.11 Hz), 7.62 (d, H, J=7.71 Hz), 7.77 (d, J=7.62 Hz).

EXAMPLE 36

Preparation of 1-(1-{3-[3-(3,4-Dimethoxyphenyl)isoxazol-5-yl]propyl}-4-piperidyl)-3-hydrobenzimidazol-2-on About 2 min after dissolving 3-[3-(3,4-dimethoxyphenyl)isoxazol-5-yl]propanal (10 mg, 0.04 mmol) and 4-(2-keto-1-benzimidazolinyl)piperidine (8.3 mg, 0.04 mmol) in 2 mL of dry methylene chloride, were added NaBH(OAc)₃ (24 mg, 0.12 mmol) and molecular sieves (5 beads). The reaction mixture was reacted for 26.1 hr and followed the same processes as in Example 1 to obtain 16 mg (90.3%) of the target compound.

¹H NMR (300 MHz, CDCl₃) 1.84 (m, 2H), 2.03 (m, 2H), 2.22 (m, 2H), 2.55 (m, 4H), 2.89 (t, 2H, J=7.68 Hz), 3.13 (m, 2H), 3.93 (m, 6H), 4.40 (m, 1H), 6.32 (s, 1H), 6.92 (d, 1H, J=8.46 Hz), 7.05 (m, 4H), 7.27 (m, 1H), 7.41 (s, 1H), 9.73 (s, 1H).

EXAMPLE 37

Preparation of 1-(1-{3-[3-(4-Fluorophenyl)isoxazol-5-yl]propyl}-4-piperidyl)-3-hydrobenzimidazol-2-on About 2 min after dissolving 3-[3-(4-fluorophenyl)isoxazol-5-yl]propanal (10 mg, 0.05 mmol) and 4-(2-keto-1-benzimidazolinyl)piperidine (9.9 mg, 0.05 mmol) in 2 mL of dry methylene chloride, were added NaBH(OAc)₃ (29 mg, 0.14 mmol) and molecular sieves (5 beads). The reaction mixture was reacted for 26.10 hr and followed the same processes as in Example 1 to obtain 6.4 mg (33.4%) of the target compound.

¹H NMR (300 MHz, CDCl₃) 1.85 (m, 2H), 2.06 (m, 2H), 2.24 (m, 2H), 2.56 (m, 4H), 2.89 (t, 2H), 3.16 (m, 2H), 4.41 (m, 1H), 6.32 (s, 1H), 7.09 (m, 6H), 7.78 (m, 2H), 9.65 (s, 1H).

EXAMPLE 38

Preparation of 1-{1-[3-(3-Phenylisoxazol-5-yl)propyl]-4-piperidyl}-3-hydrobenzimidazol-2-on About 2 min after dissolving 3-(3-phenylisoxazol-5-yl)propanal (10 mg, 0.05 mmol) and 4-(2-keto-1-benzimidazolinyl)piperidine (11 mg, 0.05 mmol) in 2 mL of dry methylene chloride, were added NaBH(OAc)₃ (32 mg, 0.15 mmol) and molecular sieves (5 beads). The reaction mixture was reacted for 47 hr and followed the same processes as in Example 1 to obtain 11.7 mg (58.1%) of the target compound.

¹H NMR (300 MHz, CDCl₃) 1.85 (m, 2H), 2.03 (m, 2H), 2.24 (m, 2F1), 2.55 (m, 4H), 2.91 (t, 2H, J=7.41 Hz), 3.17 (m, 2H), 4.41 (m, 1H), 6.36 (s, 1H), 7.07 (m, 4H), 7.45 (m, 3H), 7.80 (m, 2H), 9.64 (s, 1H); ¹³C NMR (150 MHz, CDCl₃) 25.42, 29.63, 30.37, 51.27, 53.84, 57.87, 89.97, 99.81, 110.34, 110.56, 121.95, 127.47, 128.66, 129.57, 130.02, 130.54, 155.72, 163.13.

EXAMPLE 39

Preparation of 1-(1-{3-[3-(3-Phenoxyphenyl)isoxazol-5-yl]propyl}-4-piperidyl)-3-hydrobenzimidazol-2-on About 2 min after dissolving 3-[3-(3-phenoxyphenyl)isoxazol-5-yl]propanal (10 mg, 0.03 mmol) and 4-(2-keto-1-benzimidazolinyl)piperidine (7.4 mg, 0.03 mmol) in 2 mL of dry methylene chloride, were added NaBH(OAc)₃ (22 mg, 0.12 mmol) and molecular sieves (5 beads). The reaction mixture was reacted for 21.75 hr and followed the same processes as in Example 1 to obtain 12.6 mg (74.7%) of the target compound.

¹H NMR (300 MHz, CDCl₃) 1.83 (m, 2H), 2.02 (m, 2H), 2.22 (m, 2H), 2.55 (m, 4H), 2.89 (t, 2H, J=7.62 Hz), 3.15 (m, 2H), 4.39 (m, 1H), 6.30 (s, 1H), 7.08 (m, 6H), 7.35 (m, 5H), 7.54 (m, 2H), 9.51 (s, 1H).

EXAMPLE 40

Preparation of 2-Methoxy-1-{4-[3-(3-(1,3-thiazol-2-yl)isoxazol-5-yl)propyl]piperazinyl}benzene About 2 min after dissolving 3-(3-(1,3-thiazol-2yl)isoxazol-5-yl)propanal (10 mg, 0.05 mmol)and 1-(2-methoxyphenyl)piperazine (9.2 mg, 0.05 mmol) in 2 mL of dry methylene chloride, were added NaBH(OAc)₃ (31 mg, 0.14 mmol) and molecular sieves (5 beads). The reaction mixture was reacted for 15.5 hr and followed the same processes as in Example 1 to obtain 17.7 mg (95.9%) of the target compound.

¹H NMR (300 MHz, CDCl₃) 2.00 (m, 2H), 2.52 (t, 2H, J=6.93 Hz), 2.68 (s, 4H), 2.91 (t, 2H, J=7.62 Hz), 3.11 (s, 4H), 3.86 (s, 3H), 6.62 (s, 1H), 6.92 (m, H), 7.46 (d, 1H, J=3.18 Hz), 7.95 (d, 1H, J=3.24 Hz).

EXAMPLE 41

Preparation of 2-(5-{3-[4-(Diphenylmethyl)piperazinyl]propyl}isoxazol-3-yl)-1,3-thiazole About 2 min after dissolving 3-(3-(1,3-thiazol-2-yl)isoxazol-5-yl)propanal (10 mg, 0.05 mmol) and 1-(2-diphenylmethyl)piperazine (12 mg, 0.05 mmol) in 2 mL of dry methylene chloride, were added NaBH(OAc)$_3$ (31 mg, 0.14 mmol) and molecular sieves (5 beads). The reaction mixture was reacted for 15.5 hr and followed the same processes as in Example 1 to obtain 18.7 mg (87.6%) of the target compound.

$^1$H NMR (300 MHz, CDCl$_3$) 1.95 (m, 2H), 2.47 (m, 10H), 2.87 (t, 2H, J=7.41 Hz), 4.22 (s, 1H), 6.59 (s, 1H), 7.17 (t, 2H), 7.28 (t, 4H), 7.42 (m, 5H), 7.94 (d, 1H).

EXAMPLE 42

Preparation of 3-(4-Chlorophenyl)-5-(3-[4-benzylpiperazinyl]propyl)isoxazole

About 2 min after dissolving 3-[3-(4-chlorophenyl)isoxazol-5-yl]propanal (10 mg, 0.04 mmol) and 1-benylpiperazine (7.3, 0.04 mmol) in 2 mL of dry methylene chloride, were added NaBH(OAc)$_3$ (27 mg, 0.13 mmol) and molecular sieves (5 beads). The reaction mixture was reacted for 2 hr and followed the same processes as in Example 1 to obtain 9.7 mg (58.3%) of the target compound.

$^1$H NMR (300 MHz, CDCl$_3$) 1.95 (m, 2H), 2.47 (m, 10H), 2.85 (t, 2H, J=7.68 Hz), 3.53 (s, 2H), 6.29 (s, 1H), 7.28 (m, 5H), 7.42 (m, 2H), 7.72 (m, 2H); $^{13}$C NMR (150 MHz, CDCl$_3$) 25.26, 30.36, 53.09, 53.45, 57.80, 63.40, 99.70, 127.32, 128.04, 128.48, 128.22. 129.03, 129.83, 130.01, 136.57, 162.14.

EXAMPLE 43

Preparation of 3-(3-Nitrophenyl)-5-{3-[4-benzylpiperazinyl]propyl}isoxazole

About 2 min after dissolving 3-[3-(3-nitrophenyl)isoxazol-5-yl]propanal (10 mg, 0.04 mmol) and 1-benylpiperazine (7.1, 0.04 mmol) in 2 mL of dry methylene chloride, were added NaBH(OAc)$_3$ (26 mg, 0.12 mmol) and molecular sieves (5 beads). The reaction mixture was reacted for 2 hr and followed the same processes as in Example 1 to obtain 7.4 mg (44.8%) of the target compound.

$^1$H NMR (300 MHz, CDCl$_3$) 1.97 (m, 2H), 2.51 (m, 10H), 2.87 (m, 2H), 3.54 (s, 2H), 6.42 (s, 1H), 7.30 (m, 5H), 7.65 (t, 1H, J=7.95Hz), 8.18 (m, 1H), 8.29 (m, 1H), 8.60 (t, 1H, J=1.77 Hz).

EXAMPLE 44

Preparation of 1,2-Dimethoxy-4-(5-{3-[4-benzylpiperazinyl]propyl}isoxazol-3-yl)benzene About 2 min after dissolving 3-[3-(3,4-dimethoxyphenyl)isoxazol-5-yl]propanal (20 mg, 0.08 mmol) and 1-benylpiperazine (13.4, 0.04 mmol) in 2 mL of dry methylene chloride, were added NaBH(OAc)$_3$ (48 mg, 0.23mmol) and molecular sieves (5 beads). The reaction mixture was reacted for 20 hr and followed the same processes as in Example 1 to obtain 24.1 mg (74.6%) of the target compound.

$^1$H NMR (300 MHz, CDCl$_3$) 1.94 (m, 2H), 2.49 (m, 10H), 2.82 (t, 2H, J=7.41 Hz), 3.52 (t, 2H), 3.92 (m, 6H), 6.26 (s, 1H), 6.91 (d, 1H, J=8.46 Hz), 7.29 (m, 6H), 7.40 (d, 1H, J=1.71 Hz).

EXAMPLE 45

Preparation of 2,4-Dimethoxy-1-(5-{3-[4-benzylpiperazinyl]propyl}isoxazol-3-yl)benzene About 2 min after dissolving 3-[3-(2,4-dimethoxyphenyl)isoxazol-5-yl]propanal (10 mg, 0.04 mmol) and 1-benylpiperazine (6.7, 0.04 mmol) in 2 mL of dry methylene chloride, were added NaBH(OAc)$_3$ (24 mg, 0.12 mmol) and molecular sieves (5 beads). The reaction mixture was reacted for 3.5 hr and followed the same processes as in Example 1 to obtain 13.5 mg (83.6%) of the target compound.

$^1$H NMR (300 MHz, CDCl$_3$) 1.95 (m, 2H), 2.48 (m, 10H), 2.81 (t, 2H, J=7.47 Hz), 3.53 (s, 2H), 3.86 (d, 6H, J=5.19 Hz), 6.45 (s, 1H), 6.54 (m, 3H), 7.31 (m, 4H), 7.80 (d, 1H, J=8.52 Hz).

EXAMPLE 46

Preparation of 2-(5-{3-[4-Benzylpiperazinyl]propyl-3-yl}thiophene

About 2 min after dissolving 3-(3-(2-thienyl)isoxazol-5-yl)propanal (20 mg, 0.10 mmol) and 1-benylpiperazine (16.7, 0.10 mmol) in 2 mL of dry methylene chloride, were added NaBH(OAc)$_3$ (61 mg, 0.29 mmol) and molecular sieves (5 beads). The reaction mixture was reacted for 2.8 hr and followed the same processes as in Example 1 to obtain 24.6 mg (69.7%) of the target compound.

$^1$H NMR (300 MHz, CDCl$_3$) 1.93 (m, 2H), 2.44 (m, 10H), 2.82 (t, 2H, J=7.71 Hz), 3.53 (s, 2H), 6.24 (s, 1H), 7.11 (m, 1H), 7.29 (m, 5H), 7.41 (m, 2H).

EXAMPLE 47

Preparation of 2-(5-{3-[4-Benzylpiperazinyl]propyl}isoxazol-3-yl)-1,3-thiazole

About 2 min after dissolving 3-(3-(1,3-thiazol-2-yl)isoxazol-5-yl)propanal (10 mg, 0.05 mmol) and 1-benylpiperazine (8.3, 0.05 mmol) in 2 mL of dry methylene chloride, were added NaBH(OAc)$_3$ (31 mg, 0.14 mmol) and molecular sieves (5 beads). The reaction mixture was reacted for 4.1 hr and followed the same processes as in Example 1 to obtain 10.3 mg (58.2%) of the target compound.

$^1$H NMR (300 MHz, CDCl$_3$) 1.95 (m, 2H), 2.45 (t, 2H, J=7.14 Hz), 2.52 (br s, 8H), 2.88 (t, 2H, J=7.41 Hz), 3.53 (s, 2H), 6.60 (s, 1H), 7.30 (m, 5H), 7.46 (t, 1H), 7.94 (t, 1H); $^{13}$C NMR (150 MHz, CDCl$_3$) 25.09, 25.28, 31.03, 53.42, 57.75, 59.45, 63.43, 100.14, 121.46, 128.05, 129.02, 130.06, 144.39, 152.07, 159.12.

EXAMPLE 48

Preparation of 3-(4-Fluorophenyl)-5-{3-[4-benzylpiperazinyl]propyl}isoxazole

About 2 min after dissolving 3-[3-(4-fluorophenyl)isoxazol-5-yl]propanal (20 mg, 0.09 mmol) and 1-benylpiperazine (15.9, 0.09 mmol) in 2 mL of dry methylene chloride, were added NaBH(OAc)$_3$ (58 mg, 0.27 mmol) and molecular sieves (5 beads). The reaction mixture was reacted for 22.5 hr and followed the same processes as in Example 1 to obtain 25.6 mg (74.0%) of the target compound.

$^1$H NMR (300 MHz, CDCl$_3$) 1.93 (m, 2H), 2.48 (m, 10H), 2.83 (t, 2H, J=7.62 Hz), 3.52 (s, 2H), 6.26 (s, 1H), 7.13 (t, 2H), 7.28 (m, 5H), 7.76 (m, 2H).

EXAMPLE 49

Preparation of 3-Phenyl-5-{3-[4-benzylpiperazinyl]propyl}isoxazole

About 2 min after dissolving 3-(3-phenylisoxazol-5-yl)propanal (20 mg, 0.10 mmol) and 1-benylpiperazine (17.4, 0.10 mmol) in 2 mL of dry methylene chloride, were added NaBH(OAc)$_3$ (64 mg, 0.30 mmol) and molecular sieves (5 beads). The reaction mixture was reacted for 4.1 hr and followed the same processes as in Example 1 to obtain 19.7 mg (54.5%) of the target compound.

$^1$H NMR (300 MHz, CDCl$_3$) 1.95 (m, 2H), 2.46 (m, 10H), 2.84 (m, 2H), 3.53 (s, 2H), 6.30 (s, 1H), 7.28 (m, 5H), 7.44 (m, 3H), 7.78 (m, 2H); $^{13}$C NMR (150 MHz, CDCl$_3$) 25.34, 30.34, 53.50, 53.68, 57.98, 63.58, 99.65, 127.42, 127.78, 128.90, 129.52, 129.91, 130.45, 138.48, 163.02, 174.32.

EXAMPLE 50

Preparation of 1-(5-{3-[4-Benzylpiperazinyl]propyl}isoxazol-3-yl)-3-phenoxybenzene About 2 min after dissolving 3-[3-(3-phenoxypheny)isoxazol-5-yl]propanal (20 mg, 0.07 mmol) and 1-benylpiperazine (11.9, 0.07 mmol) in 2 mL of dry methylene chloride, were added NaBH(OAc)$_3$ (43 mg, 0.20 mmol) and molecular sieves (5 beads). The reaction mixture was reacted for 4.5 hr and followed the same processes as in Example 1 to obtain 30.2 mg (97.6%) of the target compound.

$^1$H NMR (300 MHz, CDCl$_3$) 1.93 (m, 2H), 2.45 (m, 10H), 2.82 (t, 2H, J=7.41 Hz), 3.53 (s, 2H), 6.26 (s, 1H), 7.10 (m, 4H), 7.35 (m, 8H), 7.52 (d, 2H, J=7.53 Hz).

EXAMPLE 51

Preparation of 1-(5-{3-[4-(Diphenylmethyl)piperazinyl]propyl}isoxazol-3-yl)-3-dimethoxybenzene About 2 min after dissolving 3-[3-(2,4-dimethoxypheny)isoxazol-5-yl]propanal (10 mg, 0.04 mmol) and 1-(diphenylmethyl)piperazine (10.0 mg, 0.04 mmol) in 2 mL of dry methylene chloride, were added NaBH(OAc)$_3$ (24 mg, 0.12 mmol) and molecular sieves (5 beads). The reaction mixture was reacted for 22.5 hr and followed the same processes as in Example 1 to obtain 21.4 mg (100%) of the target compound.

$^1$H NMR (300 MHz, CDCl$_3$) 1.97 (m, 2H), 2.50 (t, 2H, J=7.29 Hz), 2.56 (br s, 8H), 2.81 (t, 2H, J=7.41 Hz), 3.86 (d, 6H, J=3.39 Hz), 4.24 (s, 1H), 6.45 (s, 1H), 6.55 (m, 2H), 7.17 (m, 2H), 7.27 (m, 4H), 7.41 (d, 4H, J=7.35 Hz), 7.80 (d, 1H, J=8.52 Hz); $^{13}$C NMR (150 MHz, CDCl$_3$) 24.97, 25.29, 51.97, 53.92, 56.09, 56.20, 57.98, 76.74, 99.59, 102.86, 105.81, 111.85, 127.65, 128.56, 129.18, 130.89, 143.23, 159.13, 160.48, 162.86.

EXAMPLE 52

Preparation of 2,4-Dimethoxy-1-{5-[3-(4-{[2-(trifluoromethyl)phenyl]methyl}piperazinyl)propyl]isoxazol-3-yl}benzene About 2 min after dissolving 3-[3-(2,4-dimethoxypheny)isoxazol-5-yl]propanal (10 mg, 0.04 mmol) and 1-[2-(trifluoromethyl)benzyl]piperazine (8.0, 0.04 mmol) in 2 mL of dry methylene chloride, were added NaBH(OAc)$_3$ (24 mg, 0.12 mmol) and molecular sieves (5 beads). The reaction mixture was reacted for 23.5 hr and followed the same processes as in Example 1 to obtain 15.6 mg (83.2%) of the target compound.

$^1$H NMR (300 MHz, CDCl$_3$) 1.97 (m, 2H), 2.49 (t, 2H, J=7.26 Hz), 2.55 (br s, 8H), 2.83 (t, 2H, J=7.44 Hz), 3.67 (s, 2H), 3.85 (m, 6H), 6.46 (s, 1H), 6.57 (m, 2H), 7.32 (m, 1H), 7.51 (m, 1H), 7.61 (m, 1H), 7.79 (m, 2H).

EXAMPLE 53

Preparation of 1-(1-{3-[3-(2,4-Dimethoxyphenyl)isoxazol-5-yl]propyl}-4-piperidyl)-3-hydrobenzimidazol-2-on About 2 min after dissolving 3-[3-(2,4-dimethoxypheny)isoxazol-5-yl]propanal (10 mg, 0.04 mmol) and 4-(2-keto-1-benzimidazolinyl)piperidine (8.3 mg, 0.04 mmol) in 2 mL of dry methylene chloride, were added NaBH(OAc)$_3$ (24 mg, 0.12 mmol) and molecular sieves (5 beads). The reaction mixture was reacted for 7 hr and followed the same processes as in Example 1 to obtain 18.3 mg (100%) of the target compound.

$^1$H NMR (300 MHz, CDCl$_3$) 1.86 (d, 2H, J=10.98 Hz), 2.04 (s, 2H), 2.27 (s, 2H), 2.58 (s, 4H), 2.88 (t, 2H, J=7.44 Hz), 3.18 (d, 2H, J=7.86 Hz), 3.86 (d, 6H, J=7.62 Hz), 4.42 (s, 1H), 6.49 (s, 1H), 6.57 (m, 2H), 7.07 (m, 3H), 7.34 (s, 1H), 7.82 (d, 1H, J=8.49 Hz), 9.67 (s, 1H).

EXAMPLE 54

Preparation of 1-{1-[3-(3-(2-Thienyl)isoxazol-5-yl)propyl]-4-piperidyl}-3-hydrobenzimidazol-2-on About 30 min after dissolving 3-(3-(2-thienyl)isoxazol-5-yl)propanal (20 mg, 0.10 mmol) and 4-(2-keto-1-benzimidazolinyl)piperidine (21 mg, 0.10 mmol) in 2 mL of dry methylene chloride, were added cold acetic acid (22.2, 0.39 mmol), NaBH(OAc)$_3$ (62 mg, 0.29 mmol) and molecular sieves (5 beads). The reaction mixture was reacted for 6 hr and followed the same processes as in Example 1 to obtain 29.1 mg (73.4%) of the target compound.

$^1$H NMR (300 MHz, CDCl$_3$) 1.84 (d, 2H, J=9.81 Hz), 1.97 (m, 2H), 2.21 (t, 2H), 2.53 (t, 4H, J=6.84 Hz), 2.88 (t, 2H, J=7.41 Hz), 3.13 (d, 2H, J=7.98 Hz), 4.39 (m, 1H), 6.28 (s, 1H), 7.09 (m, 4H), 7.28 (m, 1H), 7.42 (m, 2H).

EXAMPLE 55

Preparation of 3-(4-Fluorophenyl)-5-[3-(4-{[2-(trifluoromethyl)phenyl]methyl}piperazinyl)propyl]isoxazole About 2 min after dissolving 3-[3-(4-fluorophenyl)isoxazol-5-yl]propanal (20 mg, 0.09 mmol) and 1-[2-(trifluoromethyl)benzyl]piperidine (18.9, 0.09 mmol) in 2 mL of dry methylene chloride, were added NaBH(OAc)$_3$ (57.9 mg, 0.273 mmol) and molecular sieves (5 beads). The reaction mixture was reacted for 17.75 hr and followed the same processes as in Example 1 to obtain 28.9 mg (71.0%) of the target compound.

$^1$H NMR (300 MHz, CDCl$_3$) 1.95 (m, 2H), 2.46 (t, 2H, J=7.14 Hz), 2.53 (br s, 10H), 2.85 (t, 2H, J=7.56 Hz), 3.67 (s, 2H), 6.28 (s, 1H), 7.13 (m, 2H), 7.32 (t, 1H), 7.51 (t, 1H), 7.62 (d, 1H), 7.77 (m, 3H).

EXAMPLE 56

Preparation of 5-{3-[4-(4-Fluorophenyl)piperazinyl]propyl}-3-phenylisoxazole

About 2 min after dissolving 3-(3-phenylisoxazol-5-yl)propanal (27.4 mg, 0.14 mmol) and (4-fluorophenyl)

piperidine (24.5 mg, 0.14 mmol) in 2 mL of dry methylene chloride, were added NaBH(OAc)$_3$ (86.5 mg, 0.41 mmol) and molecular sieves (5 beads). The reaction mixture was reacted for 22 hr and followed the same processes as in Example 1 to obtain 37.8 mg (76.0%) of the target compound.

$^1$H NMR (300 MHz, CDCl$_3$) 1.95 (m, 2H), 2.51 (t, 2H, J=7.47 Hz), 2.63 (m, 4H), 2.89 (t, 2H, J=7.47 Hz), 3.14 (m, 4H), 6.33 (s, 1H), 6.90 (m, 5H), 7.44 (m, 3H), 7.78 (m, 2H).

EXAMPLE 57

Preparation of 3-Methoxy-1-(4-{3-[3-(3-nitrophenyl)isoxazol-5-yl]propyl}piperazinyl) benzene About 2 min after dissolving 3-[3-(3-nitrophenyl) isoxazol-5-yl]propanal (22.2 mg, 0.09 mmol) and (3-methoxyphenyl)piperidine (15.5, 0.09 mmol) in 2 mL of dry methylene chloride, were added NaBH(OAc)$_3$ (57.2 mg, 0.27 mmol) and molecular sieves (5 beads). The reaction mixture was reacted for 22 hr and followed the same processes as in Example 1 to obtain 32.8 mg (86.3%) of the target compound.

$^1$H NMR (300 MHz, CDCl$_3$) 2.01 (m, 2H), 2.51 (t, 2H, J=7.41 Hz), 2.63 (m, 4H), 2.92 (m, 2H), 3.22 (m, 4H), 3.79 (s, 3H), 6.42 (s, 1H), 6.43 (m, 2H), 6.52 (m, 1H), 7.17 (m, 1H), 7.65 (m, 1H), 8.18 (m, 1H), 8.28 (m, 1H), 8.61 (s, 1H).

EXAMPLE 58

Preparation of 1-(4-{3-[3-(3,4-Dimethoxyphenyl) isoxazol-5-yl]propyl}piperazinyl)-3-methoxybenzene About 2 min after dissolving 3-[3-(2,4-dimethoxyphenyl) isoxazol-5-yl]propanal (23.1 mg, 0.09 mmol) and (3-methoxyphenyl)piperidine (15.2, 0.09 mmol) in 2 mL of dry methylene chloride, were added NaBH(OAc)$_3$ (56.0 mg, 0.26 mmol) and molecular sieves (5 beads). The reaction mixture was reacted for 22 hr and followed the same processes as in Example 1 to obtain 27.0 mg (71.1%) of the target compound.

$^1$H NMR (300 MHz, CDCl$_3$) 2.01 (m, 2H), 2.51 (t, 2H, J=7.41 Hz), 2.63 (m, 4H), 2.92 (m, 2H), 3.22 (m, 4H), 3.79 (s, 3H), 3.93 (d, 6H, J=6.33 Hz) 6.29 (s, 1H), 6.43 (m, 2H), 6.52 (m, 1H), 6.92 (d, 1H, J=8.46 Hz), 7.17 (t, 1H), 7.27 (s, 1H), 7.41 (d, 1H, J=1.89 Hz).

EXAMPLE 59

Preparation of 3-(4-Chlorophenyl)-5-{3-[4-(2-chlorophenyl)piperazinyl]propyl}isoxazole About 2 min after dissolving 3-[3-(4-chlorophenyl) isoxazol-5-yl]propanal (27.3 mg, 0.12 mmol), (2-chlorophenyl)piperidine HCl (22.6 mg, 0.10 mmol), and diisopropylethyl amine (16.9, 0.10 mmol) in 2 mL of dry methylene chloride, were added NaBH(OAc)$_3$ (61.7 mg, 0.29 mmol) and molecular sieves (5 beads). The reaction mixture was reacted for 22 hr and followed the same processes as in Example 1 to obtain 36.4 mg (90.3%) of the target compound.

$^1$H NMR (300 MHz, CDCl$_3$) 1.98 (m, 2H), 2.51 (t, 2H, J=7.47 Hz), 2.63 (m, 4H), 2.89 (t, 2H, J=7.47 Hz), 3.14 (m, 4H), 6.33 (s, 1H), 6.95 (t, 1H), 7.04 (m, 1H), 7.20 (m, 1H), 7.35 (m, 1H), 7.42 (m, 2H), 7.72 (m, 2H).

EXAMPLE 60

Preparation of 4-(5-{3-[4-(2-Chlorophenyl) piperazinyl]propyl}isoxazol-3-yl)-1,2-dimethoxybenzene About 2 min after dissolving 3-[3-(3,4-dimethoxyphenyl) isoxazol-5-yl]propanal (34.0 mg, 0.13 mmol), (2-chlorophenyl)piperidine HCl (25.2 mg, 0.11 mmol), and diisopropylethyl amine (18.8, 0.11 mmol) in 2 mL of dry methylene chloride, were added NaBH(OAc)$_3$ (68.7 mg, 0.32 mmol) and molecular sieves (5 beads). The reaction mixture was reacted for 22 hr and followed the same processes as in Example 1 to obtain 39.8 mg (82.0%) of the target compound.

$^1$H NMR (300 MHz, CDCl$_3$) 1.98 (m, 2H), 2.51 (t, 2H, J=7.47 Hz), 2.63 (m, 4H), 2.89 (t, 2H, J=7.47 Hz), 3.14 (m, 4H), 3.93 (d, 6H), 6.33 (s, 1H), 6.95 (m, 3H), 7.30 (m, 4H).

EXAMPLE 61

Preparation of 2-(5-{3-[4-(2-Chlorophenyl) piperazinyl]propyl}isoxazol-3-yl)thiophene About 2 min after dissolving 3-(3-(2-thienyl)isoxazol-5-yl)propanal (27.8 mg, 0.13 mmol), (2-chlorophenyl) piperidine HCl (26.0 mg, 0.11 mmol), and diisopropylethyl amine (19.5, 0.11 mmol) in 2 mL of dry methylene chloride, were added NaBH(OAc)$_3$ (71.2 mg, 0.34 mmol) and molecular sieves (5 beads). The reaction mixture was reacted for 22 hr and followed the same processes as in Example 1 to obtain 41.4 mg (95.4%) of the target compound.

$^1$H NMR (300 MHz, CDCl$_3$) 1.98 (m, 2H), 2.51 (t, 2H, J=7.47 Hz), 2.63 (m, 4H), 2.89 (t, 2H, J=7.47 Hz), 3.14 (m, 4H), 3.93 (d, 6H), 6.27 (s, 1H), 7.02 (m, 4H), 7.22 (m, 1H), 7.39 (m, 2H).

EXAMPLE 62

Preparation of 5-{3-[4-(2-Chlorophenyl)piperazinyl] propyl}-3-phenylisoxazole

About 2 min after dissolving 3-(3-phenylisoxazol-5-yl) propanal (26.4 mg, 0.13 mmol), (2-chlorophenyl)piperidine HCl (25.5 mg, 0.11 mmol), and diisopropylethyl amine (19.0, 0.11 mmol) in 2 mL of dry methylene chloride, were added NaBH(OAc)$_3$ (69.3 mg, 0.33 mmol) and molecular sieves (5 beads). The reaction mixture was reacted for 22 hr and followed the same processes as in Example 1 to obtain 36.5 mg (87.7%) of the target compound.

$^1$H NMR (300 MHz, CDCl$_3$) 1.98 (m, 2H), 2.51 (t, 2H, J=7.47 Hz), 2.63 (m, 4H), 2.89 (t, 2H, J=7.47 Hz), 3.14 (m, 4H), 6.33 (s, 1H), 6.96 (t, 1H), 7.05 (d, 1H) 7.22 (t, 1H), 7.32 (m, 1H), 7.42 (m, 3H), 7.79 (m, 2H).

EXAMPLE 63

Preparation of 1-(5-{3-[4-(2-Chlorophenyl) piperazinyl]propyl}isoxazol-3-yl)-3-phenoxybenzene About 2 min after dissolving 3-[3-(3-phenoxyphenyl) isoxazol-5-yl]propanal (40.8 mg, 0.14 mmol), (2-chlorophenyl)piperidine HCl (27.0 mg, 0.12 mmol), and diisopropylethyl amine (20.2, 0.12 mmol) in 2 mL of dry methylene chloride, were added NaBH(OAc)$_3$ (73.8 mg, 0.35 mmol) and molecular sieves (5 beads). The reaction mixture was reacted for 22 hr and followed the same processes as in Example 1 to obtain 52.7 mg (95.6%) of the target compound.

$^1$H NMR (300 MHz, CDCl$_3$) 1.98 (m, 2H), 2.51 (t, 2H, J=7.47 Hz), 2.63 (m, 4H), 2.89 (t, 2H, J=7.47 Hz), 3.14 (m, 4H), 6.28 (s, 1H), 7.08 (m, 5H), 7.22 (m, 2H) 7.35 (m, 5H), 7.53 (m, 1H).

EXAMPLE 64

Preparation of 1-(4-{3-[3-(3,4-Dimethoxyphenyl) isoxazol-5-yl]propyl}piperazinyl)-2-ethoxybenzene About 2 min after dissolving 3-[3-(3,4-dimethoxyphenyl) isoxazol-5-yl]propanal (22.1 mg, 0.09 mmol), (2-chlorophenyl)piperidine HCl (20.6 mg, 0.09 mmol), and diisopropylethyl amine (14.8, 0.09 mmol) in 2 mL of dry methylene chloride, were added NaBH(OAc)$_3$ (54.0 mg, 0.26 mmol) and molecular sieves (5 beads). The reaction mixture was reacted for 20 hr and followed the same processes as in Example 1 to obtain 28.5 mg (74.2%) of the target compound.

$^1$H NMR (300 MHz, CDCl$_3$) 1.45 (t, 3H), 1.98 (m, 2H), 2.51 (t, 2H, J=7.47 Hz), 2.63 (m, 4H), 2.89 (t, 2H, J=7.47 Hz), 3.14 (m, 4H), 3.93 (m, 6H), 4.06 (m, 2H), 6.28 (s, 1H), 6.90 (m, 5H), 7.28 (m, 1H) 7.41 (m, 5H).

EXAMPLE 65

Preparation of 2-Ethoxy-1-{4-[3-(3-(2-thienyl) isoxazol-5-yl)propyl]piperazinyl}benzene About 2 min after dissolving 3-(3-(2-thienyl)isoxazol-5-yl)propanal (21.9 mg, 0.11 mmol), (2-ethoxyphneyl)piperidine HCl (25.7 mg, 0.11 mmol), and diisopropylethyl amine (18.5, 0.11 mmol) in 2 mL of dry methylene chloride, were added NaBH(OAc)$_3$ (67.4 mg, 0.32 mmol) and molecular sieves (5 beads). The reaction mixture was reacted for 20 hr and followed the same processes as in Example 1 to obtain 31.0 mg (75.4%) of the target compound.

$^1$H NMR (300 MHz, CDCl$_3$) 1.45 (m, 3H), 2.01 (m, 2H), 2.51 (t, 2H, J=7.47 Hz), 2.63 (m, 4H), 2.89 (t, 2H, J=7.47 Hz), 3.14 (m, 4H), 4.07 (m, 2H), 6.28 (s, 1H), 6.90 (m, 4H), 7.11 (m, 1H) 7.42 (m, 2H).

EXAMPLE 66

Preparation of 2-Ethoxy-1-(4-{3-[3-(2-phenylvinyl) isoxazol-5-yl]propyl}piperazinyl)benzene About 2 min after dissolving 3-[3-(2-phenylvinyl) isoxazol-5-yl]propanal (27.0 (mg, 0.12 mmol), (2-ethoxyphneyl)piperidine HCl (28.9 mg, 0.12 mmol), and diisopropylethyl amine (20.7, 0.12 mmol) in 2 mL of dry methylene chloride, were added NaBH(OAc)$_3$ (75.7 mg, 0.36 mmol) and molecular sieves (5 beads). The reaction mixture was reacted for 20 hr and followed the same processes as in Example 1 to obtain 41.0 mg (82.7%) of the target compound.

$^1$H NMR (300 MHz, CDCl$_3$) 1.45 (t, 3H, J=6.90 Hz), 2.01 (m, 2H), 2.51 (t, 2H, J=7.47 Hz), 2.63 (m, 4H), 2.83 (m, 2H), 3.14 (m, 4H), 4.07 (m, 2H), 6.27 (s, 1H), 6.90 (m, 5H), 7.11 (s, 2H) 7.37 (m, 2H), 7.52 (m, 2H).

EXAMPLE 67

Preparation of 5-{4-[4-(Diphenylmethyl) piperazinyl]butyl}-3-(4-fluorophenyl)isoxazole About 2 min after dissolving 3-[3-(4-fluorophenyl) isoxazol-5-yl]butanal (98 mg, 0.42 mmol) and 1-(diphenylmethyl)piperidine (106 mg, 0.42 mmol) in 4 mL of dry methylene chloride, were added NaBH(OAc)$_3$ (267 mg, 1.26 mmol) and molecular sieves (5 beads). The reaction mixture was reacted for 20 hr and followed the same processes as in Example 1 to obtain 172.6 mg (87.5%) of the target compound.

$^1$H NMR (300 MHz, CDCl$_3$) 1.59 (m, 2H), 1.77 (m, 2H), 2.40 (m, 10H), 2.81 (t, 2H, J=7.41 Hz), 4.23 (s, 1H), 6.25 (s, 1H), 7.17 (m, 4H), 7.27 (m, 4H), 7.42 (d, 4H, J=7.14 Hz), 7.77 (m, 2H); $^{13}$C NMR (150 MHz, CDCl$_3$) 25.96, 26.72, 27.09, 52.33, 53.96, 58.50, 76.71, 99.26, 116.22, 116.51, 126.03, 126.07, 127.35, 127.51, 128.36, 128.91, 129.02, 129.13, 143.22, 161.77, 162.42, 165.72, 174.51.

EXAMPLE 68

Preparation of 5-{4-[4-(Diphenylmethyl) piperazinyl]butyl}-3-(3-nitrophenyl)isoxazole About 2 min after dissolving 3-[3-(3-nitrophenyl) isoxazol-5-yl]butanal (24 mg, 0.092 mmol) and 1-(diphenylmethyl)piperidine (23.2 mg, 0.092 mmol) in 4 mL of dry methylene chloride, were added NaBH(OAc)$_3$ (58.5 mg, 0.296 mmol) and molecular sieves (5 beads). The reaction mixture was reacted for 4 hr and followed the same processes as in Example 1 to obtain 29.8 mg (65.2%) of the target compound.

$^1$H NMR (300 MHz, CDCl$_3$) 1.60 (m, 2H), 1.79 (m, 2H), 2.44 (m, 10H), 2.85 (t, 2H, J=7.41 Hz), 4.22 (s, 1H), 6.39 (s, 1H), 7.21 (m, 6H), 7.40 (m, 4H), 7.64 (t, 1H, J=7.95 Hz), 8.18 (m, 1H), 8.28 (m, 1H), 8.60 (t, 1H, J=1.74 Hz).

EXAMPLE 69

Preparation of 4-(5-{4-[4-(Diphenylmethyl) piperazinyl]butyl}isoxazol-3-yl)-1,2-dimethoxybenzene About 2 min after dissolving 3-[3-(3,4-dimethoxyphenyl) isoxazol-5-yl]butanal (20 mg, 0.073 mmol) and 1-(diphenylmethyl)piperidine (18.4 mg, 0.073 mmol) in 4 mL of dry methylene chloride, were added NaBH(OAc)$_3$ (46.4 mg, 0.219 mmol) and molecular sieves (5 beads). The reaction mixture was reacted for 17 hr and followed the same processes as in Example 1 to obtain 29.6 mg (79.2%) of the target compound.

$^1$H NMR (300 MHz, CDCl$_3$) 1.60 (m, 2H), 1.74 (m, 2H), 2.43 (m, 10H), 2.80 (t, 2H), 3.93 (d, 6H, J=5.61 Hz), 4.22 (s, 1H), 6.25 (s, 1H), 6.91 (d, 1H, J=8.34 Hz), 7.17 (m, 2H), 7.26 (m, 5H), 7.41 (m, 5H).

EXAMPLE 70

Preparation of 1-(5-{4-[4-(Diphenylmethyl) piperazinyl]butyl}isoxazol-3-yl)-2,4-dimethoxybenzene About 2 min after dissolving 3-[3-(2,4-dimethoxyphenyl) isoxazol-5-yl]butanal (20 mg, 0.073 mmol) and 1-(diphenylmethyl)piperidine (18.4 mg, 0.073 mmol) in 4 mL of dry methylene chloride, were added NaBH(OAc)$_3$ (46.4 mg, 0.219 mmol) and molecular sieves (5 beads). The reaction mixture was reacted for 17 hr and followed the same processes as in Example 1 to obtain 30 mg (80.3%) of the target compound.

$^1$H NMR (300 MHz, CDCl$_3$) 1.58 (m, 2H), 1.76 (m, 2H), 2.43 (m, 10H), 2.79 (t, 2H), 3.85 (m, 6H), 4.22 (s, 1H), 6.43 (s, 1H), 6.54 (m, 2H), 7.16 (m, 2H), 7.26 (m, 4H), 7.41 (m, 4H), 7.80 (d, 1H, J=8.46 Hz); $^{13}$C NMR (150 MHz, CDCl$_3$) 26.23, 26.78, 27.32, 30.34, 52.35, 54.11, 56.08, 56.21, 58.70, 76.86, 99.66, 102.65, 105.88, 112.04, 127.56, 128.62, 129.10, 130.93, 143.40, 159.15, 160.41, 162.83, 172.90.

EXAMPLE 71

Preparation of 5-{4-[4-(Diphenylmethyl) piperazinyl]butyl}-3-phenylisoxazole

About 2 min after dissolving 3-(3-phenylisoxazol-5-yl) butanal (30 mg, 0.139 mmol) and 1-(diphenylmethyl)

piperidine (35.1 mg, 0.139 mmol) in 4 mL of dry methylene chloride, were added NaBH(OAc)$_3$ (88.4 mg, 0.417 mmol) and molecular sieves (5 beads). The reaction mixture was reacted for 5.8 hr and followed the same processes as in Example 1 to obtain 11.2 mg (17.8%) of the target compound.

$^1$H NMR (300 MHz, CDCl$_3$) 1.60 (m, 2H), 1.77 (m, 2H), 2.46 (m, 10H), 2.82 (t, 2H, J=7.41 Hz), 4.23 (s, 1H), 6.29 (s, 1H), 7.21 (m, 6H), 7.41 (m, 7H), 7.77 (m, 2H).

EXAMPLE 72

Preparation of 2-{4-[4-(4-{[2-(Trifluoromethyl)phenyl]methyl}piperazinyl)butyl]isoxazol-3-yl}thiophene About 2 min after dissolving 3-(3-(2-thienyl)isoxazol-5-yl)butanal (15 mg, 0.068 mmol) and 1-[2-(trifluoromethyl)benzyl]piperidine (14.1, 0.068 mmol) in 4 mL of dry methylene chloride, were added NaBH(OAc)$_3$ (43.2 mg, 0.204 mmol) and molecular sieves (5 beads). The reaction mixture was reacted for 17.75 hr and followed the same processes as in Example 1 to obtain 26.3 mg (86.0%) of the target compound.

$^1$H NMR (300 MHz, CDCl$_3$) 1.60 (m, 2H), 1.75 (m, 2H), 2.40 (t, 2H, J=7.47 Hz), 2.51 (br s, 8H), 2.80 (t, 2H, J=7.14 Hz), 3.66 (s, 2H), 6.24 (s, 1H), 7.10 (m, 1H), 7.32 (t, 1H), 7.42 (m, 2H), 7.51 (t, 1H), 7.62 (d, 1H), 7.78 (d, 1H).

EXAMPLE 73

Preparation of 3-Phenyl-5-[4-(4-{[2-(trifluoromethyl)phenyl]methyl}piperazinyl)butyl]isoxazole About 2 min after dissolving 3-(3-phenylisoxazol-5-yl)butanal (30 mg, 0.1 39 mmol) and 1-[2-(trifluoromethyl)benzyl]piperidine (28.9, 0.139 mmol) in 4 mL of dry methylene chloride, were added NaBH(OAc)$_3$ (88.4 mg, 0.417 mmol) and molecular sieves (5 beads). The reaction mixture was reacted for 17.75 hr and followed the same processes as in Example 1 to obtain 9.1 mg (14.8%) of the target compound.

$^1$H NMR (300 MHz, CDCl$_3$) 1.66 (m, 2H), 1.79 (m, 2H), 2.48 (t, 2H, J=7.47 Hz), 2.57 (br s, 8H), 2.84 (t, 2H, J=7.47 Hz), 3.68 (s, 2H), 6.31 (s, 1H), 7.32 (t, 1H), 7.45 (m, 4H), 7.62 (d, 1H), 7.77 (m, 3H).

EXAMPLE 74

Preparation of 1-(5-{4-[4-(Diphenylmethyl)piperazinyl]butyl}isoxazol-3-yl)-3-phenoxybenzene About 2 min after dissolving 3-[3-(3-phenoxyphenyl)isoxazol-5-yl]butanal (29.4 mg, 0.096 mmol) and 1-(diphenylmethyl)piperidine (24.2 mg, 0.096 mmol) in 4 mL of dry methylene chloride, were added NaBH(OAc)$_3$ (61 mg, 0.288 mmol) and molecular sieves (5 beads). The reaction mixture was reacted for 3 hr and followed the same processes as in Example 1 to obtain 17.4 mg (33.3%) of the target compound.

$^1$H NMR (300 MHz, CDCl$_3$) 1.59 (m, 2H), 1.76 (m, 2H), 2.45 (m, 10H), 2.80 (t, 2H, J=7.41 Hz), 4.23 (s, 1H), 6.24 (s, 1H), 7.05 (m, 2H), 7.16 (m, 2H), 7.27 (m, 5H), 7.36 (m, 7H), 7.51 (m, 2H).

EXAMPLE 75

Preparation of 5-{4-[4-(Diphenylmethyl)piperazinyl]butyl}-3-(2-phenylvinyl)isoxazole About 2 min after dissolving 3-[3-(2-phenylvinyl)isoxazol-5-yl]butanal (21.5 mg, 0.089 mmol) and 1-(diphenylmethyl)piperidine (22.5 mg, 0.089 mmol) in 4 mL of dry methylene chloride, were added NaBH(OAc)$_3$ (56.6 mg, 0.267 mmol) and molecular sieves (5 beads). The reaction mixture was reacted for 3 hr and followed the same processes as in Example 1 to obtain 16.8 mg (39.5%) of the target compound.

$^1$H NMR (300 MHz, CDCl$_3$) 1.60 (m, 2H), 1.75 (m, 2H), 2.45 (m, 10H), 2.76 (t, 2H, J=7.41 Hz), 4.23 (s, 1H), 6.23 (s, 1H), 7.11 (d, 2H, J=2.97 Hz), 7.30 (m, 13H), 7.51 (d, 2H, J=6.81 Hz).

EXAMPLE 76

Preparation of 3-Phenoxy-1-{5-[4-(4-{[2-(trifluoromethyl)phenyl]methyl}piperazinyl)butyl]isoxazol-3-yl}benzene About 2 min after dissolving 3-[3-(3-phenoxyphenyl)isoxazol-5-yl]butanal (48.6 mg, 0.158 mmol) and 1-[2-(trifluoromethyl)benzyl]piperidine (32.9, 0.158 mmol) in 4 mL of dry methylene chloride, were added NaBH(OAc)$_3$ (100 mg, 0.474 mmol) and molecular sieves (5 beads). The reaction mixture was reacted for 1.75 hr and followed the same processes as in Example 1 to obtain 48 mg (56.7%) of the target compound.

$^1$H NMR (300 MHz, CDCl$_3$) 1.60 (m, 2H), 1.77 (m, 2H), 2.40 (t, 2H, J=7.62 Hz), 2.52 (br s, 8H), 2.81 (t, 2H, J=7.38 Hz), 3.66 (s, 2H), 6.26 (s, 1H), 7.08 (m, 3H), 7.40 (m, 8H), 7.62 (d, 1H), 7.78 (d, 1H).

EXAMPLE 77

Preparation of 3-(2-Phenylvinyl)-5-[4-(4-{[2-(trifluoromethyl)phenyl]methyl}piperazinyl)butyl]isoxazole About 2 min after dissolving 3-[3-(2-phenylvinyl)isoxazol-5-yl]butanal (17 mg, 0.070 mmol) and 1-[2-(trifluoromethyl)benzyl]piperidine (14.6, 0.070 mmol) in 2 mL of dry methylene chloride, were added NaBH(OAc)$_3$ (100 mg, 0.474 mmol) and molecular sieves (5 beads). The reaction mixture was reacted for 1.75 hr and followed the same processes as in Example 1 to obtain 9.8 mg (29.8%) of the target compound.

$^1$H NMR (300 MHz, CDCl$_3$) 1.67 (m, 2H), 1.76 (m, 2H), 2.53 (m, 10H), 2.80 (t, 2H, J=7.65 Hz), 3.68 (s, 2H), 6.25 (s, 1H), 7.12 (d, 2H, J=1.86 Hz), 7.35 (m, 4H), 7.51 (m, 3H), 7.61 (d, 1H), 7.76 (d, 1H).

EXAMPLE 78

Preparation of 1,2-Dimethoxy-4-{5-[4-(4-{[2-(trifluoromethyl)phenyl]methyl}piperazinyl)butyl]isoxazol-3-yl}benzene About 2 min after dissolving 3-[3-(3,4-dimethoxyphenyl)isoxazol-5-yl]butanal (17 mg, 0.062 mmol) and 1-[2-(trifluoromethyl)benzyl]piperidine (12.9, 0.062 mmol) in 2 mL of dry methylene chloride, were added NaBH(OAc)$_3$ (39.4 mg, 0.186 mmol) and molecular sieves (5 beads). The reaction mixture was reacted for 23.80 hr and followed the same processes as in Example 1 to obtain 43.4 mg (100%) of the target compound.

$^1$H NMR (300 MHz, CDCl$_3$) 1.62 (m, 2H), 1.78 (m, 2H), 2.42 (t, 2H, J=7.41 Hz), 2.53 (br s, 8H), 2.81 (t, 2H, J=7.20 Hz), 3.66 (s, 2H), 3.93 (m, 6H), 6.26 (s, 1H), 6.91 (d, 1H, J=8.25 Hz), 7.29 (m, 2H), 7.40 (d, 1H), 7.49 (t, 1H), 7.61 (d, 1H), 7.76 (d, 1H).

EXAMPLE 79

Preparation of 2,4-Dimethoxy-1-{5-[4-(4-{[2-(trifluoromethyl)phenyl]methyl}piperazinyl)butyl]isoxazol-3-yl}benzene About 2 min after dissolving 3-[3-(2,4-dimethoxyphenyl)isoxazol-5-yl]butanal (14 mg, 0.051 mmol) and 1-[2-(trifluoromethyl)benzyl]piperidine (10.6, 0.051 mmol) in 2 mL of dry methylene chloride, were added NaBH(OAc)$_3$ (32.4 mg, 0.153 mmol) and molecular sieves (5 beads). The reaction mixture was reacted for 15.1 hr and followed the same processes as in Example 1 to obtain 65.1 mg (100%) of the target compound.

$^1$H NMR (300 MHz, CDCl$_3$) 1.60 (m, 2H), 1.76 (m, 2H), 2.40 (t, 2H, J=7.47 Hz), 2.51 (br s, 8H), 2.79 (t, 2H, J=7.35 Hz), 3.65 (s, 2H), 3.85 (m, 6H), 6.44 (s, 1H), 6.55 (m, 2H), 7.31 (t, 1H), 7.49 (t, 1H), 7.61 (d, 1H), 7.79 (m, 2H).

EXAMPLE 80

Preparation of 3-(4-Fluorophenyl)-5-[4-(4-{[2-(trifluoromethyl)phenyl]methyl}piperazinyl)butyl]isoxazole About 2 min after dissolving 3-[3-(4-fluorophenyl)isoxazol-5-yl]butanal (60 mg, 0.257 mmol) and 1-[2-(trifluoromethyl)benzyl]piperidine (53.5, 0.257 mmol) in 2 mL of dry methylene chloride, were added NaBH(OAc)$_3$ (163 mg, 0.771 mmol) and molecular sieves (5 beads). The reaction mixture was reacted for 2.75 hr and followed the same processes as in Example 1 to obtain 88.9 mg (75.0%) of the target compound.

$^1$H NMR (300 MHz, CDCl$_3$) 1.59 (m, 2H), 1.77 (m, 2H), 2.39 (t, 2H, J=7.47 Hz), 2.50 (br s, 8H), 2.81 (t, 2H, J=7.41 Hz), 3.65 (s, 2H), 6.25 (s, 1H), 7.12 (m, 2H), 7.28 (m, 1H), 7.49 (t, 1H), 7.60 (d, 1H, J=7.68 Hz), 7.76 (t, 3H, J=8.58 Hz); $^{13}$C NMR (150 MHz, CDCl$_3$) 26.12, 26.87, 27.26, 53.74, 53.93, 58.59, 58.81, 99.39, 116.42, 116.56, 126.04, 126.30, 126.33, 127.31, 129.22, 129.27, 131.01, 132.25, 138.51, 162.00, 163.49, 165.15, 174.73.

EXAMPLE 81

Preparation of 3-(3-Nitrophenyl)-5-[4-(4-{[2-(trifluoromethyl)phenyl]methyl}piperazinyl)butyl]isoxazole About 2 min after dissolving 3-[3-(3-nitrophenyl)isoxazol-5-yl]butanal (27 mg, 0.104 mmol) and 1-[2-(trifluoromethyl)benzyl]piperidine (21.6, 0.104 mmol) in 2 mL of dry methylene chloride, were added NaBH(OAc)$_3$ (66 mg, 0.312 mmol) and molecular sieves (5 beads). The reaction mixture was reacted for 3.5 hr and followed the same processes as in Example 1 to obtain 40.5 mg (79.7%) of the target compound.

$^1$H NMR (300 MHz, CDCl$_3$) 1.63 (m, 2H), 1.81 (m, 2H), 2.43 (t, 2H, J=7.35 Hz), 2.53 (br s, 8H), 2.86 (t, 2H, J=7.41 Hz), 3.66 (s, 2H), 6.40 (s, 1H), 7.30 (m, 1H), 7.50 (m, 1H), 7.62 (m, 2H), 7.76 (d, 1H), 8.17 (d, 1H), 8.28 (d, 1H), 8.60 (s, 1H).

EXAMPLE 82

Preparation of 1-(1-{4-[3-(4-Fluorophenyl)isoxazol-5-yl]butyl}-4-piperidyl)-3-hydrobenzimidazol-2-on About 2 min after dissolving 3-[3-(4-fluorophenyl)isoxazol-5-yl]butanal (50 mg, 0.214 mmol) and 4-(2-keto-1-benzimidazolinylpiperidine (46.5 mg, 0.214 mmol) in 3 mL of dry methylene chloride, were added NaBH(OAc)$_3$ (136 mg, 0.642 mmol) and molecular sieves (5 beads). The reaction mixture was reacted for 23 hr and followed the same processes as in Example 1 to obtain 62.2 mg (66.9%) of the target compound.

$^1$H NMR (300 MHz, CDCl$_3$) 1.67 (m, 2H), 1.83 (m, 4H), 2.18 (m, 2H), 2.47 (m, 4H), 2.85 (t, 2H, J=7.41 Hz), 3.12 (m, 2H), 4.40 (m, 1H), 6.29 (s, 1H), 7.09 (m, 5H), 7.28 (m, 1H), 7.78 (m, 2H).

EXAMPLE 83

Preparation of 1-(1-{4-[3-(3-Nitrophenyl)isoxazol-5-yl]butyl}-4-piperidyl)-3-hydrobenzimidazol-2-on About 2 min after dissolving 3-[3-(3-nitrophenyl)isoxazol-5-yl]butanal (41 mg, 0.158 mmol) and and 4-(2-keto-1-benzimidazolinyl)piperidine (34.3 mg, 0.158 mmol) in 2.5 mL of dry methylene chloride, were added NaBH(OAc)$_3$ (100 mg, 0.474 mmol) and molecular sieves (5 beads). The reaction mixture was reacted for 23 hr and followed the same processes as in Example 1 to obtain 46.2 mg (63.4%) of the target compound.

$^1$H NMR (300 MHz, CDCl$_3$) 1.67 (m, 2H), 1.85 (m, 4H), 2.21 (m, 2H). 2.50 (m, 4H), 2.90 (t, 2H, J=7.38 Hz), 3.16 (m, 2H), 4.39 (m, 1H), 6.44 (s, 1H), 7.06 (m, 4H), 7.32 (m, 1H), 7.65 (t, 1H), 8.18 (d, 1H), 8.62 (s, 1H).

EXAMPLE 84

Preparation of 1-{1-[4-(3-(2-Thienyl)isoxazol-5-yl)butyl]-4-piperidyl}-3-hydrobenzimidazol-2-on About 2 min after dissolving 3-(3-(2-thienyl)isoxazol-5-yl)butanal (20 mg, 0.090 mmol) and 4-(2-keto-1-benzimidazolinyl)piperidine (19.6 mg, 0.090 mmol) in 2 mL of dry methylene chloride, were added NaBH(OAc)$_3$ (57.2 mg, 0.270 mmol) and molecular sieves (5 beads). The reaction mixture was reacted for 25.75 hr and followed the same processes as in Example 1 to obtain 23.5 mg (61.8%) of the target compound.

$^1$H NMR (300 MHz, CDCl$_3$) 1.65 (m, 2H), 1.81 (m, 4H), 2.18 (m, 2H). 2.51 (m, 4H), 2.84 (t, 2H, J=7.14 Hz), 3.14 (m, 2H), 4.39 (m, 1H), 6.27 (s, 1H), 7.08 (m, 4H), 7.31 (m, 1H), 7.42 (m, 2H), 9.97 (br s, 1H).

EXAMPLE 85

Preparation of 1-{1-[4-(3-Phenylisoxazol-5-yl)butyl]-4-piperidyl}-3-hydrobenzimidazol-2-on About 2 min after dissolving 3-(3-phenylisoxazol-5-yl)butanal (27 mg, 0.104 mmol) and 4-(2-keto-1-benzimidazolinyl)piperidine (35.4 mg, 0.163 mmol) in 2 mL of dry methylene chloride, were added NaBH(OAc)$_3$ (104 mg, 0.489 mmol) and molecular sieves (5 beads). The reaction mixture was reacted for 16 hr and followed the same processes as in Example 1 to obtain 20.1 mg (51.9%) of the target compound.

$^1$H NMR (300 MHz, CDCl$_3$) 1.67 (m, 2H), 1.78 (m, 4H), 2.19 (m, 2H), 2.50 (m, 4H), 2.83 (t, 2H, J=7.14 Hz), 3.15 (m, 2H), 6.32 (s, 1H), 7.05 (m, 4H), 7.43 (m, 3H), 7.78 (m, 2H), 9.82 (br s, 1H).

EXAMPLE 86

Preparation of 1-(1-{4-[3-(3,4-Dimethoxyphenyl)isoxazol-5-yl]butyl}-4-piperidyl)-3-hydrobenzimidazol-2-on About 2 min after dissolving 3-[3-(3,4-dimethoxyphenyl)isoxazol-5-yl]butanal (43 mg, 0.156 mmol) and 4-(2-keto- 1-benzimidazolinyl)piperidine (33.9 mg, 0.156 mmol) in 3 mL of dry methylene chloride, were added NaBH(OAc)$_3$ (99.2 mg, 0.468 mmol), cold acetic acid (10.7, 0.187 mmol) and molecular sieves (5 beads). The reaction mixture was reacted for 4.5 hr and followed the same processes as in Example 1 to obtain 61.7 mg (83.0%) of the target compound.

$^1$H NMR (300 MHz, CDCl$_3$) 1.67 (m, 2H), 1.81 (m, 4H), 2.18 (m, 2H), 2.49 (m, 41H), 2.84 (t, 2H, J=7.35 Hz), 3.12 (m, 2H), 3.94 (m, 6H), 4.41 (m, 1H), 6.29 (s, 1H), 8.91 (d, 1H, J=8.34 Hz), 7.05 (m, 2H), 7.12 (m, 2H), 7.29 (m, 1H), 7.41 (d, 1H, J=1.92 Hz).

EXAMPLE 87

Preparation of 1,2-Dimethoxy-4-(5-{4-[4-benzylpiperazinyl]butyl}isoxazol-3-yl)benzene About 2 min after dissolving 3-[3-(3,4-dimethoxyphenyl)isoxazol-5-yl]butanal (32 mg, 0.116 mmol) and 1-benzylpiperazine (20, 0.116 mmol) in 2 mL of dry methylene chloride, were added NaBH(OAc)$_3$ (73.8 mg, 0.348 mmol), cold acetic acid (8.0, 0.139 mmol) and molecular sieves (5 beads). The reaction mixture was reacted for 4.5 hr and followed the same processes as in Example 1 to obtain 35.7 mg (70.7%) of the target compound.

$^1$H NMR (300 MHz, CDCl$_3$) 1.57 (m, 2H), 1.75 (m, 2H), 2.39 (t, 2H, J=7.41 Hz), 2.49 (br s, 8H), 2.80 (t, 2H, J=7.44 Hz), 3.51 (s, 2H), 3.92 (m, 6H), 6.25 (s, 1H), 6.90 (d, 1H, J=8.37 Hz), 7.28 (m, 6H), 7.40 (d, 1H, J=1.77 Hz); $^{13}$C NMR (150 MHz, CDCl$_3$) 26.14, 26.82, 27.28, 53.53, 53.82, 56.59, 58.64, 63.58, 99.36, 110.25, 111.90, 120.45, 122.89, 127.66, 128.80, 129.78, 138.69, 150.04, 151.21, 162.69, 174.27.

EXAMPLE 88

Preparation of 2-(5-{4-[4-(Diphenylmethyl)piperazinyl]butyl}isoxazol-3-yl)thiophene About 2 min after dissolving 3-(3-(2-thienyl)isoxazol-5-yl)butanal (14 mg, 0.063 mmol) and 1-(diphenylmethyl)piperazine (15.9 mg, 0.063 mmol) in 2 mL of dry methylene chloride, were added NaBH(OAc)$_3$ (40.1 mg, 0.189 mmol), cold acetic acid (4.4, 0.077 mmol) and molecular sieves (5 beads). The reaction mixture was reacted for 17 hr and followed the same processes as in Example 1 to obtain 5.5 mg (19.1%) of the target compound.

$^1$H NMR (300 MHz, CDCl$_3$) 1.64 (m, 2H), 1.76 (m, 2H), 2.48 (m, 10H), 2.80 (t, 2H, J=7.68 Hz), 4.24 (s, 1H), 6.24 (s, 1H), 7.11 (m, 1H), 7.17 (m, 2H), 7.27 (t, 6H, J=7.47 Hz), 7.42 (d, 4H).

EXAMPLE 89

Preparation of 2-(5-{4-[4-Benylpiperazinyl]butyl}isoxazol-3-yl)thiophene

About 2 min after dissolving 3-(3-(2-thienyl)isoxazol-5-yl)butanal (21 mg, 0.095 mmol) and 1-benzylpiperazine (16.5, 0.095 mmol) in 2 mL of dry methylene chloride, were added NaBH(OAc)$_3$ (60.4 mg, 0.285 mmol), cold acetic acid (6.5, 0.114 mmol) and molecular sieves (5 beads). The reaction mixture was reacted for 4.2 hr and followed the same processes as in Example 1 to obtain 13.9 mg (81.0%) of the target compound.

$^1$H NMR (300 MHz, CDCl$_3$) 1.61 (m, 2H), 1.76 (m, 2H), 2.42 (t, 2H, J=7.62 Hz), 2.52 (br s, 8H), 2.80 (t, 2H, J=7.14 Hz), 3.53 (s, 2H), 6.23 (s, 1H), 7.12 (t, 1H), 7.28 (m, 5H), 7.42 (m, 2H); $^{13}$C NMR (150 MHz, CDCl$_3$) 26.09, 26.61, 27.23, 53.27, 53.73, 58.55, 63.55, 99.80, 116.56, 127.78, 127.84, 127.96, 128.22, 128.95, 129.91, 131.93, 158.25.

EXAMPLE 90

Preparation of 1-(5-{4-[4-Benzylpiperazinyl]butyl}isoxazol-3-yl)-3-phenoxybenzene About 2 min after dissolving 3-[3-(3-phenoxyphenyl)isoxazol-5-yl]butanal (31 mg, 0.101 mmol) and 1-benzylpiperazine (17.6, 0.101 mmol) in 2 mL of dry methylene chloride, were added NaBH(OAc)$_3$ (64.2 mg, 0.303 mmol), cold acetic acid (6.9, 0.121 mmol) and molecular sieves (5 beads). The reaction mixture was reacted for 17 hr and followed the same processes as in Example 1 to obtain 20.1 mg (42.6%) of the target compound.

$^1$H NMR (300 MHz, CDCl$_3$) 1.60 (m, 2H), 1.75 (m, 2H), 2.40 (t, 2H, J=7.41 Hz), 2.51 (s, 8H), 2.80 (t, 2H, J=7.29 Hz), 3.52 (s, 2H), 6.25 (s, 1H), 7.10 (m, 3H), 7.34 (m, 10H), 7.52 (d, 1H).

EXAMPLE 91

Preparation of 5-{4-[4-Benzylpiperazinyl]butyl}-3-(2-phenylvinyl)isoxazole

About 2 min after dissolving 3-[3-(2-phenylvinyl)isoxazol-5-yl]butanal (15 mg, 0.062 mmol) and 1-benzylpiperidine (10.8, 0.062 mmol) in 2 mL of dry methylene chloride, were added NaBH(OAc)$_3$ (39.4 mg, 0.186 mmol), cold acetic acid (4.3, 0.074 mmol) and molecular sieves (5 beads). The reaction mixture was reacted for 3.5 hr and followed the same processes as in Example 1 to obtain 3.6 mg (14.5%) of the target compound.

$^1$H NMR (300 MHz, CDCl$_3$) 1.72 (m, 6H), 2.64 (m, 10H), 3.59 (s, 2H), 6.27 (s, 1H), 7.12 (d, 2H, J=4.08 Hz), 7.32 (m, 9H), 7.52 (d, 1H).

EXAMPLE 92

Preparation of 1-(1-{4-[3-(3-Phenoxyphenyl)isoxazol-5-yl]butyl}-4-piperidyl)-3-hydrobenzimidazol-2-on About 2 min after dissolving 3-[3-(3-phenoxyphenyl)isoxazol-5-yl]butanal (40 mg, 0.130 mmol) and 4-(2-keto-1-benzimidazolinyl)piperidine (28.3 mg, 0.130 mmol) in 2 mL of dry methylene chloride, were added NaBH(OAc)$_3$ (82.7 mg, 0.390 mmol), cold acetic acid (8.9, 0.156 mmol) and molecular sieves (5 beads). The reaction mixture was reacted for 16 hr and followed the same processes as in Example 1 to obtain 29.6 mg (70.1%) of the target compound.

$^1$H NMR (300 MHz, CDCl$_3$) 1.62 (m, 2H), 1.80 (m, 4H), 2.15 (m, 2H). 2.46 (m, 4H), 2.83 (t, 2H, J=7.2 Hz), 3.11 (m, 2H), 4.38 (m, 1H), 6.27 (s, 1H), 7.08 (m, 6H), 7.32 (m, 5H), 7.52 (m, 2H), 10.02 (br s, 1H).

EXAMPLE 93

Preparation of 1-(1-{4-[3-(2-Phenylvinyl)isoxazol-5-yl]butyl}-4-piperidyl)-3-hydrobenzimidazol-2-on About 2 min after dissolving 3-[3-(2-phenylvinyl)isoxazol-5-yl]butanal (25 mg, 0.104 mmol) and 4-(2-keto-1-benzimidazolinyl)piperidine (22.6 mg, 0.104 mmol) in 2 mL of dry methylene chloride, were added NaBH(OAc)$_3$ (66.1 mg, 0.312 mmol), cold acetic acid (7.2, 0.125 mmol) and molecular sieves (5 beads). The reaction mixture was reacted for 3.5 hr and followed the same processes as in Example 1 to obtain 29.6 mg (70.1%) of the target compound.

$^1$H NMR (300 MHz, CDCl$_3$) 1.73 (m, 6H), 2.26 (m, 2H), 2.55 (m, 4H), 2.82 (t, 2H, J=6.87 Hz), 3.19 (m, 2H), 4.43 (m, 1H), 6.27 (s, 1H), 7.08 (m, 4H), 7.33 (m, 5H), 7.51 (d, 2H, J=7.68 Hz), 9.95 (br s, 1H).

EXAMPLE 94

Preparation of 3-(4-Fluorophenyl)-5-{4-[4-benzylpiperazinyl]butyl}isoxazole

About 2 min after dissolving 3-[3-(4-fluorophenyl)isoxazol-5-yl]butanal (25 mg, 0.104 mmol) and 1-benzylpiperidine (37.2, 0.214 mmol) in 2 mL of dry methylene chloride, were added NaBH(OAc)$_3$ (136 mg, 0.642 mmol), cold acetic acid (14.7, 0.257 mmol) and molecular sieves (5 beads). The reaction mixture was reacted for 1.5 hr and followed the same processes as in Example 1 to obtain 49.2 mg (58.4%) of the target compound.

$^1$H NMR (300 MHz, CDCl$_3$) 1.59 (m, 2H), 1.76 (m, 2H), 2.39 (t, 2H, J=7.44 Hz), 2.48 (br s, 8H), 2.81 (t, 2H, J=7.26 Hz), 3.51 (s, 2H), 6.25 (s, 1H), 7.12 (t, 2H, J=8.79 Hz), 7.27 (m, 5H), 7.76 (m, 2H); $^{13}$C NMR (150 MHz, CDCl$_3$) 26.11, 26.87, 27.25, 53.58, 53.84, 58.63, 63.61, 99.39, 116.44, 116.56, 126.31, 127.63, 128.79, 129.21, 129.26, 129.75, 138.74, 161.98, 163.49, 165.14, 174.68.

EXAMPLE 95

Preparation of 3-(3-Nitrophenyl)-5-{4-[4-benzylpiperazinyl]butyl}isoxazole

About 2 min after dissolving 3-[3-(3-nitrophenyl)isoxazol-5-yl]butanal (50 mg, 0.192 mmol) and 1-benzylpiperidine (33.4, 0.192 mmol) in 3 mL of dry methylene chloride, were added NaBH(OAc)$_3$ (122 mg, 0.576 mmol), cold acetic acid (13.2, 0.230 mmol) and molecular sieves (5 beads). The reaction mixture was reacted for 1.5 hr and followed the same processes as in Example 1 to obtain 74.6 mg (92.4%) of the target compound.

$^1$H NMR (300 MHz, CDCl$_3$) 1.60 (m, 2H), 1.78 (m, 2H), 2.40 (t, 2H, J=7.41 Hz), 2.49 (br s, 8H), 2.85 (t, 2H, J=7.35 Hz), 3.51 (s, 2H), 6.39 (s, 1H), 7.28 (m, 5H), 7.63 (t, 1H, J=7.95 Hz), 8.16 (d, 1H, J=7.77 Hz), 8.27 (d, 1H), 8.58 (s, 1H); $^{13}$C NMR (150 MHz, CDCl$_3$) 26.09, 26.84, 27.28, 53.58, 53.84, 58.55, 63.58, 99.46, 122.29, 124.91, 127.60, 128.77, 129.75, 130.53, 131.85, 132.99, 138.74, 149.29, 161.05, 175.64.

EXAMPLE 96

Preparation of 2,4-Dimethoxy-1-(5-{4-[4-benzylpiperazinyl]butyl}isoxazol-3-yl)benzene About 2 min after dissolving 3-[3-(43-dimethoxyphenyl)isoxazol-5-yl]butanal (15.5 mg, 0.056 mmol) and 1-benzylpiperidine (9.7, 0.056 mmol) in 2 mL of dry methylene chloride, were added NaBH(OAc)$_3$ (35.6 mg, 0.168 mmol), cold acetic acid (3.8, 0.067 mmol) and molecular sieves (5 beads). The reaction mixture was reacted for 2 hr and followed the same processes as in Example 1 to obtain 19.1 mg (78.3%) of the target compound.

$^1$H NMR (300 MHz, CDCl$_3$) 1.60 (m, 2H), 1.76 (m, 2H), 2.42 (m, 10H), 2.79 (t, 2H, J=7.20 Hz), 3.51 (s, 2H), 3.85 (m, 6H), 6.43 (s, 1H), 6.57 (m, 2H), 7.28 (m, 5H), 7.80 (d, 1H).

Example 97

Preparation of 1-(1-{4-[3-(2,4-Dimethoxyphenyl)isoxazol-5-yl]butyl}-4-piperidyl)-3-hydrobenzimidazol-2-on About 2 min after dissolving 3-[3-(2,4-dimethoxyphenyl)isoxazol-5-yl]butanal (13.5 mg, 0.049 mmol) and 4-(2-keto-1-benzimidazolinyl)piperidine (10.6 mg, 0.049 mmol) in 2 mL of dry methylene chloride, were added NaBH(OAc)$_3$ (31.2 mg, 0.147 mmol), cold acetic acid (3.4, 0.059 mmol) and molecular sieves (5 beads). The reaction mixture was reacted for 2.1 hr and followed the same processes as in Example 1 to obtain 18.1 mg (77.50%) of the target compound.

$^1$H NMR (300 MHz, CDCl$_3$) 1.67 (m, 2H), 1.81 (m, 4H), 2.21 (m, 2H), 2.51 (m, 4H), 2.83 (t, 2H, J=7.2 Hz), 3.14 (m, 2H), 3.87 (m, 6H), 4.42 (m, 1H), 6.47 (s, 1H), 6.56 (m, 2H), 7.08 (m, 3H), 7.32 (s, 1H), 7.81 (d, 1H, J=8.46 Hz), 9.89 (br s, 1H).

EXAMPLE 98

Preparation of 3-Phenyl-5-{4-[4-benzylpiperazinyl]butyl}isoxazole

About 2 min after dissolving 3-(3-phenylisoxazol-5-yl)butanal (38 mg, 0.177 mmol) and 1-benzylpiperidine (30.8, 0.177 mmol) in 2 mL of dry methylene chloride, were added NaBH(OAc)$_3$ (113 mg, 0.531 mmol), cold acetic acid (12.1, 0.212 mmol) and molecular sieves (5 beads). The reaction mixture was reacted for 3.5 hr and followed the same processes as in Example 1 to obtain 10.9 mg (16.4%) of the target compound.

$^1$H NMR (300 MHz, CDCl$_3$) 1.62 (m, 2H), 1.76 (m, 2H), 2.48 (m, 10H), 2.82 (t, 2H, J=7.41 Hz), 3.53 (s, 2H), 6.30 (s, 1H), 7.29 (m, 5H), 7.44 (m, 3H), 7.78 (m, 2H).

EXAMPLE 99

Preparation of 3-(4-Fluorophenyl)-5-[4-(4-phenylpiperazinyl)butyl]isoxazole

About 2 min after dissolving 3-[3-(4-fluorophenyl)isoxazol-5-yl]butanal (57 mg, 0.244 mmol) and 1-benzylpiperidine (37.3, 0.244 mmol) in 3 mL of dry methylene chloride, were added NaBH(OAc)$_3$ (155 mg, 0.732 mmol), cold acetic acid (16.8, 0.293 mmol) and molecular sieves (5 beads). The reaction mixture was reacted for 2 hr and followed the same processes as in Example 1 to obtain 56.7 mg (61.2%) of the target compound.

$^1$H NMR (300 MHz, CDCl$_3$) 1.65 (m, 2H), 1.81 (m, 2H), 2.45 (t, 2H, J=7.2 Hz), 2.61 (t, 4H, J=4.77 Hz), 2.84 (t, 2H, J=7.14 Hz), 3.21 (t, 4H, J=5.28 Hz), 6.28 (s, 1H), 6.90 (m, 3H), 7.14 (t, 2H, J=8.73 Hz), 7.27 (t, 2H, J=8.46 Hz), 7.78 (m, 2H); $^{13}$C NMR (150 MHz, CDCl$_3$) 26.14, 26.87, 27.31, 49.72, 53.92, 58.66, 99.46, 116.49, 116.67, 120.30, 126.33, 129.26, 129.31, 129.73, 151.98, 162.06, 163.54, 165.20, 174.71.

EXAMPLE 100

Preparation of 3-(3-Nitrophenyl)-5-[4-(4-phenylpiperazinyl)butyl]isoxazole

About 2 min after dissolving 3-[3-(3-nitrophenyl)isoxazol-5-yl]butanal (38.8 mg, 0.149 mmol) and 1-benzylpiperidine (22.8, 0.149 mmol) in 3 mL of dry methylene chloride, were added NaBH(OAc)$_3$ (94.7 mg, 0.447 mmol), cold acetic acid (10.2, 0.179 mmol) and molecular sieves (5 beads). The reaction mixture was reacted for 3.5 hr and followed the same processes as in Example 1 to obtain 32.8 mg (54.2%) of the target compound.

$^1$H NMR (300 MHz, CDCl$_3$) 1.67 (m, 2H), 1.84 (m, 2H), 2.48 (t, 2H, J=7.62 Hz), 2.63 (t, 4H, J=4.95 Hz), 2.89 (t, 2H, J=7.41 Hz), 3.23 (t, 4H, J=4.95 Hz), 6.42 (s, 1H), 6.86 (t, 1H), 6.93 (d, 2H, J=8.31 Hz), 7.26 (t, 2H, J=7.95 Hz), 7.65 (t, 1H), 8.17 (d, 1H), 8.28 (d, 1H), 8.60 (s, 1H).

EXAMPLE 101

Preparation of 1,2-Dimethoxy-4-{5-[4-(4-phenylpiperazinyl)butyl]isoxazol-3-yl}benzene About 2 min after dissolving 3-[3-(3,4-dimethoxyphenyl)isoxazol-5-yl]butanal (55 mg, 0.200 mmol) and 1-benzylpiperidine (30.6, 0.200 mmol) in 3 mL of dry methylene chloride, were added NaBH(OAc)$_3$ (127 mg, 0.600 mmol), cold acetic acid (13.7, 0.240 mmol) and molecular sieves (5 beads). The reaction mixture was reacted for 2 hr and followed the same processes as in Example 1 to obtain 79.5 mg (100%) of the target compound.

$^1$H NMR (300 MHz, CDCl$_3$) 1.65 (m, 2H), 1.79 (m, 2H), 2.46 (t, 2H), 2.62 (t, 4H, J=4.89 Hz), 2.82 (t, 2H), 3.22 (t, 4H, J=4.65 Hz), 3.93 (d, 6H, J=7.47 Hz), 6.27 (s, 1H), 6.88 (m, 4H), 7.26 (t, 3H, J=7.41 Hz), 7.41 (s, 1H); $^{13}$C NMR (150 MHz, CDCl$_3$) 25.89, 26.54, 27.06, 49.35, 53.59, 56.33, 56.38, 58.42, 99.25, 109.63, 111.45, 116.43, 120.13, 120.23, 122.46, 129.52, 129.66, 149.65, 150.84, 151.61, 162.46, 174.03.

EXAMPLE 102

Preparation of 2,4-Dimethoxy-1-{5-[4-(4-phenylpiperazinyl)butyl]isoxazol-3-yl}benzene About 2 min after dissolving 3-[3-(2,4-dimethoxyphenyl)isoxazol-5-yl]butanal (13 mg, 0.047 mmol) and 1-benzylpiperidine (7.2, 0.047 mmol) in 2 mL of dry methylene chloride, were added NaBH(OAc)$_3$ (30 mg, 0.141 mmol), cold acetic acid (3.2, 0.056 mmol) and molecular sieves (5 beads). The reaction mixture was reacted for 3 hr and followed the same processes as in Example 1 to obtain 14.2 mg (84.0%) of the target compound.

$^1$H NMR (300 MHz, CDCl$_3$) 1.67 (m, 2H), 1.81 (m, 2H), 2.46 (t, 2H, J=7.41 Hz), 2.63 (t, 4H, J=5.07 Hz), 2.83 (t, 2H, J=7.2 Hz), 3.22 (t, 4H, J=4.95 Hz), 3.86 (m, 6H), 6.46 (s, 1H), 6.56 (m, 2H), 6.90 (m, 3H), 7.82 (d, 1H, J=8.46 Hz), 7.27 (m, 2H).

EXAMPLE 103

Preparation of 2-{5-[4-(4-Phenylpiperazinyl)butyl]isoxazol-3-yl}thiophene

About 2 min after dissolving 3-(3-(2-thienyl)isoxazol-5-yl)butanal (23.5 mg, 0.106 mmol) and 1-phenylpiperidine (16.2, 0.106 mmol) in 2 mL of dry methylene chloride, were added NaBH(OAc)$_3$ (67.4 mg, 0.318 mmol), cold acetic acid (7.3, 0.127 1mmol) and molecular sieves (5 beads). The reaction mixture was reacted for 3 hr and followed the same processes as in Example 1 to obtain 36.9 mg (94.7%) of the target compound.

$^1$H NMR (300 MHz, CDCl$_3$) 1.65 (m, 2H), 1.80 (m, 2H), 2.46 (t, 2H, J=7.41 Hz), 2.62 (t, 4H, J=4.92 Hz), 2.83 (t, 2H, J=7.14 Hz), 3.22 (t, 4H, J=4.89Hz), 6.25 (s, 1H), 6.88 (m, 3H), 7.11 (m, 1H), 7.27 (t, 2H, J=8.01 Hz), 7.42 (m, 2H).

EXAMPLE 104

Preparation of 3-Phenyl-5-[4-(4-phenylpiperazinyl)butyl]isoxazole

About 2 min after dissolving 3-(3-phenyl)isoxazol-5-yl)butanal (45.3 mg, 0.210 mmol) and 1-phenylpiperidine (32.1, 0.210 mmol) in 3 mL of dry methylene chloride, were added NaBH(OAc)$_3$ (134 mg, 0.630 mmol), cold acetic acid (14.4, 0.252 mmol) and molecular sieves (5 beads). The reaction mixture was reacted for 3.5 hr and followed the same processes as in Example 1 to obtain 15.0 mg (19.8%) of the target compound.

$^1$H NMR (300 MHz, CDCl$_3$) 1.67 (m, 2H), 1.82 (m, 2H), 2.48 (t, 2H, J=7.47 Hz), 2.64 (t.s, 4H, J=4.77 Hz), 2.86 (t, 2H, J=7.14 Hz), 3.23 (t.s, 4H, J=4.65 Hz), 6.32 (s, 1H), 6.91 (m, 3H), 7.27 (m, 2H), 7.45 (m, 3H), 7.79 (m, 2H).

EXAMPLE 105

Preparation of 1-(4-{4-[3-(4-Fluorophenyl)isoxazol-5-yl]butyl}piperazinyl)-2-methoxybenzene About 2 min after dissolving 3-[3-(4-fluorophenyl)isoxazol-5-yl]butanal (70 mg, 0.300 mmol) and 1-(2-methoxyphenyl)piperidine (57.7 mg, 0.300 mmol) in 3 mL of dry methylene chloride, were added NaBH(OAc)$_3$ (191 mg, 0.900 mmol), cold acetic acid (20.6, 0.360 mmol) and molecular sieves (5 beads). The reaction mixture was reacted for 3 hr and followed the same processes as in Example 1 to obtain 96.8 mg (78.8%) of the target compound.

$^1$H NMR (300 MHz, CDCl$_3$) 1.63 (m, 2H), 1.79 (m, 2H), 2.45 (t, 2H, J=7.41 Hz), 2.65 (br s, 4H), 2.82 (t, 2H, J=7.14 Hz), 3.10 (br s, 4H), 3.84 (s, 3H), 6.26 (s, 1H), 6.88 (m, 4H), 7.12 (m, 2H), 7.77 (m, 2H); $^{13}$C NMR (150 MHz, CDCl$_3$) 26.09, 26.79, 27.23, 51.14, 54.05, 55.91, 58.66, 99.36, 112.06, 116.36, 116.51, 118.79, 121.62, 123.40, 126.25, 129.23, 142.01, 152.94, 161.93, 163.41, 165.07, 174.65.

EXAMPLE 106

Preparation of 2-Methoxy-1-(4-{4-[3-(3-Nitrophenyl)isoxazol-5-yl]butyl}piperazinyl)benzene About 2 min after dissolving 3-[3-(3-nitrophenyl)isoxazol-5-yl]butanal (60 mg, 0.231 mmol) and 1-(2-methoxyphenyl)piperidine (44.4 mg, 0.231 mmol) in 3 mL of dry methylene chloride, were added NaBH(OAc)$_3$ (147 mg, 0.693 mmol), cold acetic acid (15.9, 0.277 mmol) and molecular sieves (5 beads). The reaction mixture was reacted for 4.2 hr and followed the same processes as in Example 1 to obtain 80.8 mg (80.1%) of the target compound.

$^1$H NMR (300 MHz, CDCl$_3$) 1.66 (m, 2H), 1.82 (m, 2H), 2.47 (t, 2H, J=7.47 Hz), 2.66 (br s, 4H), 2.87 (t, 2H, J=7.41 Hz), 3.10 (br s, 4H), 3.84 (s, 3H), 6.41 (s, 1H), 6.91 (m, 4H), 7.63 (t, 1H, J=8.16 Hz), 8.15 (d, 1H, J=7.74 Hz), 8.26 (d, 1H), 8.59 (s, 1H).

EXAMPLE 107

Preparation of 1-(4-{4-[3-(3,4-Dimethoxyphenyl)isoxazol-5-yl]butyl}piperazinyl)-2-methoxybenzene About 2 min after dissolving 3-[3-(3,4-dimethoxyphenyl)isoxazol-5-yl]butanal (33.2 mg, 0.121 mmol) and 1-(2- methoxyphenyl)piperidine (23.3 mg, 0.121 mmol) in 2 mL of dry methylene chloride, were added NaBH(OAc)$_3$ (76.9 mg, 0.363 mmol), cold acetic acid (8.3, 0.145 mmol) and molecular sieves (5 beads). The reaction mixture was reacted for 3 hr and followed the same processes as in Example 1 to obtain 33.2 mg (60.8%) of the target compound.

$^1$H NMR (300 MHz, CDCl$_3$) 1.66 (m, 2H), 1.81 (m, 2H), 2.50 (t, 2H), 2.70 (s, 4H), 2.83 (t, 2H, J=7.41 Hz), 3.12 (s, 4H), 3.86 (m, 3H), 3.93 (d, 6H, J=7.26 Hz), 6.28 (s, 1H), 6.92 (m, 5H), 7.26 (d, 1H), 7.41 (d, 1H, J=1.92 Hz).

EXAMPLE 108

Preparation of 1-(4-{4-[3-(2,4-Dimethoxyphenyl) isoxazol-5-yl]butyl}piperazinyl)-2-methoxybenzene About 2 min after dissolving 3-[3-(2,4-dimethoxyphenyl)isoxazol-5-yl]butanal (15 mg, 0.054 mmol) and 1-(2-methoxyphenyl)piperidine (10.4 mg, 0.054 mmol) in 2 mL of dry methylene chloride, were added NaBH(OAc)$_3$ (34.3 mg, 0.167 mmol), cold acetic acid (3.7, 0.065 mmol) and molecular sieves (5 beads). The reaction mixture was reacted for 3 hr and followed the same processes as in Example 1 to obtain 15.0 mg (61.5%) of the target compound.

$^1$H NMR (300 MHz, CDCl$_3$) 1.67 (m, 2H), 1.81 (m, 2H), 2.49 (t, 2H), 2.69 (s, 4H), 2.83 (t, 2H, J=7.35 Hz), 3.12 (s, 4H), 3.86 (m, 9H), 6.45 (s, 1H), 6.55 (m, 2H), 6.94 (m, 4H), 7.81 (d, 1H, J=8.46 Hz).

EXAMPLE 109

Preparation of 2-Methoxy-1-{4-(3-(2-thienyl) isoxazol-5-yl)butyl}piperazinyl}benzene About 2 min after dissolving 3-(3-(2-thienyl)isoxazol-5-yl)butanal (21 mg, 0.095 mmol) and 1-(2-methoxyphenyl)piperidine (18.3 mg, 0.095 mmol) in 2 mL of dry methylene chloride, were added NaBH(OAc)$_3$ (60.4 mg, 0.285 mmol), cold acetic acid (6.5 0.114 mmol) and molecular sieves (5 beads). The reaction mixture was reacted for 3 hr and followed the same processes as in Example 1 to obtain 23.4 mg (62.0%) of the target compound.

$^1$H NMR (300 MHz, CDCl$_3$) 1.65 (m, 2H), 1.79 (m, 2H), 2.49 (t, 2H, J=7.47 Hz), 2.69 (s, 4H), 2.82 (t, 2H, J=7.32 Hz), 3.12 (s, 4H), 3.86 (s, 3H), 6.25 (s, 1H), 6.93 (m, 4H), 7.10 (m, 1H), 7.42 (m, 2H).

EXAMPLE 110

Preparation of 2-Methoxy-1-{4-[4-(3-phenylisoxazol-5-yl)butyl]piperazinyl}benzene About 2 min after dissolving 3-(3-phenylisoxazol-5-yl)butanal (36 mg, 0. 167 mmol) and 1-(2-methoxyphenyl)piperidine (32.1 mg, 0.167 mmol) in 2 mL of dry methylene chloride, were added NaBH(OAc)$_3$ (106 mg, 0.501 mmol), cold acetic acid (11.4, 0.200 mmol) and molecular sieves (5 beads). The reaction mixture was reacted for 3 hr and followed the same processes as in Example 1 to obtain 11.5 mg (17.6%) of the target compound.

$^1$H NMR (300 MHz, CDCl$_3$) 1.69 (m, 2H), 1.82 (m, 2H), 2.52 (t, 2H). 2.72 (s, 4H), 2.86 (t, 2H, J=7.14 Hz), 3.14 (s, 4H), 3.86 (s, 3H), 6.32 (s, 1H), 6.94 (m, 4H), 7.44 (m, 3H), 7.78 (m, 2H).

EXAMPLE 111

Preparation of 3-Phenoxy-1-{5-[4-(4-phenylpiperazinyl)butyl]isoxazol-3-yl}benzene About 2 min after dissolving 3-[3-(3-phenoxyphenyl)isoxazol-5-yl]butanal (65 mg, 0.211 mmol) and 1-phenylpiperidine (32.2, 0.211 mmol) in 3 mL of dry methylene chloride, were added NaBH(OAc)$_3$ (134 mg, 0.633 mmol), cold acetic acid (14.5, 0.253 mmol) and molecular sieves (5 beads). The reaction mixture was reacted for 3.5 hr and followed the same processes as in Example 1 to obtain 37.1 mg (38.8%) of the target compound.

$^1$H NMR (300 MHz, CDCl$_3$) 1.65 (m, 2H), 1.80 (m, 2H), 2.46 (t, 2H, J=7.44 Hz), 2.62 (t.s, 4H, J=4.95 Hz), 2.84 (t, 2H, J=7.14 Hz), 3.22 (t.s, 4H, J=5.01 Hz), 6.27 (s, 1H), 6.89 (m, 3H), 7.08 (m, 3H), 7.35 (m, 7H), 7.53 (d, 1H).

EXAMPLE 112

Preparation of 5-[4-(4-Phenylpiperazinyl)butyl]-3-(2-phenylvinyl)isoxazole

About 2 min after dissolving 3-[3-(2-phenylvinyl)isoxazol-5-yl]butanal (20.5 mg, 0.085 mmol) and 1-phenylpiperidine (13.0, 0.085 mmol) in 3 mL of dry methylene chloride, were added NaBH(OAc)$_3$ (54 mg, 0.255 mmol), cold acetic acid (5.8 0.102 mmol) and molecular sieves (5 beads). The reaction mixture was reacted for 3.5 hr and followed the same processes as in Example 1 to obtain 11.0 mg (33.4%) of the target compound.

$^1$H NMR (300 MHz, CDCl$_3$) 1.68 (m, 2H), 1.81 (m, 2H), 2.52 (t, 2H), 2.67 (t, 4H, J=4.74 Hz), 2.82 (t, 2H, J=7.14 Hz), 3.26 (t, 4H, J=4.86 Hz), 6.26 (s, 1H), 6.92 (m, 3H), 7.13 (s, 2H), 7.34 (m, 5H), 7.52 (dd, 2H).

EXAMPLE 113

Preparation of 1-(5-{4-[4-(2-Methoxyphenyl) piperazinyl]butyl}isoxazol-3-yl)-3-phenoxylbenzene About 2 min after dissolving 3-[3-(3-phenoxyphenyl)isoxazol-5-yl]butanal (61 mg, 0.198 mmol) and 1-(2-methoxyphenyl)piperidine (38 mg, 0.198 mmol) in 3 mL of dry methylene chloride, were added NaBH(OAc)$_3$ (126 mg, 0.594 mmol), cold acetic acid (13.6, 0.238 mmol) and molecular sieves (5 beads). The reaction mixture was reacted for 3 hr and followed the same processes as in Example 1 to obtain 38.4 mg, (40.1%) of the target compound.

$^1$H NMR (300 MHz, CDCl$_3$) 1.64 (m, 2H), 1.78 (m, 2H), 2.47 (t, 2H, J=7.26 Hz). 2.67 (s, 4H), 2.83 (t, 2H, J=7.14 Hz), 3.12 (s, 4H), 3.86 (s, 3H), 6.27 (s, 1H), 7.00 (m, 8H), 7.38 (m, 4H), 7.53 (d, 1H).

EXAMPLE 114

Preparation of 2-Methoxy-1-(4-{4-[3-(2-Phenylvinyl)iosxazol-5-yl]butyl}piperazinyl) benzene About 2 min after dissolving 3-[3-(2-phenylvinyl)isoxazol-5-yl]butanal (14.5 mg, 0.060 mmol) and 1-(2-methoxyphenyl)piperidine (11.5 mg, 0.060 mmol) in 3 mL of dry methylene chloride, were added NaBH(OAc)$_3$ (38.1 mg, 0.180 mmol), cold acetic acid (4.1, 0.072 mmol) and molecular sieves (5 beads). The reaction mixture was reacted for 3.5 hr and followed the same processes as in Example 1 to obtain 15.0 mg (59.9%) of the target compound.

$^1$H NMR (300 MHz, CDCl$_3$) 1.76 (m, 4H), 2.08 (m, 2H), 2.82 (t, 2H, J=6.99 Hz), 3.17 (m, 4H), 3.86 (s, 3H), 6.27 (s, 1H), 6.93 (m, 4H), 7.13 (m, 1H), 7.36 (m, 4H), 7.52 (m, 2H).

EXAMPLE 115

Preparation of 3-(4-Fluorophenyl)-5-{4-[4-(4-fluorophenyl)piperazinyl]butyl}isoxazole About 2 min after dissolving 3-[3-(4- fluorophenyl)isoxazol-5-yl]butanal (32.2 mg, 0.138 mmol) and 1-(4- fluorophenyl)piperidine (22.5 mg, 0.125 mmol) in 2 mL of dry methylene chloride, were added NaBH(OAc)$_3$ (79.5 mg, 0.375 mmol) and molecular sieves (5 beads). The reaction mixture was reacted for 3 hr and followed the same processes as in Example 1 to obtain 15.8 mg (31.8%) of the target compound.

$^1$H NMR (300 MHz, CDCl$_3$) 1.65 (m, 2H), 1.81 (m, 2H), 2.46 (m, 21H), 2.62 (m, 4H), 2.85 (m, 2H), 3.13 (m, 4H), 6.27 (s, 1H), 6.89 (m, 4H), 7.13 (m, 2H), 7.77 (m, 2H).

EXAMPLE 116

Preparation of 3-Methoxy-1-(4-{4-[3-(3-nitrophenyl)isoxazol-5-yl]butyl}piperazinyl)benzene About 2 min after dissolving 3-[3-(3-nitrophenyl) isoxazol-5-yl]butanal (32.8 mg, 0.126 mmol) and 1-(3-methoxyphenyl)piperidine (22.1 mg, 0.115 mmol) in 2 mL of dry methylene chloride, were added NaBH(OAc)$_3$ (73.1 mg, 0.345 mmol) and molecular sieves (5 beads). The reaction mixture was reacted for 3 hr and followed the same processes as in Example 1 to obtain 30.0 mg (79.7%) of the target compound.

$^1$H NMR (300 MHz, CDCl$_3$) 1.66 (m, 2H), 1.84 (m, 2H), 2.46 (m, 2H), 2.61 (m, 4H), 2.89 (m, 2H), 3.21 (m, 4H), 3.79 (s, 3H), 6.44 (m, 3H), 6.53 (m, 1H), 7.17 (t, 1H), 7.66 (t, 1H), 8.18 (d, 1H), 8.28 (d, 1H), 8.61 (s, 1H).

EXAMPLE 117

Preparation of 5-{4-[4-(2-Fluorophenyl)piperazinyl] butyl}-3-(2-phenylvinyl)isoxazole About 2 min after dissolving 3-[3-(2-phenylvinyl) isoxazol-5-yl]butanal (37.4 mg, 0.155 mmol) and 1-(2-fluorophenyl)piperidine (25.4 mg, 0.141 mmol) in 2 mL of dry methylene chloride, were added NaBH(OAc)$_3$ (89.7 mg, 0.423 mmol) and molecular sieves (5 beads). The reaction mixture was reacted for 3.5 hr and followed the same processes as in Example 1 to obtain 18.0 mg (31.5%) of the target compound.

$^1$H NMR (300 MHz, CDCl$_3$) 1.65 (m, 2H), 1.78 (m, 2H), 2.48 (m, 2H), 2.66 (m, 4H), 2.82 (m, 2H), 3.20 (m, 4H), 6.25 (s, 1H), 7.02 (m, 6H), 7.35 (m, 3H), 7.52 (m, 2H).

EXAMPLE 118

Preparation of 1,2-Dimethoxy-4-(5-{4-[4-(2-methylphenyl)piperazinyl]butyl}isoxazol-3-yl) benzene About 2 min after dissolving 3-[3-(3,4-dimethoxyphenyl) isoxazol-5-yl]butanal (34.4 mg, 0.125 mmol), 1-(2-methylphenyl)piperidine HCl (24.2 mg, 0.114 mmol) and diisopropylethyl amine (19.9, 0.114 mmol) in 2 mL of dry methylene chloride, were added NaBH(OAc)$_3$ (72.5 mg, 0.342 mmol) and molecular sieves (5 beads). The reaction mixture was reacted for 3 hr and followed the same processes as in Example 1 to obtain 30.5 mg (61.4%) of the target compound.

$^1$H NMR (300 MHz, CDCl$_3$) 1.65 (m, 2H), 1.78 (m, 2H), 2.30 (s, 3H), 2.45 (m, 2H), 2.63 (m, 4H), 2.84 (m, 2H), 2.96 (m, 4H), 3.93 (m, 6H), 6.28 (s, 1H), 7.02 (m, 3H), 7.15 (m, 2H), 7.28 (m, 1H), 7.42 (d, 1H, J=1.92 Hz).

The novel compound of the present invention represented by formula (1) can be prepared in various preparation forms. Hereunder is given some examples of preparation forms containing the compound of the present invention represented by formula (1) as active components. However, they should not be construed as limiting the scope of the present invention.

Preparation 1: Tablet (Direct Pressurization)

After sieving 5.0 mg of the active component, 14.1 mg of lactose, 0.8 mg of crosphobidone USNF and 0.1 mg of magnesium stearate were mixed and pressurized to a tablet form.

Preparation 2: Tablet (Wet Fabrication)

After sieving 5.0 mg of the active component, 16.0 mg of lactose and 4.0 mg, of starch were mixed. After adding an adequate amount of the solution obtained by dissolving, 800.3 mg of polysolbate in pure water, the same was particulated. After drying and sieving the particulate, 2.7 mg of colloidal silicon dioxide and 2.0 mg of magnesium stearate were mixed. Then, the particulate was pressurized to a tablet form.

Preparation 3: Powder and Capsule

After sieving 5.0 mg of active component, 14.8 mg of lactose, 10.0 mg of polyvinylpyrrolidone and 0.2 mg of magnesium stearate were mixed. The mixture was filled in a hard gelatin capsule using an adequate device.

Preparation 4: Parenteral Injection

With 100 mg of the active component, 180 mg of mainitol, 26 mg of Na$_2$HPO$_4$ 12H$_2$O and 2974 mg of distilled water, a parenteral injection was prepare.

Experimental Example: Test for the Binding Affinity to Dopamine Receptor

Binding affinities of the compounds for dopamine receptors were determined indirectly by their ability to displace radiolabeled ligand from cloned human dopamine receptors. Compounds were incubated in receptor suspension to compete with the radiolabeled ligand. The receptor-bound radiolabeled ligand was separated by filtering through Wallac glass fiber filtermat (GF/C) using Inotech cell harvester of 96-well format. The radioactivity bound to filter was counted by Micro-P counter (Wallac).

The aliquots of cloned human dopamine receptors stored at −70° C. were suspended in assay buffer and the content of receptor in each aliquot was determined by Bio-Rad DC protein assay kit to give an optimal protein (receptor) concentration obtained by preliminary receptor binding assay. Receptor suspension adjusted to optimal concentration was aliquoted in proper volume for assay and stored at −70° C. Binding assays of every compound were performed in duplicate and each different buffer solution was used for optimal assay with each subtype of dopamine receptors. Receptor binding assays were carried out in 96-well plates. Receptor suspension of 100 was incubated at 27° C. for 30–60 min in a final volume of 0.25 ml reaction mixture containing 50 of hot-ligand and 10 of test compound. First, binding affinities of test compounds toward receptors were sought at two different concentrations, 1 and 10, and then IC50 were determined for selected final compounds with high binding affinities. Haloperidol was used as the reference drug for the comparison's purpose.

After incubation, the reaction mixture was washed with ice-cold 50 mM Tris-acetate buffer by rapid filtration using a Inotech cell harvester (Inotech, Switzerland) through Whatman GF/C glass fiber filter presoaked in the assay buffer. The filter was covered with MeltiLex, sealed in a sample bag followed by drying in the microwave, and counted by MicroBeta Plus (Wallac, Finland) at a counting efficiency of 30–40%.

The following Table 1 shows some exemplary compounds used in the experiment. However, the present invention is not limited to the examples. In Table 2 and Table 3, the binding affinity (% inhibition) of the novel compounds according to the present invention to dopamine receptors and IC$_{50}$ (nM) value are presented.

TABLE 1

| Compound No. | R₁ | R₂ | n | X |
|---|---|---|---|---|
| 1 | 1,1-diphenylethyl | 3,4-dimethoxyphenyl | 3 | N |
| 2 | 1,1-diphenylethyl | 2,4-dimethoxyphenyl | 3 | N |
| 3 | 2-oxo-2,3-dihydro-1H-benzimidazol-1-yl (isopropylidene linker) | 3,4-dimethoxyphenyl | 3 | C |
| 4 | 2-oxo-2,3-dihydro-1H-benzimidazol-1-yl (isopropylidene linker) | 3-phenoxyphenyl | 3 | C |
| 5 | 2-methoxyphenyl | 4-chlorophenyl | 3 | N |
| 6 | 2-methoxyphenyl | 3-nitrophenyl | 3 | C |

TABLE 1-continued

| Compound No. | R₁ | R₂ | n | X |
|---|---|---|---|---|
| 7 | 2-methoxyphenyl | 3,4-dimethoxyphenyl | 3 | N |
| 8 | 2-methoxyphenyl | 2-thienyl | 3 | N |
| 9 | 2-methoxyphenyl | phenyl | 3 | N |
| 10 | 2-methoxyphenyl | (E)-styryl | 3 | N |
| 11 | 2-chlorophenyl | 3,4-dimethoxyphenyl | 3 | N |
| 12 | α-hydroxy-α-(4-chlorophenyl) | 4-fluorophenyl | 3 | N |
| 13 | 1-(4-chlorophenyl)-1-phenylethyl | 3,4-dimethoxyphenyl | 3 | N |

TABLE 1-continued
| Compound No. | R₁ | R₂ | n | X |
|---|---|---|---|---|
| 14 |  | 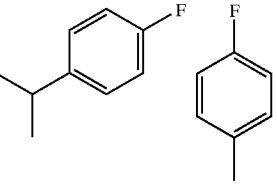 | 3 | N |
| 15 |  |  | 3 | N |
| 16 | 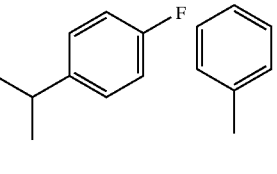 |  | 3 | N |
| 17 |  | 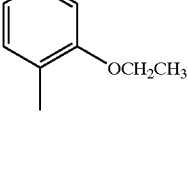 | 3 | N |
| 18 | 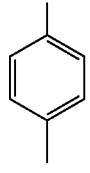 |  | 3 | N |
| 19 | 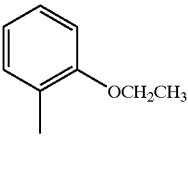 | 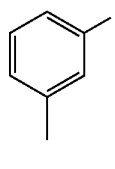 | 3 | N |
| 20 |  | 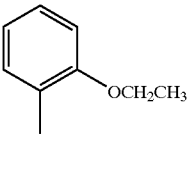 | 3 | N |

TABLE 1-continued
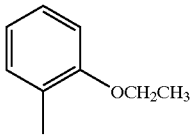
| Compound No. | R₁ | R₂ | n | X |
|---|---|---|---|---|
| 21 | 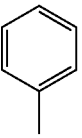 | 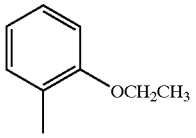 | 3 | N |
| 22 | 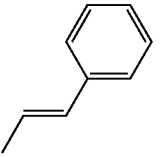 | 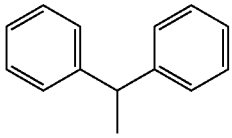 | 3 | N |
| 23 | 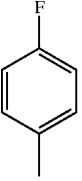 | 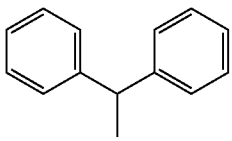 | 4 | N |
| 24 | 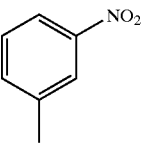 | 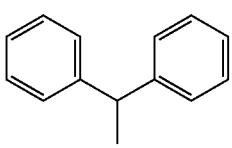 | 4 | N |
| 25 | 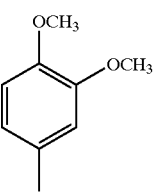 | 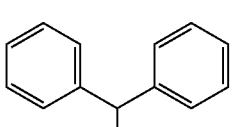 | 4 | N |
| 26 | 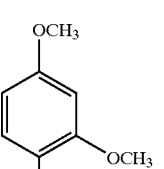 | 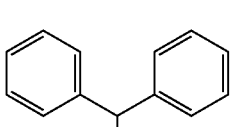 | 4 | N |
| 27 | 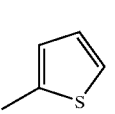 | | 4 | N |

TABLE 1-continued
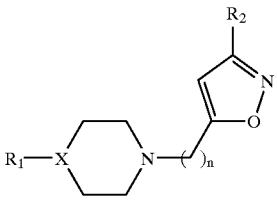
| Compound No. | R₁ | R₂ | n | X |
|---|---|---|---|---|
| 28 | 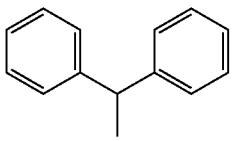 | 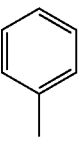 | 4 | N |
| 29 | 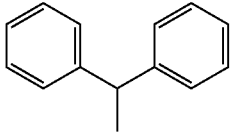 | 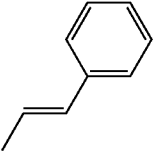 | 4 | N |
| 30 | 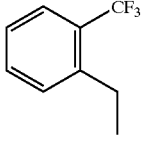 | 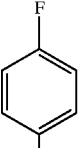 | 4 | N |
| 31 | 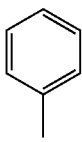 | 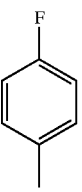 | 3 | N |
| 32 | 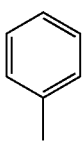 | 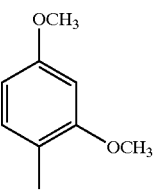 | 3 | N |
| 33 | 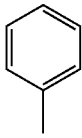 | 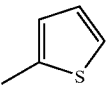 | 4 | N |
| 34 | 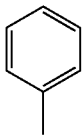 | 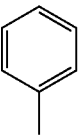 | 4 | N |

TABLE 1-continued

| Compound No. | R₁ | R₂ | n | X |
|---|---|---|---|---|
| 35 | phenyl | 3-phenoxyphenyl | 4 | N |
| 36 | phenyl | (E)-styryl (cinnamyl) | 4 | N |
| 37 | 2-methoxyphenyl | 4-fluorophenyl | 4 | N |
| 38 | 2-methoxyphenyl | 3-nitrophenyl | 4 | N |
| 39 | 2-methoxyphenyl | 3,4-dimethoxyphenyl | 4 | N |
| 40 | 2-methoxyphenyl | 2,4-dimethoxyphenyl | 4 | N |
| 41 | 2-methoxyphenyl | 2-thienyl | 4 | N |

TABLE 1-continued
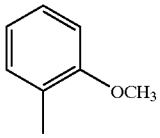
| Compound No. | R₁ | R₂ | n | X |
|---|---|---|---|---|
| 42 | 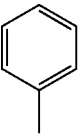 | 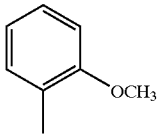 | 4 | N |
| 43 | 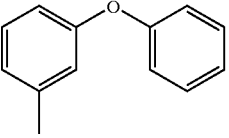 | 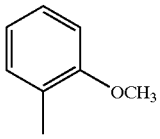 | 4 | N |
| 44 | 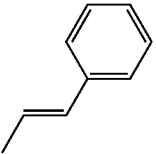 | 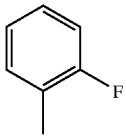 | 4 | N |
| 45 | 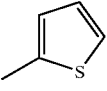 | 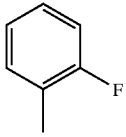 | 4 | N |
| 46 | 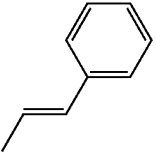 | 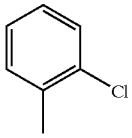 | 4 | N |
| 47 | 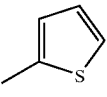 | 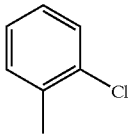 | 4 | N |
| 48 | 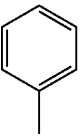 | 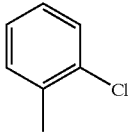 | 4 | N |
| 49 | 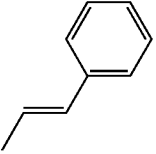 | | 4 | N |

TABLE 1-continued

General structure: R₁—X—[piperazine]—N—(CH₂)ₙ—[isoxazole with R₂ at 3-position]

| Compound No. | R₁ | R₂ | n | X |
|---|---|---|---|---|
| 50 | 1,1-bis(4-fluorophenyl)ethyl | 3,4-dimethoxyphenyl | 4 | N |
| 51 | 2-ethoxyphenyl | 3-nitrophenyl | 4 | N |
| 52 | 2-ethoxyphenyl | 3,4-dimethoxyphenyl | 4 | N |
| 53 | 2-ethoxyphenyl | 2-thienyl | 4 | N |
| 54 | 2-ethoxyphenyl | phenyl | 4 | N |

TABLE 2

Affinity to Dopamine Receptors (1 M)

Affinity to Dopamine Receptors (% Inhibition)

| Items | $D_1$ | $D_2$ | $D_3$ | $D_4$ |
|---|---|---|---|---|
| Compound No. 1 | 56.1 | 56.8 | 97.3 | 23.1 |
| Compound No. 2 | 71.3 | 56.6 | 94.5 | 10.6 |
| Compound No. 3 | 52.1 | 0.0 | 88.2 | 0.0 |
| Compound No. 4 | 59.1 | 16.4 | 93.9 | 0.0 |
| Compound No. 5 | 32.8 | 12.8 | 95.3 | 98.5 |
| Compound No. 6 | 26.8 | 14.7 | 71.4 | 101.3 |
| Compound No. 7 | 35.5 | 13.9 | 92.3 | 94.7 |
| Compound No. 8 | 17.3 | 32.3 | 84.9 | 80.8 |
| Compound No. 9 | 8.5 | 35.7 | 69.2 | 101.9 |
| Compound No. 10 | 26.7 | 24 | 83.5 | 99.6 |
| Compound No. 11 |  | 6.4 | 81.3 | 91.2 |
| Compound No. 12 |  | 35.0 | 84.7 | 63.8 |
| Compound No. 13 |  | 68.0 | 90.4 | 63.6 |
| Compound No. 14 |  | 41.3 | 86.1 | 28.6 |
| Compound No. 15 |  | 52.4 | 84.8 | 46.4 |
| Compound No. 16 |  | 31.5 | 80.3 | 94.8 |
| Compound No. 17 |  | 64.4 | 81.7 | 99.8 |
| Compound No. 18 |  | 38.2 | 96.8 | 100.7 |
| Compound No. 19 |  | 62.8 | 94.5 | 99.5 |
| Compound No. 20 |  | 47.9 | 89.4 | 86.2 |
| Compound No. 21 |  | 44.9 | 88.1 | 93.5 |
| Haloperidol | 90.7 | 89.2 | 89.6 | 97.6 |
| Compound No. 22 |  | 67.3 | 96.0 | 96.2 |
| Compound No. 23 | 58.9 | 49.3 | 110.4 | 21.6 |

TABLE 2-continued

Affinity to Dopamine Receptors (1 M)

Affinity to Dopamine Receptors (% Inhibition)

| Items | $D_1$ | $D_2$ | $D_3$ | $D_4$ |
|---|---|---|---|---|
| Compound No. 24 | 34 | 29.6 | 106.4 | 5.9 |
| Compound No. 25 | 22.5 | 4.5 | 109.3 | 15.4 |
| Compound No. 26 | 50.8 | 0.0 | 102.7 | 16.9 |
| Compound No. 27 | 46.7 | 0.0 | 107.8 | 0.0 |
| Compound No. 28 | 43.9 | 18.1 | 104.7 | 15.3 |
| Compound No. 29 | 32.6 | 0.0 | 102.4 | 31.6 |
| Compound No. 30 | 18.7 | 12.3 | 102.8 | 46.1 |
| Compound No. 31 | 60.6 | 23.3 | 105.6 | 63.8 |
| Compound No. 32 | 70 | 10.6 | 100.1 | 74.9 |
| Compound No. 33 | 52.9 | 6.7 | 104.4 | 62.4 |
| Compound No. 34 | 58.9 | 49.3 | 110.4 | 21.6 |
| Compound No. 35 | 75.8 | 15.6 | 102.1 | 45.1 |
| Compound No. 36 | 75.2 | 22.2 | 107.9 | 69 |
| Compound No. 37 | 52.2 | 57.3 | 112.5 | 91.3 |
| Compound No. 38 | 44.6 | 18.2 | 105 | 83 |
| Compound No. 39 | 23.9 | 23 | 105.1 | 80.1 |
| Compound No. 40 | 40.5 | 5.2 | 104.7 | 95.4 |
| Compound No. 41 | 44.3 | 18.8 | 105.7 | 93.8 |
| Compound No. 42 | 20.6 | 1.4 | 102.1 | 58.4 |
| Compound No. 43 | 59.6 | 20.1 | 104 | 81 |
| Compound No. 44 | 91.1 | 30.6 | 104.6 | 90.5 |
| Compound No. 45 |  | 26.8 | 102.2 | 46.0 |
| Haloperidol | 90.7 | 89.2 | 89.6 | 97.6 |
| Compound No. 46 | 75.8 | 15.6 | 102.1 | 45.1 |
| Compound No. 47 |  | 31.7 | 102.8 | 77.9 |
| Compound No. 48 |  | 10.7 | 99.8 | 40.2 |
| Compound No. 49 |  | 12.9 | 102.3 | 62.7 |
| Compound No. 50 |  | 71.2 | 101.7 | 42.5 |
| Compound No. 51 |  | 71.0 | 102.9 | 90.7 |
| Compound No. 52 |  | 63.3 | 103.1 | 83.4 |
| Compound No. 53 |  | 54.1 | 103.8 | 93.4 |
| Compound No. 54 |  | 29.9 | 101.8 | 77.6 |
| Haloperidol | 90.7 | 89.2 | 89.6 | 97.6 |

TABLE 3

IC$_{50}$ for Dopamine Receptors (nM)

| Items |  | $D_1$ | $D_2$ | $D_3$ | $D_4$ |
|---|---|---|---|---|---|
| Compound No. 6 |  | 1690 | 3500 | 770 | 44 |
| Compound No. 8 |  | 1230 | 4000 | 260 | 32 |
| Compound No. 9 |  | 3360 | 6990 | 720 | 4 |
| Compound No. 10 |  | 1710 | 7570 | 390 | 34 |
| Compound No. 12 | Racemic | — | 2013 | 577 | 924 |
|  | (+)-Isomer | — | 2132 | 333 | 1021 |
|  | (−)-Isomer | — | 1876 | 598 | 986 |
| Compound No. 13 | Racemic | — | 874 | 325 | 933 |
|  | (+)-Isomer | — | 628 | 222 | 952 |
|  | (−)-Isomer | — | 895 | 457 | 939 |
| Compound No. 24 |  | 420 | 6920 | 45 | 3560 |
| Compound No. 26 |  | 420 | 17400 | 38 | 11720 |
| Compound No. 28 |  | 260 | 2210 | 36 | 3450 |
| Compound No. 32 |  | 110 | 9980 | 38 | 117 |
| Compound No. 33 |  | 310 | 18800 | 35 | 180 |
| Compound No. 34 |  | 320 | 15300 | 41 | 832 |
| Compound No. 38 |  | 710 | 1340 | 14 | 77 |
| Compound No. 39 |  | 2880 | 1900 | 12 | 395 |
| Compound No. 40 |  | 870 | 2000 | 15 | 53 |
| Compound No. 41 |  | 980 | 3300 | 11 | 32 |
| Compound No. 42 |  | 1950 | 7850 | 22 | 304 |
| Compound No. 43 |  | 230 | 7260 | 45 | 221 |
| Compound No. 44 |  | 110 | 4380 | 35 | 136 |
| Compound No. 45 |  |  | 17200 | 28 | 425 |
| Compound No. 46 |  |  | 2660 | 24 | 89 |
| Compound No. 50 |  |  | 910 | 26 | 49 |
| Compound No. 51 |  |  | 430 | 45 | 78 |
| Compound No. 52 |  |  | 540 | 6 | 43 |

TABLE 3-continued

IC$_{50}$ for Dopamine Receptors (nM)

| Items | $D_1$ | $D_2$ | $D_3$ | $D_4$ |
|---|---|---|---|---|
| Compound No. 53 |  | 880 | 9 | 19 |
| Compound No. 54 |  | 1550 | 21 | 52 |
| Haloperidol |  | 80 | 57 | 65 |

As explained above, since the compound according to the present invention represented by Formula (1) has superior and selective inhibitory activity against dopaminie D$_3$ or D$_4$ receptors, it may be effective in the treatment of schizophrenia in mental disease.

What is claimed is:

1. A method of treating schizophrenia comprising administering to a patient in need thereof a composition comprising an effective amount of at least one isoxazolylalkylpiperazine derivative represented by the following formula (1), in racemic form or as individual optical isomers or a pharmaceutically acceptable salt thereof,

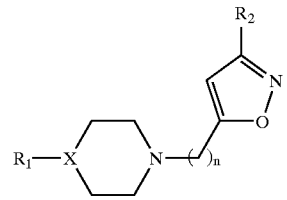

(1)

wherein R$_1$ represents at least one substituent selected from the group consisting of an aryl group, a phenylmethyl group, a diphenylmethyl group and a 2-keto-1-benzimidazolinylgroup, wherein the substituent may have at least one further substituent selected from the group consisting of C$_1$–C$_6$ alkyl group, C$_1$–C$_6$ alkoxy group and a fluorine atom, a chlorine atom and a trifluoromethyl group;

R$_2$ represents at least one substituent selected from the group consisting of an aryl group, a phenylvinyl group and a thiophene group, wherein the substituent may have at least one further substituent selected from the group consisting of a fluorine atom, a chlorine atom, a nitro group, a C$_1$–C$_6$ alkyl group, a C$_1$–C$_6$ alkoxy group and a phenoxy group;

X represents CH or a nitrogen atom; and n represents 3 or 4.

2. A method as claimed in claim 1 wherein said composition further comprises at least one pharmaceutically acceptable carrier.

3. A method as claimed in claim 1 wherein said composition is in at least one of the following forms:
tablet, capsule, troches, liquid solution and emulsion.

4. A method as claimed in claim 1 wherein said composition is administered in a dosage of about 0.01 to 400 mg/day.

5. A method according to claim 1 wherein said compound is at least one member selected from the group consisting of:
3-(3-nitrophenyl)-5-[3-(4-phenylpiperazinyl)propyl]isoxazole;
2-{5-[3-(4-phenylpiperazinyl)propyl]isoxazol-3-yl}thiophene;
5-[3-(4-phenylpiperazinyl)propyl]-3-(2-phenylvinyl)isoxazole;
3-(4-chlorophenyl)-5-[3-(4-phenylpiperazinyl)propyl]isoxazole;

3-(4-fluorophenyl)-5-[3-(4-phenylpiperazinyl)propyl]
isoxazole;
1-phenoxy-3-{5-[3-(4-phenylpiperazinyl)propyl]
isoxazol-3-yl}benzene;
3-phenyl-5-[3-(4-phenylpiperazinyl)propyl]isoxazole;
5-{3-[4-(diphenylmethyl)piperazinyl]propyl}-3-
phenylisoxazole;
5-{3-[4-(diphenylmethyl)piperazinyl]propyl}-3-(4-
chlorophenyl)isoxazole;
5-{3-[4-(diphenylmethyl)piperazinyl]propyl}-3-(3-
nitrophenyl)isoxazole;
4-(5-{3-[4-(diphenylmethyl)piperazinyl]propyl}isozazol-
3-yl)-1,2-dimethoxybenzene;
2-(5-{3-[4-diphenylmethyl]piperazinyl]propyl)isoxazol-
3-yl}thiophene;
5-{3-[4-(diphenylmethyl)piperazinyl]propyl}-3-(4-
fluorophenyl)isoxazole;
1-(5-{3-[4-(diphenylmethyl)piperazinyl]
propyl}isoxazol-3-yl)-3-phenoxybenzene;
5-{3-[4-(diphenylmethyl)piperazinyl]propyl}-3-(2-
phenylvinyl)isoxazole;
2-methoxy-1-{4-[3-(3-phenylisoxazol-5-yl)propyl]
piperazinyl}benzene;
1-(4-{3-[3-(4-chlorophenyl)isoxazol-5-yl]
propyl}piperazinyl)2-methoxybenzene;
3-phenyl-5-[3-(4-{[2-(trifluoromethyl)phenyl]
methyl}piperazinyl)propyl]isoxazole;
3-(4-chlorophenyl)-5-[3-(4-{[2-(trifluoromethyl)phenyl]
methyl}piperazinyl)propyl]isoxazole;
2-methoxy-1-(4-{3-[3-(3-phenoxyphenyl)isoxazol-5-yl]
propyl}piperazinyl)benzene;
2-methoxy-1-(4-{3-[3-(2-phenylvinyl)isoxazol-5-yl]
propyl}piperazinyl)benzene;
1,2-dimethoxy-(4-{5-[3-(4-phenylpiperazinyl)propyl]
isoxazol-3-yl}benzene;
1,2-dimethoxy-4-{5-[3-(4-{[2-(trifluoromethyl)phenyl]
methyl}piperazinyl)propyl]isoxazol-3yl}benzene;
1,2-dimethoxy-4-(5-{3-[4-(2-methoxyphenyl)
piperazinyl]propyl}isoxazol-3-yl)benzene;
2-methoxy-1-(4-{3-[3-(3-nitrophenyl)isoxazol-5-yl]
propyl}piperazinyl)benzene;
3-(3-nitrophenyl)-5-[3-(4-{[2-(trifluoromethyl)phenyl]
methyl}piperazinyl)propyl]isoxazole;
2-{5-[3-(4-{[2-(trifluoromethyl)phenyl]
methyl}piperazinyl)propyl]isoxazol-3-yl}thiophene;
2-methoxy-1-{4-[3-(3-(2-thienyl)isoxazol-5-yl)propyl]
piperazinyl}benzene;
1-(4-{3-[3-(4-fluorophenyl)isoxazol-5-yl]
propyl}piperazinyl)-2-methoxybenzene;
5-{3-[4-benzylpiperazinyl]propyl}-3-(2-phenylvinyl)
isoxazole;
3-(2-phenylvinyl)-5-[3-(4-{[2-(trifluoromethyl)phenyl]
methyl}piperazinyl)propyl]isoxazole;
1-(1-{3-[3-(2-phenylvinyl)isoxazol-5-yl]propyl}-4-
piperidyl)-3-hydrobenzimidazol-2-on;
1-(1-{3-[3-(4-chlorophenyl)isoxazol-5-yl]propyl}-4-
piperidyl)-3-hydrobenzimidazol-2-on;
1-(1-{3-[3-(3-nitrophenyl)isoxazol-5-yl]propyl}-4-
piperidyl)-3-hydrobenzimidazol-2-on;
1-phenoxy-3-{5-[3-(4-{[2-(trifluoromethyl)phenyl]
methyl}piperazinyl)propyl]isoxazol-3-yl}benzene;

1-(1-{3-[3-(3,4-dimethoxyphenyl)isoxazol-5-yl]propyl}-
4-piperidyl)-3-hydrobenzimidazol-2-on;
1-(1-{3-[3-(4-fluorophenyl)isoxazol-5-yl]propyl}-4-
piperidyl)-3-hydrobenzimidazol-2-on;
1-{1-[3-(3-phenylisoxazol-5-yl)propyl]-4-piperidyl}-3-
hydrobenzimidazol-2-on;
1-(1-{3-[3-(3-phenoxyphenyl)isoxazol-5-yl]propyl}-4-
piperidyl)-3-hydrobenzimidazol-2-on;
2-methoxy-1-{4-[3-(3-(1,3-thiazol-2-yl)isoxazol-5-yl)
propyl]piperazinyl}benzene;
2-(5-{3-[4-(diphenylmethyl)piperazinyl]
propyl}isoxazol-3-yl)-1,3-thiazole;
3-(4-chlorophenyl)-5-(3-[4-benzylpiperazinyl]propyl)
isoxazole;
3-(3-nitrophenyl)-5-{3-[4-benzylpiperazinyl]
propyl}isoxazole;
1,2-dimethoxy-4-(5-{3-[4-benzylpiperazinyl]
propyl}isoxazol-3-yl)benzene;
2,4-dimethoxy-1-(5-{3-[4-benzylpiperazinyl]
propyl}isoxazol-3-yl)benzene;
2-(5-{3-[4-benzylpiperazinyl]propyl}isoxazol-3-yl)
thiophene;
2-(5-{3-[4-benzylpiperazinyl]propyl}isoxazol-3-yl)-1,3-
thiazole;
3-(4-fluorophenyl)-5-{3-[4-benzylpiperazinyl]
propyl}isoxazole;
3-phenyl-5-{3-[4-benzylpiperazinyl]propyl}isoxazole;
1-(5-{3-[4-benzylpiperazinyl]propyl}isoxazol-3-yl)-3-
phenoxybenzene;
1-(5-{3-[4-(diphenylmethyl)piperazinyl]
propyl}isoxazol-3-yl)-2,4-dimethoxybenzene;
2,4-dimethoxy-1-{5-[3-(4-{[2-(trifluoromethyl)phenyl]
methyl}piperazinyl)propyl]isoxazol-3-yl}benzene;
1-(1-{3-[3-(2,4-dimethoxyphenyl)isoxazol-5-yl]propyl}-
4-piperidyl)-3-hydrobenzimidazol-2-on;
1-(1-{3-[3-(2-thienyl)isoxazol-5-yl]propyl}-4-piperidyl)-
3-hydrobenzimidazol-2-on
3-(4-fluorophenyl)-5-[3-(4-{[2-(trifluoromethyl)phenyl]
methyl}piperazinyl)propyl]isoxazole;
5-{3-[4-(4-fluorophenyl)piperazinyl]propyl}-3-
phenylisoxazole;
3-methoxy-1-(4-{3-[3-(3-nitrophenyl)isoxazol-5-yl]
propyl}piperazinyl)benzene;
1-(4-{3-[3-(3,4-dimethoxyphenyl)isoxazol-5-yl]
propyl}piperazinyl)-3-methoxybenzene;
3-(4-chlorophenyl)-5-{3-[4-(2-chlorophenyl)piperazinyl]
propyl}isoxazole;
4-(5-{3-[4-(2-chlorophenyl)piperazinyl]propyl}isoxazol-
3-yl)-1,2-dimethybenzene;
2-(5-{3-[4-(2-chlorophenyl)piperazinyl]propyl}isoxazol-
3-yl)thiophene;
5-{3-[4-(2-chlorophenyl)piperazinyl]propyl}-3-
phenylisoxazole;
1-(5-{3-[4-(2-chlorophenyl)piperazinyl]propyl}isoxazol-
3-yl)-3-phenoxybenzene;
1-(4-{3-[3-(3,4-dimethylphenyl)isoxazol-5-yl]
propyl}piperazinyl)-2-ethoxybenzene;
2-ethoxy-1-{4-[3-(3-(2-thienyl)isoxazol-5-yl)propyl]
piperazinyl}benzene;
2-ethoxy-1-(4-{3-[3-(2-phenylvinyl)isoxazol-5-yl]
propyl}piperazinyl)benzene;

5-{4-[4-(diphenylmethyl)piperazinyl]butyl}-3-(4-fluorophenyl)isoxazole;
5-{4-[4-(diphenylmethyl)piperazinyl]butyl}-3-(3-nitrophenyl)isoxazole;
4-(5-{4-[4-(diphenylmethyl)piperazinyl]butyl}isoxazol-3-yl)-1,2-dimethoxybenzene;
1-(5-{4-[4-(diphenylmethyl)piperazinyl]butyl}isoxazol-3-yl)-2,4-dimethoxybenzene;
5-{4-[4-(diphenylmethyl)piperazinyl]butyl}-3-phenylisoxazole;
2-{5-[4-(4-{[2-(trifluoromethyl)phenyl]methyl}piperazinyl)butyl]isoxazol-3-yl}thiophene;
3-phenyl-5-[4-(4-{[2-(trifluoromethyl)phenyl]methyl}piperazinly)butyl]isoxazole;
1-(5-{4-[4-(diphenylmethyl)piperazinyl]butyl}isoxazol-3-yl)-3-phenoxybenzene;
5-{4-[4-(diphenylinethyl)piperazinyl]butyl}-3-(2-phenylvinyl)isoxazole;
3-phenoxy-1-{15-[4-(4-{[2-(trifluoromethyl)phenyl]methyl}piperazinyl)butyl]isoxazol-3-yl}benzene;
3-(2-phenylvinyl)-5-[4-(4-{[2-(trifluoromethyl)phenyl]methyl}piperazinyl)butyl]isoxazole;
1,2-dimethoxy-4-{5-[4-(4-{[2-(trifluoromethyl)phenyl]methyl}piperazinyl)butyl]isoxazol-3-yl}benzene;
2,4-dimethoxy-1-{5-[4-(4-{[2-(trifluoromethyl)phenyl]methyl}piperazinyl)butyl]isoxazol-3-yl}benzene;
3-(4-fluorophenyl)-5-[4-(4-{[2-(trifluoromethyl)phenyl]methyl}piperazinyl)butyl]isoxazole;
3-(3-nitrophenyl)-5-[4-(4-{[2-(trifluoromethyl)phenyl]methyl}piperazinyl)butyl]isoxazole;
1-(1-{4-[3-(4-fluorophenyl)isoxazol-5-yl]butyl}-4-piperidyl)-3-hydrobenzimidazol-2-on;
1-(1-{4-[3-(3-nitrophenyl)isoxazol-5-yl]butyl}-4-piperidyl)-3-hydrobenzimidazol-2-on;
1-{1-[4-(3-(2-thienyl)isoxazol-5-yl)butyl]-4-piperidyl}-3-hydrobenzimidazol-2-on;
1-{1-[4-(3-phenylisoxazol-5-yl)butyl]-4-piperidyl-3-hydrobenzimidazol-2-on;
1-(1-{4-[3-(3,4-dimethoxyphenyl)isoxazol-5-yl]butyl}-4-piperidyl)-3-hydrobenzimidazol-2-on;
1,2-dimethoxy-4-(5-{4-[4-benzylpiperazinyl]butyl}isoxazol-3-yl)benzene;
2-(5-4-[4-(diphenylmethyl)piperazinyl]butyl}isoxazol-3-yl)thiophene;
2-(5-{4-[4-benzylpiperazinyl]butyl}isoxazol-3-yl)thiophene;
1-(5-{4-[4-benzylpiperazinyl]butyl}isoxazol-3-yl)-3-phenoxybenzene;
5-{4-[4-benzylpiperazinyl]butyl}-3-(2-phenylvinyl)isoxazole;
1-(1-{4-[3-(3-phenoxyphenyl)isoxazol-5-yl]butyl}-4-piperidyl)-3-hydrobenzimidazol-2-on;
1-(1-{4-[3-(2-phenylvinyl)isoxazol-5-yl]butyl}-4-piperidyl)-3- hydrobenzimidazol-2-on;
3-(4-fluorophenyl)-5-{4-[4-benzylpiperazinyl]butyl}isoxazole;
3-(3-nitrophenyl)-5-{4-[4-benzylpiperazinyl]butyl}isoxazole;
2,4-dimethoxy-1-(5-{4-[4-benzylpiperazinyl]butyl}isoxazol-3-yl)benzene;
1-(1-{4-[3-(2,4-dimethoxyphenyl)isoxazol-5-yl]butyl}-4-piperidyl)-3-hydrobenzimidazol-2-on;
3-phenyl-5-{4-[4-benzylpiperazinyl]butyl}isoxazole;
3-(4-fluorophenyl)-5-[4-(4-phenylpiperazinyl)butyl]isoxazole;
3-(3-nitrophenyl)-5-[4-(4-phenylpiperazinyl)butyl]isoxazole;
1,2-dimethoxy-4-{5-[4-(4-phenylpiperazinyl)butyl]isoxazol-3-yl}benzene;
2,4-dimethoxy-1-{5-[4-(4-phenylpiperazinyl)butyl]isoxazol-3-yl}benzene;
2-{5-[4-(4-phenylpiperazinyl)butyl]isoxazol-3-yl}thiophene;
3-phenyl-5-[4-(4-phenylpiperazinyl)butyl]isoxazole;
1-(4-{4-[3-(4-fluorophenyl)isoxazol-5-yl]butyl}piperazinyl)-2-methoxybenzene;
2-methoxy-1-(4-{4-[3-(3-nitrophenyl)isoxazol-5-yl]butyl}piperazinyl)benzene;
1-(4-{4-[3-(3,4-dimethoxyphenyl)isoxazol-5-yl]butyl piperazinyl)-2-methoxybenzene;
1-(4-{4-[3-(2,4-dimethoxyphenyl)isoxazol-5-yl]butyl}piperazinyl)-2-methoxybenzene;
2-methoxy-1-{4-(3-(2-thienyl)isoxazol-5-yl)butyl]piperazinyl}benzene;
2-methoxy-1-{4-[4-(3-phenylisoxazol-5-yl)butyl]piperazinyl}benzene;
3-phenoxy-1-{5-[4-(4-phenylpiperazinyl)butyl]isoxazol-3-yl}benzene;
5-[4-(4-phenylpiperazinyl)butyl]-3-(2-phenylvinyl)isoxazole;
1-(5-{4-[4-(2-methoxyphenyl)piperazinyl]butyl}isoxazol-3-yl)-3-phenoxybenzene;
2-methoxy-1-(4-{4-[3-(2-phenylvinyl)isoxazol-5-yl]butyl}piperazinyl)benzene;
3-(4-fluorophenyl)-5-{4-[4-(4-fluorophenyl)piperazinyl]butyl}isoxazole;
3-methoxy-1-(4-{4-[3-(3-nitrophenyl)isoxazol-5-yl]butyl}piperazinyl)benzene;
5-{4-[4-(2-fluorophenyl)piperazinyl]butyl}-3-(2-phenylvinyl)isoxazole;
1,2-dimethoxy-4-(5-{4-[4-(2-methylphenyl)piperazinyl]butyl}isoxazol-3-yl)benzene; and
pharmaceutically acceptable salts thereof.

6. A method as claimed in claim 1 wherein said composition further comprises at least one pharmaceutically acceptable carrier.

7. A method as claimed in claim 1 wherein said composition is in at least one of the following forms: tablet, capsule, troches, liquid solution and emulsion.

8. A method as claimed in claim 1 wherein said composition is administered in a dosage of about 0.01 to 400 mg/day.

* * * * *